US006902733B2

(12) United States Patent
Collen

(10) Patent No.: US 6,902,733 B2
(45) Date of Patent: Jun. 7, 2005

(54) STAPHYLOKINASE DERIVATIVES WITH POLYETHYLENEGLYCOL

(75) Inventor: Désire José Collen, Winksele-Herent (BE)

(73) Assignees: Desire' Jose' Collen, Winksele-Herent (BE); Leuven Research & Development VZW (BE)

( * ) Notice: Subject to any disclaimer, the term of this patent is extended or adjusted under 35 U.S.C. 154(b) by 464 days.

(21) Appl. No.: 09/728,670

(22) Filed: Nov. 30, 2000

(65) Prior Publication Data

US 2002/0091076 A1 Jul. 11, 2002

Related U.S. Application Data

(60) Division of application No. 09/020,018, filed on Feb. 6, 1998, now Pat. No. 6,383,483, which is a continuation-in-part of application No. 08/784,971, filed on Jan. 16, 1997, now Pat. No. 5,951,980, which is a continuation-in-part of application No. 08/499,092, filed on Jul. 6, 1995, now abandoned, which is a continuation-in-part of application No. 08/371,505, filed on Jan. 11, 1995, now Pat. No. 5,695,754.

(51) Int. Cl.[7] ........................ A61K 38/48; A61K 39/02; C12N 9/52

(52) U.S. Cl. ................................ 424/94.64; 424/243.1; 435/220; 514/2; 530/350

(58) Field of Search ........................... 424/94.64, 243.1; 435/220; 514/2; 530/350

(56) References Cited

PUBLICATIONS

Collen et al., *Circulation*, vol. 94, pp. 197–206, 1996.*
Collen et al., *Fibrinolysis*, vol. 6, pp. 226–231, 1992.
Collen et al., "Comparative Thrombolytic and Immunogenic Properties of Staphylokinase and Streptokinase", *Fibrinolysis*, vol. 6, pp. 232–242, 1992.
Collen et al., *Circulation*, vol. 87, pp. 996–1006, 1993.

* cited by examiner

*Primary Examiner*—Michael Pak
(74) *Attorney, Agent, or Firm*—Webb Ziesenheim Logsdon Orkin & Hanson, P.C.

(57) ABSTRACT

Methods for the identification, production and use of staphylokinase derivatives characterized by a reduced immunogenicity after administration in patients. The derivatives of the invention are obtained by preparing a DNA fragment comprising at least the part of the coding sequence of staphylokinase that provides for its biological activity; performing in vitro site-directed mutagenesis on the DNA fragment to replace one or more codons for wild-type amino acids by a codon for another amino acid; cloning the mutated DNA fragment in a suitable vector; transforming or transfecting a suitable host cell with the vector; culturing the host cell under conditions suitable for expressing the DNA fragment; and purifying the expressed staphylokinase derivative to homogeneity. Preferably the DNA fragment is a 453 bp EcoRI-HindIII fragment of the plasmid pMEX602sakB, (pMEX.SakSTAR), the in vitro site-directed mutagenesis is performed by spliced overlap extension polymerase chain reaction and the mutated DNA fragment is expressed in *E. coli* strain TG1 or WK6. The invention also relates to pharmaceutical compositions comprising at least one of the staphylokinase derivatives according to the invention together with a suitable excipient, for treatment of arterial thrombosis.

7 Claims, 5 Drawing Sheets

1 ... 14
Ser Ser Ser Phe Asp Lys Gly Lys Tyr Lys Lys Gly Asp Asp

15 ... 28
Ala Ser Tyr Phe Glu Pro Thr Gly Pro Tyr Leu Met Val Asn

29 ... 42
Val Thr Gly Val Asp Ser Lys Gly Asn Glu Leu Leu Ser Pro

43 ... 56
His Tyr Val Glu Phe Pro Ile Lys Pro Gly Thr Thr Leu Thr

57 ... 70
Lys Glu Lys Ile Glu Tyr Tyr Val Glu Trp Ala Leu Asp Ala

71 ... 84
Thr Ala Tyr Lys Glu Phe Arg Val Val Glu Leu Asp Pro Ser

85 ... 98
Ala Lys Ile Glu Val Thr Tyr Tyr Asp Lys Asn Lys Lys Lys

99 ... 112
Glu Glu Thr Lys Ser Phe Pro Ile Thr Glu Lys Gly Phe Val

113 ... 126
Val Pro Asp Leu Ser Glu His Ile Lys Asn Pro Gly Phe Asn

127 ... 136
Leu Ile Thr Lys Val Val Ile Glu Lys Lys

Figure 1

STAPHYLOKINASE DERIVATIVES WITH POLYETHYLENEGLYCOL

CROSS-REFERENCE TO RELATED APPLICATIONS

This application is a divisional of U.S. patent application Ser. No. 09/020,018, filed Feb. 6, 1998 now U.S. Pat. No. 6,383,483, which is a continuation-in-part of U.S. patent application Ser. No. 08/784,971, filed Jan. 16, 1997, now U.S. Pat. No. 5,951,980, issued Sep. 14, 1999, which is a continuation-in-part of U.S. patent application Ser. No. 08/499,092, filed Jul. 6, 1995 now abandoned, which is a continuation-in-part of U.S. patent application Ser. No. 08/371,505, filed Jan. 11, 1995, now U.S. Pat. No. 5,695, 754, issued Dec. 9, 1997.

BACKGROUND OF THE INVENTION

1. Field of the Invention

This invention relates to new staphylokinase derivatives with reduced immunogenicity, their identification, production and use in the treatment of arterial thrombosis and the preparation of a pharmaceutical composition for treating arterial thrombosis. More in particular it relates to the use of engineered staphylokinase derivatives for the preparation of a pharmaceutical composition for treating myocardial infarction.

2. Description of the Related Art

Staphylokinase, a protein produced by certain strains of *Staphylococcus aureus*, which was shown to have profibrinolytic properties more than 4 decades ago (1,2) appears to constitute a potent thrombolytic agent in patients with acute myocardial infarction (3,4). The staphylokinase gene has been cloned from the bacteriophages sakøC (5) and sak42D (6) as well as from the genomic DNA (sakSTAR) of a lysogenic *Staphylococcus aureus* strain (7). The staphylokinase gene encodes a protein of 163 amino acids, with amino acid 28 corresponding to the $NH_2$-terminal residue of full length mature staphylokinase (6,8,9). The mature protein sequence of the wild-type variant SakSTAR (9) is represented in FIG. 1. Only four nucleotide differences were found in the coding regions of the sakøC, sak42D and sakSTAR genes, one of which constituted a silent mutation (6,8,9).

In a plasma milieu, staphylokinase is able to dissolve fibrin clots without associated fibrinogen degradation (10–12). This fibrin-specificity of staphylokinase is the result of reduced inhibition by $\alpha_2$-antiplasmin of plasmin-.staphylokinase complex bound to fibrin, recycling of staphylokinase from the plasmin.staphylokinase complex following inhibition by $\alpha_2$-antiplasmin, and prevention of the conversion of circulating plasminogen.staphylokinase to plasmin.staphylokinase by $\alpha_2$-antiplasmin (13–15). In addition staphylokinase has a weak affinity for circulating but a high affinity for fibrin-bound plasminogen (16) and staphylokinase requires $NH_2$-terminal processing by plasmin to display its plasminogen activating potential (17). In several experimental animal models, staphylokinase appears to be equipotent to streptokinase for the dissolution of whole blood or plasma clots, but significantly more potent for the dissolution of platelet-rich or retracted thrombi (18,19).

Staphylokinase is a heterologous protein and is immunogenic in man. The intrinsic immunogenicity of staphylokinase, like that of streptokinase, clearly hampers its unrestricted use. Not only will patients with preexisting high antibody titers be refractory to the thrombolytic effect of these agents, but allergic side effects and occasional life-threatening anaphylaxis may occur (20). Because both streptokinase and staphylokinase are heterologous proteins, it is not obvious that their immunogenicity could be reduced by protein engineering. Indeed, no successful attempts to generate active low molecular weight fragments from streptokinase have been reported. In staphylokinase, deletion of the $NH_2$-terminal 17 amino acids or the COOH-terminal 2 amino acids inactivates the molecule, which in addition is very sensitive to inactivation by site-specific mutagenesis (21).

Nevertheless, we have, surprisingly, found that the wild-type staphylokinase variant SakSTAR (9) contains three non-overlapping immunodominant epitopes, at least two of which can be eliminated by specific site-directed mutagenesis, without inactivation of the molecule (22). These engineered staphylokinase variants are less reactive with antibodies elicited in patients treated with wild-type staphylokinase, and are significantly less immunogenic than wild-type staphylokinase, as demonstrated in rabbit and baboon models and in patients with peripheral arterial occlusion (22).

SUMMARY OF TEE INVENTION

The present invention relates to general methods for the identification, production and use of staphylokinase derivatives showing a reduced antigenicity and immunogenicity as compared to wild-type staphylokinase. The derivatives have essentially the amino acid sequence of wild-type staphylokinase or modified versions thereof and essentially intact biological activities, but have a reduced reactivity with a panel of murine monoclonal antibodies and/or with antibodies induced in patients by treatment with wild-type SakSTAR.

The invention also relates to a method for producing the derivatives of the invention by preparing a DNA fragment comprising at least the part of the coding sequence of staphylokinase that provides for its biological activity; performing in vitro site-directed mutagenesis on the DNA fragment to replace one or more codons for wild-type amino acids by a codon for another amino acid; cloning the mutated DNA fragment in a suitable vector; transforming or transfecting a suitable host cell with the vector; culturing the host cell under conditions suitable for expressing the DNA fragment and purifying the expressed staphylokinase derivative to homogeneity; preferably the DNA fragment is a 453 bp EcoRI-HindIII fragment of the plasmid pMEX602sakB (22, 23), the in vitro site-directed mutagenesis is preferably performed by spliced overlap extension polymerase chain reaction with Vent DNA polymerase (New England Biolabs) or Taq polymerase (Boehringer Mannheim) and with available or generated wildtype sakSTAR or sakSTAR variants as template (24).

The invention also relates to pharmaceutical compositions comprising at least one of the staphylokinase derivatives according to the invention together with a suitable excipient, for treatment of arterial thrombosis. Pharmaceutical compositions, containing less immunogenic staphylokinase variants as the active ingredient, for treating arterial thrombosis in human or veterinary practice may take the form of powders or solutions and may be used for intravenous, intraarterial or parenteral administration. Such compositions may be prepared by combining (e.g. mixing, dissolving etc.) the active compound with pharmaceutically acceptable excipients of neutral character (such as aqueous or non-aqueous solvents, stabilizers, emulsifiers, detergents, additives), and further, if necessary with dyes.

Furthermore the invention relates to the use of the staphylokinase derivatives for the treatment of arterial thrombosis, in particular myocardial infarction, and to the use of staphylokinase derivatives for the preparation of a pharmaceutical composition for the treatment of arterial thrombosis, in particular myocardial infarction.

BRIEF DESCRIPTION OF THE DRAWINGS

FIG. 1 is a protein sequence of wild-type staphylokinase, SakSTAR (SEQ ID NO: 10). Numbering starts with the $NH_2$-terminal amino acid of mature full length staphylokinase.

Squares: single amine acid substitutions; circles: combined (2 to 3) amino acid to Ala substitutions.

Figure 4:
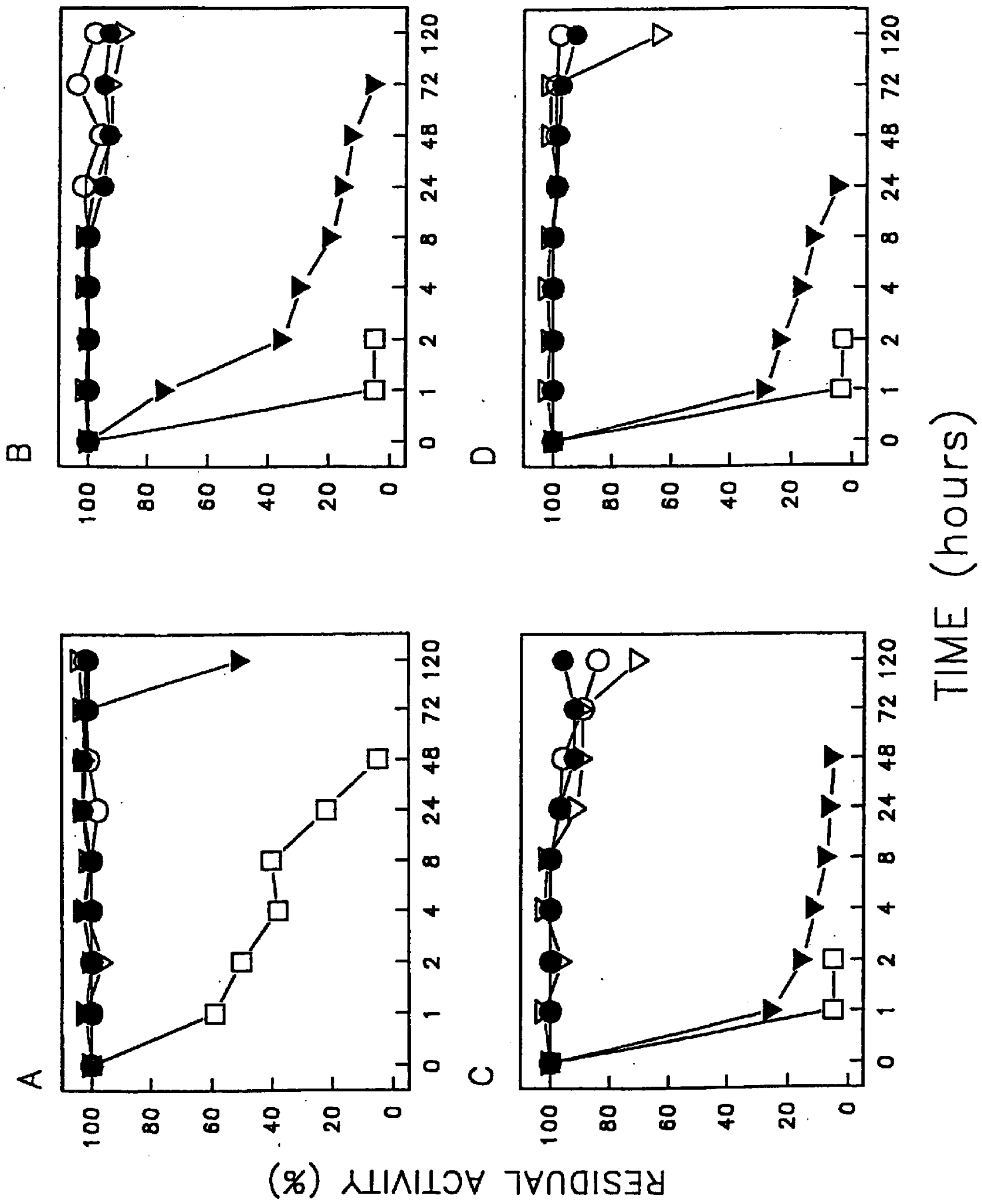

FIG. 4 shows temperature stability of SakSTAR, (A); SakSTAR (K74Q,E80A, D82A, K130T, K135R), (B); SakSTAR (E65D, K74R, E80A, D82A, K130T, K135R), (C); and SakSTAR (K35A, E65D, K74Q, E80A, D82A, K130T, K135R), (D).

(○): 40° C.; (●): 20° C.; (V): 37° C.; (▼): 56° C.; (□): 70° C.

Figure 5:
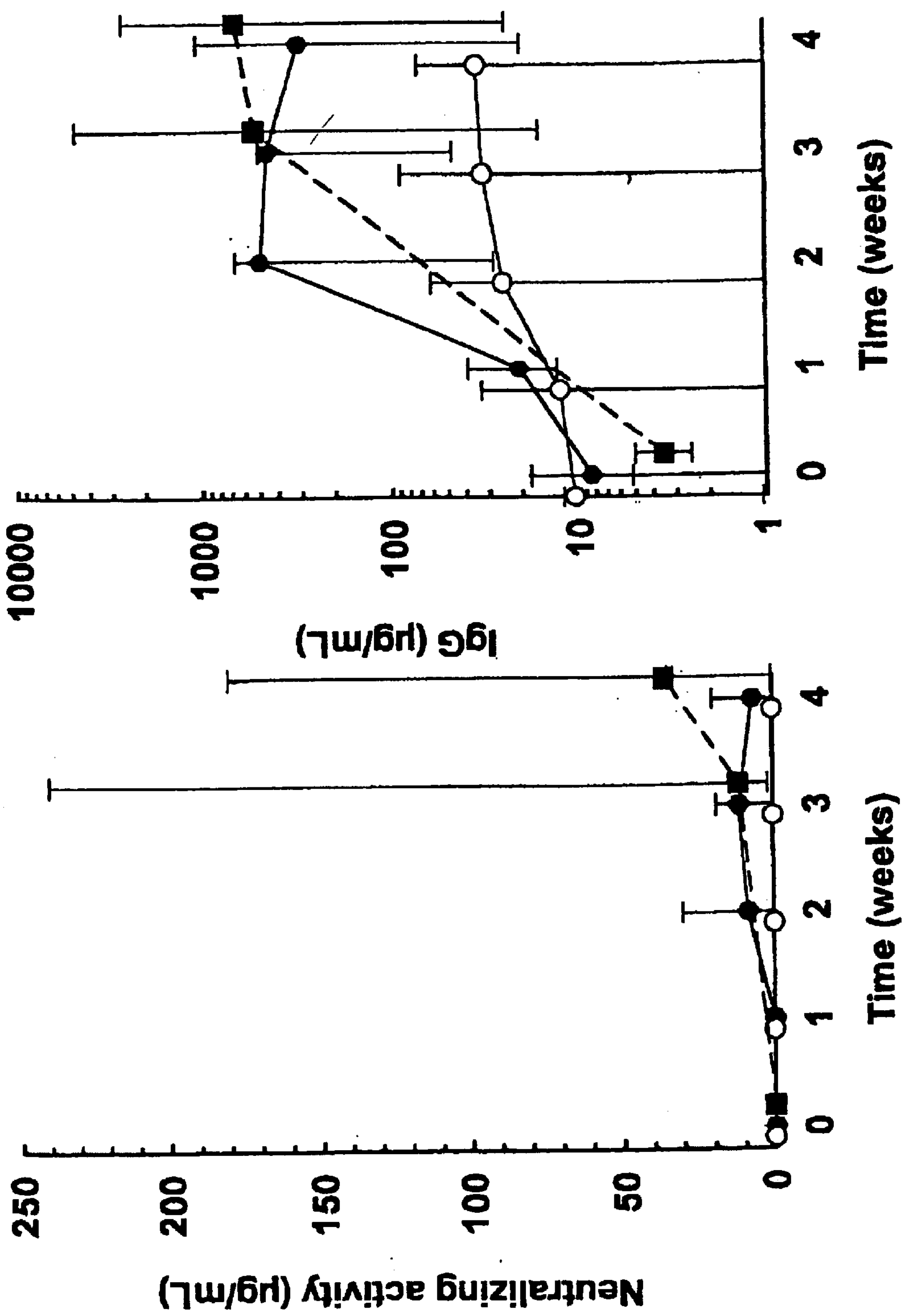

FIG. 5 is a time course of neutralizing activities (left panel) and specific IgG against administered agent (right panel) following nitra-arterial infusion of SakSTAR (circles, n=15), SakStar (K74Q, E80A, D82A, K130T, K135R) (squares, n=6) or SakSTAR (E65D, K74R, E80A, D82A, K130T, K135R) (triangles, n=6) in patients with peripheral arterial occlusion. The data represent median values and 15–85 percentile ranges, in μg/mL.

DETAILED DESCRIPTION OF THE PREFERRED EMBODIMENTS

In the above and the following the terms "derivatives", "mutants" and "variants" are used interchangeably.

The present invention will be demonstrated in more detail in the following examples, that are however not intended to be limiting to the scope of the invention. Based on the present invention other variants and improvements will be obvious for the person skilled in the art. Thus random mutagenesis is likely to generate alternative mutants with reduced immunogenicity and possibly increased functional activity, whereas deletions or substitution with other amino acids may yield additional variants with reduced immunogenicity.

EXAMPLE 1

Epitope Mapping of Wild-type Staphylokinase

The epitope specificity of a panel of 15 murine MAbs (22) raised against wild-type SakSTAR was determined by real-time biospecific interaction analysis (BIA) with the BIAcore instrument (Pharmacia, Biosensor AB, Uppsala, Sweden). The MAbs were immobilized on the surface of the Sencor Chip CM5 with the Amine Coupling Kit (Pharmacia Biosensor AB) as recommended by the manufacturer (25). Immobilization was performed from protein solutions at a concentration of 20 μg/mL in 10 mmol/L sodium acetate at pH 5.0 at a flow rate of 5 μL/min during 6 minutes. This resulted in covalent attachment of 5,000 to 10,000 resonance unit (RU) of antibody (corresponding to 0.035 to 0.07 pmol/$mm^2$). The SakSTAR solutions were passed by continuous flow at 20° C. past the sensor surface. At least four concentrations of each analyte (range, 50 nmol/L to 50 μmol/L) in 10 mmol/L HEPES, 3.4 mmol/L EDTA, 0.15 mol/L NaCl, and 0.005% Surfactant P20, pH 7.2, were injected at a flow rate of 5 μL/min during 6 minutes in the association phase. Then sample was replaced by buffer, also at a flow rate of 5 μL/min during 6 minutes. After each cycle, the surface of the sensor chip was regenerated by injection of 5 μL of 15 mmol/L HCl. Apparent association ($k_{ass}$) and apparent dissociation ($k_{diss}$) rate constants were derived from the sensorgrams as described in detail elsewhere (26), and association equilibrium constants ($K_A$) calculated as their ratio.

Determination of the equilibrium association constants for the binding of wild-type and variant SakSTAR to insolubilized MAbs (Table 1) yielded apparent association constants of $10^7$ to $10^8$ $(mol/L)^{-1}$, which are one to two orders of magnitude lower than the apparent association constants previously obtained for the binding of these MAbs to insolubilized wild-type SakSTAR (22). If the MAbs instead of the SakSTAR variants are insolubilized, avidity effects of the bivalent MAbs are indeed avoided. The present values are indeed in better agreement with known association constants of Mabs, and therefore this "reversed" procedure was used throughout the present invention.

In the tables the column indicated with "Variant" states the various staphylokinase derivatives which are identified by listing between brackets the substituted amino acids in single letter symbols followed by their position number in the mature staphylokinase sequence and by the substituting amino acids in single letter symbol; the column "Exp." indicates expression levels in mg/L, and the column "Spec. Act." indicates the specific activity in Home Units as defined in example 2. Indications "17G11", "26A2"etc. refer to monoclonal antibodies binding to the indicated epitopes I, II and III (22). Epitope I is recognized by the antibody cluster 17G11, 26A2, 30A2, 2B12 and 3G10, whereas epitope II is recognized by the antibody cluster 18F12, 14H5, 28H4, 32B2 and 7F10, and epitope III by the antibody cluster 7H11, 25E1, 40C8, 24C4 and 1A10. Human plasma "Pool" indicates a plasma pool from initially 16 and subsequently 10 patients immunized by treatment with SakSTAR, "Subpool B" indicates a plasma pool from three patients that absorbed less than 50% of the induced antibodies with SakSTAR(K35A,E38A,K74A,E75A,R77A) and "Subpool C" indicates a plasma pool from 3 patients that absorbed >90% of the induced antibodies with SakSTAR(K35A, E38A,K74A,E75A,R77A) (22). In tables 6, 7 and 8 an additional pool of plasma from 40 patients immunized by treatment with SakSTAR (Pool 40) was also used.

EXAMPLE 2

Construction, Epitope Mapping with Murine Monoclonal Antibodies and Absorption with Pooled Plasma of Immunized Patients, of "alanine-to-wild-type" Reversal Variants of "charged-cluster-to-alanine" Mutants of Staphylokinase As stated above, wild-type staphylokinase (SakSTAR variant (9)) contains three non-overlapping immunodominant epitopes, two of which can be eliminated by specific site-directed substitution of clusters of two (K35A,E38A or E80A,D82A) or three (K74A,E75A,R77A) charged amino acids with Ala (22). The combination mutants SakSTAR (K35A,E38A,K74A,E75A,R77A) in which Lys35, Glu38, Lys74, Glu75 and Arg77, and SakSTAR(K74A,E75A, R77A,E80A,D82A) in which Lys74, Glu75, Arg77, Glu80 and Asp82 were substituted with Ala (previously identified as SakSTAR.M3.8 and SakSTAR.M8.9, respectively (22)), were found to have a reduced reactivity with murine monoclonal antibodies against two of the three immunodominant epitopes and to absorb on average only ⅔ of the neutralizing antibodies elicited in 16 patients by treatment with wild-type SakSTAR (22). These mutants also induced less antibody formation than wild-type SakSTAR in experimental thrombolysis models in rabbits and baboons, and in patients with peripheral arterial occlusion (22). However, their specific activities were reduced to approximately 50% of that of wild-type SakSTAR, which would be of some concern with respect to the clinical use of these compounds.

In an effort to improve the activity and stability without loss of the reduced antibody recognition, the effect of a systematic reversal of one or more of these substituted amino acids to the wild-type residues was studied. Fourteen new mutants were constructed, purified and characterized in terms of specific activity, reactivity with the panel of murine monoclonal antibodies, and absorption of antibodies from plasma of patients treated with wild-type SakSTAR (Table 1). The present example thus focusses on reversal from alanine to the wild-type residue of one or more of the seven amino acids of SakSTAR listed above i.e. K35, E38, K74, E75, R77, E80 and D82.

Reagents and Methods

The source of all reagents used in the present study has previously been reported (22). Restriction enzymes were purchased from Pharmacia (Uppsala, Sweden) or Boehringer Mannheim (Mannheim, Germany). T4 DNA ligase, Klenow. Fragment of *E. coli* DNA polymerase I and alkaline phosphatase were obtained from Boehringer Mannheim. Enzyme reactions were performed using the conditions suggested by the suppliers. Plasmid DNA was isolated using a QIAGEN-purification protocol (provided by Westburg, Leusden, The Netherlands). pMEX.602sakB (i.e. pMEX.SakSTAR) was constructed as described elsewhere (23). SakSTAR, SakSTAR(K35A,E38A), SakSTAR(K74A, E75A,R77A), SakSTAR(E80A,D82A), SakSTAR(K35A, E38A,K74A,E75A,R77A) and SakSTAR(K74A,E75A, R77A,E80A,D82A) were produced and purified as described elsewhere (22). Transformations of *E. coli* were performed utilizing the calcium phosphate procedure. DNA sequencing was performed using the dideoxy chain termination reaction method and the Automated Laser fluorescent A.L.F.™ (Pharmacia). The chromogenic substrate (S2403) L-Pyroglutamyl-L-phenylalanyl-L-lysine-p-nitroanaline hydrochloride was purchased from Chromogenix (Belgium). $^{125}$I-labeled fibrinogen was purchased from Amersham (UK). All other methods used in the present example have been previously described (22,27).

Construction of Expression Plasmids

The plasmids encloding SakSTAR(K35A,E38A,K74A, E75A), SakSTAR(E38A,E75A,R77A), SakSTAR(E38A, E75A), SakSTAR(K35A,E75A,R77A), SakSTAR(K35A, E75A), SakSTAR(E80A), SakSTAR(D82A), SakSTAR (E75A,D82A), SakSTAR(K74A) and SakSTAR(E75A) were constructed by the spliced overlap extension polymerase chain reaction (SOE-PCR) (24), using Vent DNA polymerase (New England Biolabs, Leusden, The Netherlands), and available or generated sakSTAR variants as template. Two fragments were amplified by PCR, the first one starting from the 5' end of the staphylokinase gene with primer 5'-CAGGAAACAGAATTCAGGAG-3' (SEQ ID NO: 1) to the region to be mutagenized (forward primer), the second one from the same region (backward primer) to the 3' end of the staphylokinase gene with primer 5'-CAAAACAGCCAAGCTTCATTCATTCAGC-3' (SEQ ID NO: 2).

The plasmid encoding SakSTAR(E38A,K74A,E75A, R77A) was assembled by digestion of pMEX602sakB and pMEX.SakSTAR(K35A,E38A,K74A,E75A,R77A) with Bpm I which cuts between the codons for K35 and E38 of SakSTAR, and ligation of the required fragments. The plasmid encoding SakSTAR(K35A,K74A,E75A,R77A) was constructed by digestion of pMEX.SakSTAR(K35A,E38A, K74A,E75A,R77A) and pMEX.SakSTAR(K74A,E75A, R77A) with Bpm I and religation of the required fragments. The plasmids encoding SakSTAR(K35A,E38A,E75A, R77A) and SakSTAR(K35A,E38A,K74A,R77A) were constructed by two PCR using pMEX.SakSTAR(K35A,E38A, K74A,E75A,R77A) as template, followed by restriction ligation and recloning into pMEX602sakB.

Expression and Purification of SakSTAR Variants

The SakSTAR variants were expressed and purified, as described below, from transformed *E. coli* WK6 grown either in LB medium [SakSTAR(E38A,K74A,E75A,R77A), SakSTAR(K74A), SakSTAR(E75A) and SakSTAR(E75A, D82A)], or in terrific broth (TB) (28) medium [SakSTAR (K35A,K74A,E75A,R77A), SakSTAR(K35A,E38A,E75A, R77A), SakSTAR(K35A,E38A,K74A,R77A), SakSTAR (K35A,E38A,E75A), SakSTAR(E38A, E75A,R77A), SakSTAR(E38A,E75A), SakSTAR(K35A,E75A,R77A), SakSTAR(K35A, E75A), SakSTAR(E80A), and SakSTAR (D82A)].

For derivatives produced in LB medium, a 20 mL aliquot of an overnight saturated culture was used to inoculate a 2 L volume of LB medium containing 100 μg/mL ampicillin. After 3 hours incubation at 37° C., IPTG (200 μmol/L) was added to induce expression from the tac promoter. The production phase was allowed to proceed for 4 hours, after which the cells were pelleted by centrifugation at 4,000 rpm for 20 min, resuspended in 1/20 volume (100 mL) of 0.01 mol/L phosphate buffer pH 6.5 and disrupted by sonication at 0° C. Cell debris were removed by centrifugation for 20 min at 20,000 rpm and the supernatant, containing the cytosolic soluble protein fraction, was stored at −20° C. until purification.

For the derivatives produced in TB medium, a 4 mL aliquot of an overnight saturated culture in LB medium was used to inoculate a 2 L culture in terrific broth containing 100 μg/mL ampicillin. The culture was grown with vigorous aeration for 20 hours at 30° C. The cells were pelleted by centrifugation, resuspended in 1/10 volume (200 mL) of 0.01 mol/L phosphate buffer pH 6.5 and disrupted by sonication at 0° C. The suspension was then centrifuged for 20 min at 20,000 rpm and the supernatant was stored at −20° C. until purification. Cleared cell lysates containing the SakSTAR variants were subjected to chromatography on a 1.6×6 cm column of SP-Sephadex, followed by chromatography on a 1.6×5 cm column of Q-Sepharose [variants SakSTAR (E38A,K74A,E75A,R77A), SakS TAR(K35A,K74A,E75A, R77A), SakSTAR(K35A,E38A,E75A,R77A), SakSTAR (K35A,E38A,K74A,R77A) and SakSTAR(K35A,E38A, K74A,E75A)] or by chromatography on a 1.6×6 cm column of phenyl-Sepharose [variants SakSTAR(E35A,E38A, R77A), SakSTAR(E38A,E75A), SakSTAR(K35A,E75A, R77A), SakSTAR(K35A,E75A), SakSTAR(K74A), SakSTAR(E75A), SakSTAR(E80A), SakSTAR(D82A) and SakSTAR(E75A,D82A)]. The SakSTAR containing fractions, localized by SDS-gel electrophoresis, were pooled for further analysis.

Physicochemical and Biochemical Analysis

Protein concentrations were determined according to Bradford (29). The specific activities of SakSTAR solutions were determined with a chromogenic substrate assay carried out in microtiter plates using a mixture of 80 $\mu$L SakSTAR solution and 100 $\mu$L Glu-plasminogen solution prepared as described elsewhere (30) (final concentration 0.5 $\mu$mol/L). After incubation for 30 min at 37° C., generated plasmin was quantitated by addition of 20 $\mu$L S2403 (final concentration 1 mmol/L) and measurement of the absorption at 405 nm. The activity was expressed in home units (HU) by comparison with an in-house standard (lot STAN5) which was assigned an activity of 100,000 HU (100 kHU) per mg protein as determined by amino acid composition (7). SDS-PAGE was performed with the Phast System™ (Pharmacia, Uppsala, Sweden) using 10–15% gradient gels and Coomassie Brilliant blue staining. Reduction of the samples was performed by heating at 100° C. for 3 min in the presence of 1% SDS and 1% dithioerythritol. The specific activities of the different SakSTAR mutants determined with the chromogenic substrate assay are summarized in Table 1.

Binding to Murine Monoclonal Antibodies

In agreement with previous observations (22), SakSTAR (K74A,E75A,R77A) did not react with 4 of the 5 MAbs recognizing epitope I, whereas SakSTAR(K35A,E38A) did not react with 3 of the 5 and SakSTAR(E80A,D82A) not with 4 of the 5 Mabs recognizing epitope III. These reduced reactivities were additive in SakSTAR(K35A,E38A,K74A, E75A,R77A) and in SakSTAR(K74A,E75A,R77A,E80A, D82A). The reduced reactivity of SakSTAR(K74A,E75A, R77A) was fully maintained in SakSTAR(K35A,E38A, K74A,E75A) and in SakSTAR(K35A,E75A,R77A), largely in SakSTAR(K35A,E38A,E75A,R77A), SakSTAR(E38A, E75A,R77A), SakSTAR(E38A,E75A) and SakSTAR (E75A), but much less in SakSTAR(K35A,E38A,K74A, R77A) and SakSTAR(K74A), indicating that E75 is the main contributor to the binding of the 4 Mabs recognizing epitope I of SakSTAR. However, surprisingly, binding of epitope I antibodies to SakSTAR(E75A,D82A) was normal in two independent preparations from expression plasmids with confirmed DNA sequences. The reduced reactivity of the 3 MAbs of epitope III with SakSTAR(K35A,E38A) required both K35 and E38, as demonstrated with SakSTAR (E38A,K74A,E75A,R77A) and SakSTAR(K35A,K74A, E75A,R77A), with SakSTAR(E38A,E75A) and SakSTAR (K35A, E75A) and with SakSTAR(E38A,E75A,R77A) and SakSTAR(K35A,E75A,R77A). The reduced reactivity of the 4 MAbs of cluster III with SakSTAR(E80A,D82A) was maintained in SakSTAR(D82A) but not in SakSTAR (E80A).

Absorption of Antibodies, Elicited in Patients by Treatment with Wild-type SakSTAR Plasma samples from 16 patients with acute myocardial infarction, obtained several weeks after treatment with SakSTAR (4,31) were used. The staphylokinase-neutralizing activity in these samples was determined as follows. Increasing concentrations of wild-type or variant SakSTAR (50 $\mu$L volumes containing 0.2 to 1000 $\mu$g/mL) were added to a mixture of 300 $\mu$L citrated human plasma and 50 $\mu$L buffer or test plasma, immediately followed by addition of 100 $\mu$L of a mixture containing thrombin (50 NIH units/mL) and $CaCl_2$ (25 mmol/L). The plasma clot lysis time was measured and plotted against the concentration of SakSTAR moiety. From this curve the concentration of staphylokinase moiety that produced complete clot lysis in 20 min was determined. The neutralizing activity titer was determined as the difference between the test plasma and buffer values and was expressed in $\mu$g per mL test plasma. The results of the individual patients have been reported elsewhere (22). For the present invention, three plasma pools were made, one from 10 patients from whom sufficient residual plasma was available, one from three patients that absorbed less than 50% of the antibodies with SakSTAR(K35A,E38A,K74A, E75A,R77A) (Subpool B) and one from three patients that absorbed >90% of the antibodies with SakSTAR(K35A, E38A,K74A,E75A, R77A) (Subpool C).

These plasma pools were diluted (1/30 to 1/200) until their binding to SakSTAR substituted chips in the BIAcore instrument amounted to approximately 2000 RU. From this dilution a calibration curve for antibody binding was constructed using further serial two-fold dilutions. The plasma pools were absorbed for 10 min with 100 mmol/L of the SakSTAR variants, and residual binding to immobilized SakSTAR was determined. Residual binding was expressed in percent of unabsorbed plasma, using the calibration curve.

The results are summarized in Table 1. Whereas wild-type SakSTAR absorbed more than 95% of the binding antibodies from pooled plasma of the 10 patients, incomplete absorption (<60%) was observed with SakSTAR(K74A, E75A,R77A), SakSTAR(K35A,E38A,K74A, E75A,R77A), SakSTAR(E38A,K74A,E75A,R77A), SakSTAR(K35A, K74A,E75A,R77A), SakSTAR(K35A,E38A,K74A,R77A), SakSTAR(K35A,E38A,K74A,E75A), SakSTAR(K74A) and SakSTAR(K74A,E75A,R77A,E80A,D82A) but absorption was nearly complete with SakSTAR(K35A,E38A), SakSTAR(K35A,E38A,E75A,R77A), SakSTAR(E38A, E75A,R77A), SakSTAR(E38A,E75A), SakSTAR(K35A, E75A,R77A), SakSTAR(K35A,E75A), SakSTAR(E75A), SakSTAR(E80A,D82A), SakSTAR(E80A), SakSTAR (D82A) and SakSTAR(E75A,D82A). These results, surprisingly, demonstrate that approximately 40% of the antibodies elicited in patients by treatment with wild-type SakSTAR depend on K74 for their binding (Table 1). Absorption with pooled plasma from 3 patients from which <50% of the antibodies were absorbed with SakSTAR (K35A,E38A,K74A,E75A,R77A) (Subpool B) confirmed the predominant role of K74 for antibody recognition. As expected, absorption with pooled plasma from 3 patients from which >95% of the antibodies were absorbed with SakSTAR(K35A,E38A,K74A,E75A,R77A) (Subpool C) was nearly complete with all variants tested.

EXAMPLE 3

Comparative Thrombolytic Efficacy and Immunogenicity of SakSTAR(K74A,E75A,R77A) and SakSTAR(K74A) Versus SakSTAR in Patients with Peripheral Arterial Occlusion Purification of SakSTAR(K74A,E75A,R77A) and SakSTAR(K74A) for Use in Vivo A 12 to 24 L culture (in 2 L batches) of the variants SakSTAR(K74A,E75A,R77A), or of SakSTAR(K74A) was grown and IPTG-induced in LB medium supplemented with 100 $\mu$g/mL ampicillin, pelleted, resuspended, disrupted by sonication and cleared as described above. The compounds were purified by chromatography on a 5×20 cm column of SP-Sephadex, a 5×10 cm column of Q-Sepharose and/or a 5×13 cm column of phenyl-Sepharose using buffer systems described elsewhere (22,23). The materials were then gel filtered on sterilized Superdex 75 to further reduce their endotoxin content. The SakSTAR variant containing fractions were pooled, the protein concentration was adjusted to 1 mg/mL and the material sterilized by filtration through a 0.22 $\mu$m Millipore filter. The methodology used to determine the biological properties of the final material required for use in vivo is described above and elsewhere (22).

Materials and Methods

Staphylokinase-neutralizing activity in plasma was determined as described above. Quantitation of antigen-specific IgG and IgM antibodies was performed using enzyme-linked immunosorbent assays in polystyrene microtiter plates essentialy as described previously (22). In the IgG assays, dilution curves of affinospecific anti-SakSTAR IgG antibodies were included on each plate. These antibodies were isolated from plasma obtained from 3 patients, after thrombolytic therapy with wild-type SakSTAR, by chromatography on protein A-Sepharose and on insolubized SakSTAR, and elution of bound antibodies with 0.1 mol/L glycine-HCl, pH 2.8. The purity of the IgG preparation was confirmed by sodium dodecylsulfate polyacrylamide gel electrophoresis. In the IgM assays, titers defined as the plasma dilution giving an absorbancy at 492 nm equivalent to that of a 1/640 dilution of pooled plasma were determined and compared with the titer of baseline samples before treatment (median value 1/410, interquartile range 1/120–1/700).

Thrombolytic Efficacy

Wild-type SakSTAR or the variants SakSTAR(K74A) or SakSTAR(K74A,E75A,R77A) were administered intra-arterially at or in the proximal end of the occlusive thrombus as a bolus of 2 mg followed by an infusion of 1 mg/hr (reduced overnight in some patients to 0.5 mg/hr) in groups of 6 to 12 patients with angiographically documented occlusion of a peripheral artery or bypass graft of less than 120 days duration. Patients were studied after giving informed consent, and the protocol was approved by the Human Studies Committee of the University of Leuven. Inclusion and exclusion criteria, conjunctive antithrombotic treatment (including continuous intravenous heparin) and the study protocol were essentially as previously described (22).

Relevant baseline characteristics of the individual patients are shown in Table 2. The majority of PAO were at the femoropopliteal level. Two iliac stent and 8 graft occlusions were included. Eight patients presented with incapacitating claudication, 5 with chronic ischemic rest pain, 7 with subacute ischemia and 7 with acute ischemia. One patient (POE) who had 2 years previously been treated with SakSTAR was included in the SakSTAR(K74A) group. This patient was not included in the statistical analyses.

Table 2 also summarizes the individual treatment and outcome. Intra-arterial infusion, at a dose of 6.0 to 25 mg and a duration of 4.0 to 23 hrs, induced complete recanalization in 24 patients and partial recanalization in 3. Complementary endovascular procedures (mainly PTA) were performed in 17 patients and complementary reconstructive vascular surgery following thrombolysis in 3. No patient underwent major amputation. Early recurrence of thrombosis after the end of the angiographic procedure occurred in 4 patients. Bleeding complications were absent or limited to mild to moderate hematoma formation at the angiographic puncture sites except for 5 patients who required transfusion (data not shown). Intracranial or visceral hemorrhage was not observed. Circulating fibrinogen, plasminogen and $\alpha$2-antiplasmin levels remained essentially unchanged during infusion of the SakSTAR moieties (data not shown), confirming absolute fibrin specificity of staphylokinase at the dosages used. Significant in vivo fibrin digestion occurred as evidenced by elevation of fibrin fragment D-dimer levels. Intra-arterial heparin therapy prolonged aPTT levels to a variable extent (data not shown).

Antibody Induction

Figure 2:
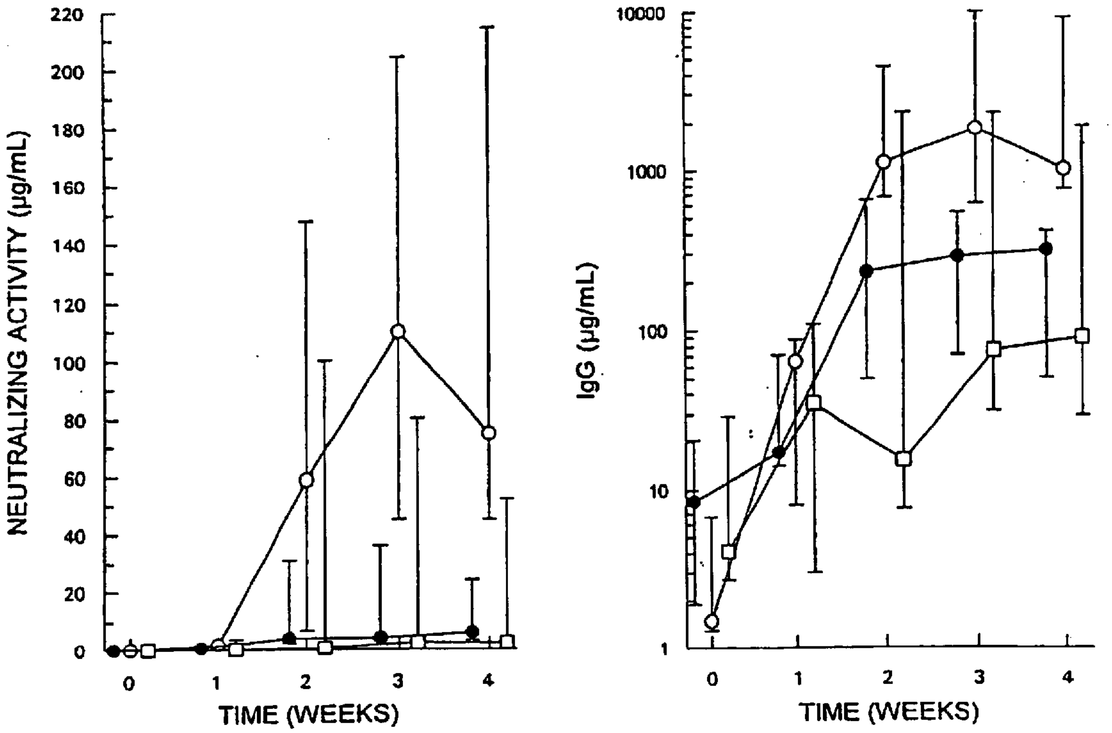
FIG. 2 is a time course of neutralizing activities (left panel) and specific IgG against administered agent (right panel) following intra-arterial infusion of SakSTAR (open circles, n=9), SakSTAR (K74A) (closed circles, n=11) or SakSTAR (K74A,E75A,R77A) (open squares, n–6) in patients with peripheral arterial occlusion. The data represent median values and interquartile ranges, in μg/ml.

Antibody-related SakSTAR-, SakSTAR(K74A)- and SakSTAR(K74A,E75A,R77A)-neutralizing activity and anti-SakSTAR, anti-SakSTAR(K74A) and anti-SakSTAR (K74A) and anti-SakSTAR(K74A,E75A,R46177A) IgG, were low at baseline and during the first week after the infusion (FIG. 2). From the second week on, neutralizing activity levels increased to reach median values at 3 to 4 weeks of 20 $\mu$g SakSTAR(K74A) and 2.4 $\mu$g SakSTAR (K74A,E75A,R77A) neutralized per mL plasma in the patients treated with SakSTAR(K74A) and SakSTAR (K74A,E75A,R77A), respectively, which is significantly lower than the median value of 93 $\mu$g wild-type SakSTAR neutralized per mL in the patients treated with SakSTAR (p=0.024 for differences between the three groups by Kruskal-Wallis analysis and p=0.01 and p=0.036, respectively, for variants vs wild-type by Mann-Whitney rank sum test). The levels of anti-SakSTAR(K74A) and of anti-SakSTAR(K74A,E75A,R77A) IgG increased to median values at 3 to 4 weeks of 270 and 82 $\mu$g/mL plasma in patients treated with SakSTAR(K74A) and SakSTAR (K74A,E75A,R77A) respectively, which is significantly lower than the median value of 1800 $\mu$g anti-SakSTAR per mL plasma in the patients treated with SakSTAR ((p=0.024 for differences between the three groups by Kruskal-Wallis analysis and p=0.007 and 0.05, respectively, for variants versus wild-type by Mann-Whitney rank sum test).

The titers of anti-SakSTAR(K74A) and of anti-SakSTAR (K74A,E75A,R77A) IgM increased from median baseline values of 1/460 and 1/410 to median values at 1 week of 1/510 and 1/450 in patients treated with SakSTAR(K74A) and SakSTAR(K74A,E75A,R77A), respectively, which was not significantly different from the median values of 1/320 at baseline and 1/640 at week 1 in patients treated with SakSTAR. Corresponding values at 2 weeks were 1/590 and 1/550 in patients given SakSTAR(K74A) and SakSTAR (K74A,E75A,R77A), not significantly different from 1/930 with SakSTAR (data not shown).

The antibodies induced by treatment with SakSTAR were completely absorbed by SakSTAR but incompletely by SakSTAR(K74A) and by SakSTAR(K74A,E75A,R77A) confirming the immunogenicity of the K74,E75,R77 epitope and the dominant role of K74 in the binding of antibodies directed against this epitope. The antibodies induced by treatment with SakSTAR(K74A) or SakSTAR(K74A,E75A,R77A) were completely absorbed by SakSTAR, by SakSTAR(K74A) and by SakSTAR(K74A,E75A,R77A), indicating that immunization was not due to neoepitopes generated by substitution of Lys74 with Ala, but to epitopes different from the K74,E75,R77 epitope.

Thus, this example illustrates that staphylokinase variants with reduced antibody induction but intact thrombolytic potency can be generated. The present experience in 26 patients treated with SakSTAR (n=9), SakSTAR(K74A) (n=11) and SakSTAR(K74A,E75A,R77A) (n=6) combined with previous experience in 14 patients with SakSTAR (n=7) and SakSTAR(K35A,E38A,K74A,E75A,R77A) (n=7) (31) and in 24 patients with SakSTAR (32), and with subsequent non-randomized experience in patients with SakSTAR (n=30) with SakSTAR(K74A) (n=12) and with SakSTAR(K74A,E75A,R77A) (n=7) (data not shown), allows an initial estimation of the prevalence of immunization by intra-arterial treatment with SakSTAR or variants with an altered K74,E75,R77 epitope [SakSTAR(K74A), SakSTAR(K74A,E75A,R77A) and SakSTAR(K35A,E38A, K74A,E75A, R77A)]. Neutralizing activity data after 2 to 4 weeks, available in 70 patients with peripheral arterial occlusion given intra-arterial SakSTAR, revealed that 56 patients (80 percent) had levels >5 μg compound neutralized per mL plasma. Of the patients given SakSTAR(K74A), SakSTAR(K74A,E75A,R77A) or SakSTAR(K74A,E75A, K74A,E75A,R77A), 27 of the 43 (63 percent) had neutralizing activity levels of >5 μg compound per mL plasma. This difference is statistically significant (p=0.05 by Fisher's exact test) indicating that the K74,E75,R77 epitope is a major determinant of antibody induction. However, the residual prevalence of specific immunocompetence against SakSTAR(K74A) indicates that additional mutagenesis to further reduce the immunogenicity of SakSTAR variants for clinical use, would be desirable.

EXAMPLE 4

Construction, Epitope Mapping with Murine Monoclonal Antibodies and Absorption with Pooled Plasma of Immunized Patients, of Alanine-substitution Mutants of Staphylokinase Site-directed mutagenesis was applied to residues other than "charged amino acids" in order to identify i) additional residues belonging to epitopes I and III identified with the panel of murine Mabs and ii) amino acids determining absorption to antiserum from immunized patients. Since functional epitopes generally comprise more than one amino acid residue critical for antibody binding, identification of additional residues in these epitopes could lead to the construction of new combination derivatives displaying a lower antigenic profile, while keeping the specific activity and the temperature stability of wild-type staphylokinase.

In this example, the construction and characterization of SakSTAR variants in which one or at most two amino acids (adjacent or in close vicinity) were substituted with alanine is described. The mutants described under this example are listed in Table 3. These variants were expressed in *E. coli*, purified and characterized in terms of specific activity, reactivity with the panel of murine monoclonal antibodies, and absorption of antibodies from plasma of patients treated with wild-type SakSTAR.

Reagents and Methods

The source of all reagents used in the present study has previously been reported (22), or is specified below, The template vector for mutagenesis, pMEX602sakB (i.e. pMEX.SakSTAR), has been described elsewhere (23). Restriction and modification enzymes were purchased from New England Biolabs (Leusden, The Netherlands), Boehringer Mannheim (Mannheim, Germany) or Pharmacia (Uppsala, Sweden). The enzymatic reactions were performed according to the supplier recommendation. The mutagenic oligonucleotides and primers were obtained from Eurogentec (Seraing, Belgium). Plasmid DNA was isolated using a purification kit from Qiager (Hilden, Germany) or the BIO 101 RPM kit (Vista, Calif.), as recommended. Transformation-competent *E. coli* cells were prepared by the well-known calcium phosphate procedure. Nucleotide sequence determination was performed on double strand plasmid DNA with the dideoxy chain termination method, using the T7 sequencing kit (Pharmacia, Uppsala, Sweden). Polymerase chain reactions (PCR) were performed using Taq polymerase from Boehringer Mannheim (Mannheim, Germany) or Vent polymerase (New England Biolabs, Leusden, The Netherlands). The recombinant DNA methods required to construct the variants described in this example are well established (22,27).

Construction of Expression Plasmids

The variants SakSTAR(Y17A,F18A), SakSTAR(F104A), SakSTAR(F111A), SakSTAR(Y9A), SakSTAR(Y91A), SakSTAR(Y92A), SakSTAR(187A), SakSTAR(I106A) and SakSTAR(I120A) were constructed with the Chameleon Double-Stranded Site-Directed Mutagenesis kit from Stratagene (La Jolla, USA), using the pMEX.SakSTAR vector as tmplate, and following instructions of the supplier. The mutagenic oligonucleotides (not shown) were used in combination with the selection-primer LY34 5' CAAAACAGCCGAGCTTCATTCATTCAGC (SEQ ID NO: 3), which destroys the unique HindIII site located 3' to the staphylokinase encoding gene in pMEX.SakSTAR and allows to counter-select the non-mutant progeny by HindIII digestion. The deletion of the HindIII site was in most cases correlated with the presence of the desired mutation introduced by the mutagenic oligonucleotide. The variant SakSTAR(I133A), was constructed by performing a polymerase chain reaction on the pMEX.SakSTAR plasmid using the primer 818A located at the 5' end of the sakSTAR gene (5' CAGGAAACAGAATTCAGGAG) (SEQ ID NO: 1) and the mutagenic primer LY58(5' TTCAGCATGCTGCAGTTATTTCTTTTCTGCAACAACC TTGG)(SEQ ID NO: 4). The amplified product (30 cycles: 30 sec at 94° C., 30 sec at 50° C., 30 sec at 72° C.) was purified, digested with EcoRI and PstI, and ligated into the corresponding sites of pMEX-SakSTAR.

The variants SakSTAR(I1128A), SakSTAR(L127A) and SakSTAR(N126V) were constructed by performing a polymerase chain reaction using the primer 818A located at the 5' end of the sakSTAR gene and mutagenic primers (not shown). The amplified product (30 cycles: 1 sec at 94° C., 1 sec at 50° C., 10 sec at 72° C.) was purified, digested with EcoRI and StyI, and ligated into the corresponding sites of pMEXSakSTAR. The variant SakSTAR(F125A) was constructed by performing two consecutive PCR reactions (30 cycles: : 30 sec at 94° C., 30 sec at 50° C., 30 sec at 72° C.). In the first reaction, a fragment of pMEX.SakSTAR was amplified with the primers 818A and a mutagenic primer. This amplified fragment was then used as template in a second PCR reaction with a mutagenic primer in order to further elongate the fragment downstream of the StyI site present in the sakSTAR gene (corresponding to amino acids 130–131 of SakSTAR). The resulting product was digested with EcoRI and StyI, and ligated into the corresponding sites of pMEXSakSTAR.

The plasmids encoding all the other variants listed in table 3 were contructed by direct PCR or by the spliced overlap extension polymerase chain reaction (SOE-PCR)(24) using pMEX.SakSTAR or available plasmids encoding SakSTAR variants as template. Two fragments were amplified by PCR (30 cycles: 1 sec at 94° C., 1 sec at 50° C., 10 sec at 72° C.), the first one starting from the 5' end (primer 818A) of the *staphylokinase* gene to the region to be mutagenized (forward primer), the second one from this same region (backward primer) to the 3' end of the gene with primer 818D (5' CAAACAGCCAAGCTTCATTCATTCAC) (SEQ ID NO: 5). The forward and backward primers shared an overlap of around 24 bp (primers not shown). The two purified fragments were then assembled together in a second PCR reaction with the external primers 818A and 818D (30 cycles: 1 sec at 94° C., 1 sec at 50° C., 10 sec at 72° C.). The amplified product from this final reaction was purified, digested with EcoRI and HindII and ligated into the corresponding site of pMEX.SakSTAR. For each construction, the sequence of the variant was confirmed by sequencing the entire SakSTAR coding region.

Expression and Purification of SakSTAR Variants

The SakSTAR variants were expressed and purified, as described below, from transformed *E. coli* grown in terrific broth (TB) medium (28). A 2 to 4 mL aliquot of an overnight saturated culture in LB medium was used to inoculate a 1 to 2 L culture in terrific broth supplemented with 100 μg/mL ampicillin. The culture was incubated with vigorous aeration and at 30° C. After about 16 hours incubation, IPTG (200 μmol/L) was added to the culture to induce expression from the tac promoter. After 3 hours induction, the cells were pelleted by centrifugation at 4,000 rpm for 20 min, resuspended in 1/10 volume of 0.01 mol/L phosphate buffer pH 6–6.5 and disrupted by sonication at 0C. The suspension was centrifuged for 20 min at 20,000 rpm and the supernatant was stored at 4° C. or at −20° C. until purification. The material was purified essentially as described above (Example 2): cleared cell lysates containing the SakSTAR variants were subjected to chromatography on a 1.6×5 cm column of SP-Sephadex, followed by chromatography on a 1.6×8 cm column of phenyl-Sepharose. The SakSTAR containing fractions, localized by SDS-gel electrophoresis, were pooled for further analysis.

Physicochemical and Biochemical Analysis

Protein concentrations were determined according to Bradford (29). SDS-PAGE was performed with the Phast System™ (Pharmacia, Uppsala, Sweden) using 10–15% gradient gels and Coomassie Brillant blue staining, and the specific activities of SakSTAR solutions were determined with a chromogenic substrate assay carried out in microtiter plates (as described in example 2). The specific activity of the different SakSTAR variants are summarized in Table 3.

Reactivity of SakSTAR Variants with a Panel of Murine Monoclonal Antibodies

The methodology used to determine the reactivity of the SakSTAR variants with a panel of murine monoclonal antibodies was described in example 1 above. The results are summarized in Table 3 (the layout of this Table corresponds to the layout of Table 1, as described in example 1). Apparent association constants at least 10-fold lower than those of wild-type staphylokinase were considered as significant and are indicated in bold type in the table.

Figure 3:
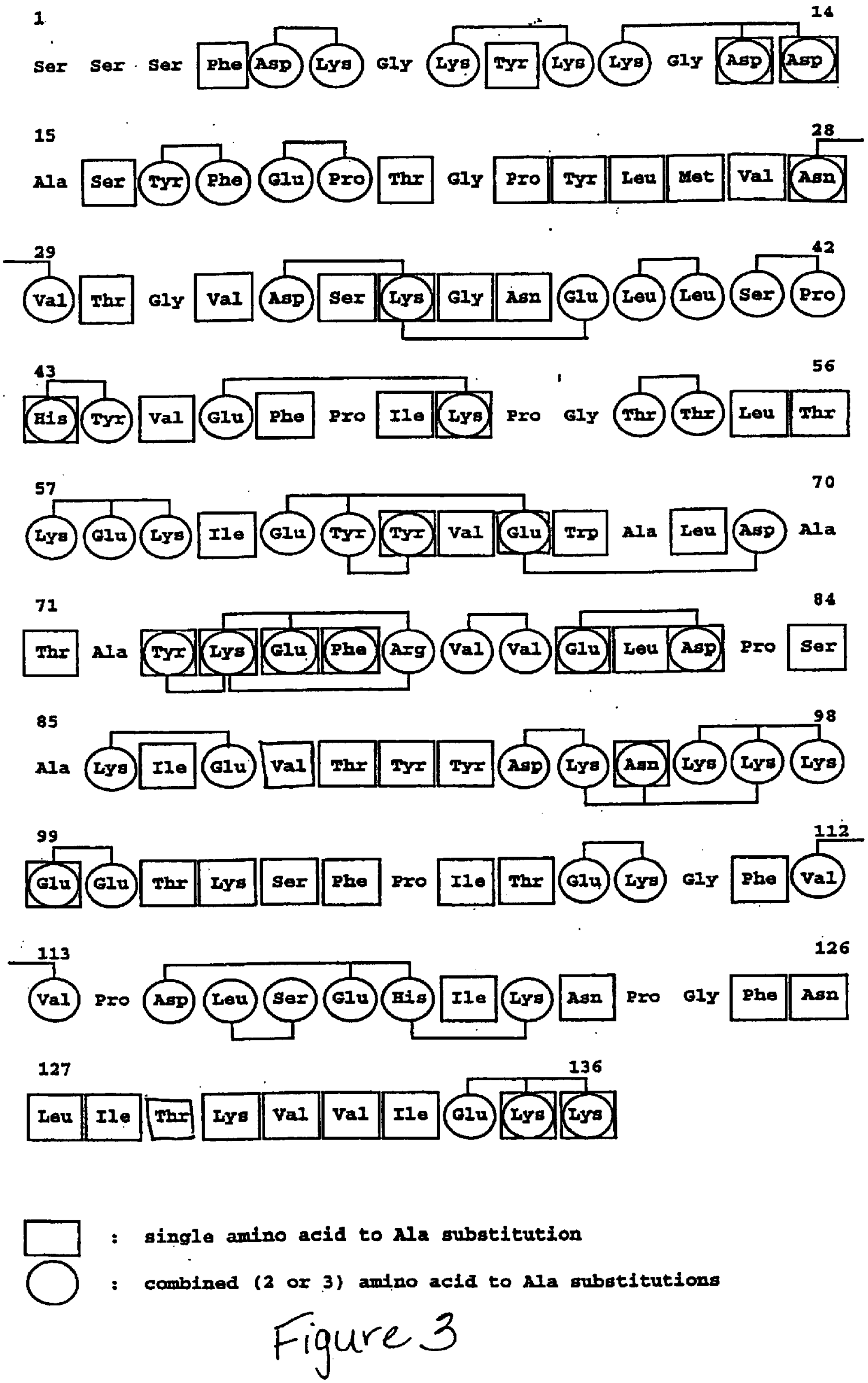
FIG. 3 is a protein sequence of wild-type staphylokinase, SakSTAR with indicated amino acid substitutions.

In order to obtain a comprehensive inventory of the properties of Ala-substitution variants of the SakSTAR molecule, 67 plasmids encoding variants with substitution of a single or two adjacent amino acids with Ala were constructed, expressed and purified. Together with the 35 charged residue to Ala-substitution variants previously described (22, and example 2), this analysis covers all residues in SakSTAR except Gly, Ala and Pro, as illustrated in FIG. 3. Eight of the variants could not be obtained in purified form, primarily as a result of low expression levels, 11 variants were inactive, 56 had a reduced specific activity, and 27 had a maintained or increased specific activity (≧100 kHU/mg). The yields of purified material from cultures of expressed plasmids were 16 mg/L (median, 10 to 90 percentile range 4 to 41 mg/L). SDS polyacrylamide gel electrophoresis consistently showed one main band with $M_r$≈16,000, usually representing ≧95% of total protein (not shown.).

Substitution of K35, N95, S 103 or K135 with Ala yielded variants with specific activities of ≧200 kU/mg. Substitution of W66, Y73 or E75 with Ala reduced the reactivity of the variants with >3 antibodies of epitope cluster I, of H43 or V45 with Ala that with 3 antibodies from epitope cluster II and of V32, K35, D82 and K130 with Ala that with >3 antibodies of epitope cluster III.

Absorption of Antibodies, Elicited in Patients by Treatment with SakSTAR

For the present example, the three plasma pools, as described in example 2 were used. The methodology used to evaluate the absorption with wild-type staphylokinase and with SakSTAR variants, of antibodies elicited in patients treated with SakSTAR, is described in detail in example 2. The results are summarized in Table 3. Whereas wild-type SakSTAR and most of the variants analyzed in this example absorbed more than 95% of the binding antibodies from pooled plasma of the 10 patients, incomplete absorption (<60%) was observed with SakSTAR(Y73A), and with SakSTAR(K74A). The predominant role of Lys74 for antibody recognition has been demonstrated previously (see example 2). The present results indicate that Tyr73 participates to the same major epitope as Lys74, or, alternatively, that substitution at Tyr73 may indirectly induce a structural modification of the "K74-epitope". Absorption with pooled plasma from 3 patients from which >95% of the antibodies were absorbed with SakSTAR(K35A,E38A,K74A,E75A,R77A) (Subpool C, see example 2) was nearly complete with most variants tested.

EXAMPLE 5

Construction, Epitope Mapping with Murine Monoclonal Antibodies and Absorption with Pooled Plasma of Immunized Patients, of Staphylokinase Variants with Substitution of S34, G36 and/or H43

The natural variant Sak42D differs from SakSTAR in three amino acids and corresponds to SakSTAR(S34G,G36R,H43R). Sak42D is characterized by reduced reactivity with some murine antibodies of epitope clusters II and III and a slightly reduced absorption of antibodies from plasma of patients treated with SakSTAR (Table 4). Mutagenesis of these residues in SakSTAR revealed that the reduced reactivity with epitope cluster III and with immunized patient plasma could be ascribed to the G36R substitution, the H43R substitution mediated the reduced reactivity with epitope cluster II but had no effect on the reactivity with immunized patient plasma, whereas the S34A substitution had no effect. The G36R substitution could be combined with the K74R but not with the K74A substitution, without significant reduction of the specific activity (Table 4).

EXAMPLE 6

Construction, Epitope Mapping with Murine Monoclonal Antibodies and Absorption with Pooled Plasma of Immunized Patients, of Staphylokinase Variants with Substitution of K35, E65, Y73, K74, E80+D82, N95, K130, V132 and/or K135

Based on the results of the alanine-substitution analysis in example 4, K35, N95 and K135 were selected for further analysis because SakSTAR(K35A), SakSTAR(N95A) and SakSTAR(K135A) had a two-fold increased specific activity, Y73 and K74 because SakSTAR(Y73A) and SakSTAR(K74A) had a markedly reduced reactivity with antibodies from epitope cluster I and diminished absorption of antibodies from plasma of patients immunized by treatment with SakSTAR, and K35, E80+D82, K130 and V132 because SakSTAR(K35A), SakSTAR(E80A,D82A), SakSTAR(K130A) and SakSTAR(V132A) had a reduced reactivity with antibodies from epitope cluster III.

In an effort to maximize the activity/antigenicity ratio, these amino acids were substituted with other amino acids than Ala. As summarized in Table 5, substitution of K35 with A, E or Q revealed that SakSTAR(K35A) had the most interesting properties, substitution of Y73 with F, H, L, S or W did not rescue the marked reduction in specific activity, and K74 confirmed its key role in binding of antibodies from immunized patient plasma, the best specific activity/antigenicity ratios being obtained with SakSTAR(K74Q) and SakSTAR(K74R). SakSTAR(E80A,D82A) was preferred over the single residue variants SakSTAR(E80A) or SakSTAR(D82A) because of its somewhat lower reactivity with immunized patient plasma. SakSTAR(N95A) could not be further improved by substitution of N95 with E, G, K or R and it was unable to confer its increased specific activity to variants containing K74A or K135R. Finally SakSTAR (K130A) was outperformed in terms of specific activity by SakSTAR(K130T) and SakSTAR(V132A) by SakSTAR (V132R).

EXAMPLE 7

Construction, Epitope Mapping with Murine Monoclonal Antibodies and Absorption with Pooled Plasma of Immunized Patients of Combination Variants of SakSTAR(K130T,K135R) and SakSTAR(E80A, D82A,K130T,K135R) with K35A,G36R,E65X,K74X and Selected Other Amino Acids In the present and the following examples an additional plasma pool was made from 40 patients obtained several weeks after treatment with SakSTAR (Pool 40). The original pool from 10 patients is further identified as Pool 10. The absorption of staphylokinase-specific antibodies was quantified as described above and elsewhere (22).

The SakSTAR(K130T,K135R) variant was taken as a template for additive mutagenesis because of its high specific activity with a moderate reduction of binding to antibodies of epitope cluster III and absorption of antibodies from immunized patient plasma (Table 6). Addition of G36R, K74R, or K74Q or both to the template did not markedly reduce the specific activity, reduced the reactivity with monoclonal antibodies against epitope cluster III (G36R substitution) and decreased the absorption of antibodies from immunized patient plasma (K74R or K74Q substitution). Combination of E65A or E65Q with K74Q in the SakSTAR(K130T,K135R) template reduced the absorption of antibodies from Pool 10 and Pool 40 to around 50 and 60 percent respectively, without markedly reducing the specific activity. Addition substitution of selected amino acids in the SakSTAR(E65Q,K74Q,K130T,K135R) template did not further reduce the antibody absorption from Pool 10 or Pool 40. Surprisingly, the substitution of K136 with A and the addition of K in position 137 resulted in a marked increase in specific activity, as measured in the chromogenic substrate assay.

Combination of the SakSTAR(E80A,D82A) and SakSTAR(K130T,K135R) templates, did not affect the specific activity and had a reduced reactivity with epitope cluster III antibodies (Table 7). Therefore the SakSTAR (E80A,D82A,K130T,K135R) template was selected for further mutagenesis. Addition of K74R and even more of K74Q drastically reduced the reactivity with immunized patient plasma. Finally, addition of E65D or of K35A or E65S to the SakSTAR(K74R,E80A,D82A,K130T,K135R) or SakSTAR (K74Q,E80A,D82A,K130T, K135R) templates yielded variants with intact specific activity which only bound ≦45 of the antibodies of pooled immunized patient plasma and less than 15 percent of the subpool reacting for more than 50 percent with the K74,E75,R77 epitope.

EXAMPLE 8

Characterization of Selected Variants of Staphylokinase with Intact Specific Activity and Less Than 50% Adsorption of Pooled SakSTAR Specific Human Antibodies Elicited in Patients by Treatment with Wild-type SakSTAR.

Twenty three of the variants constructed and characterized in the above examples combined the properties of a residual specific activity of ≧100 kHU/mg and ≦50 percent absorption with the pool of antisera obtained from 10 patients treated with wild-type SakSTAR. The results are summarized in Table 8. Results obtained with Subpool B and Subpool C and with the pool of 40 patients treated with wild-type SakSTAR are included. SakSTAR(K74Q,E80A, D82A,K130T,K135R), SakSTAR(E65D,K74R,E80A, D82A,K130T, K135R), SakSTAR(K35A,E65D,K74Q, E80A,D82A,K130T,K135R) and SakSTAR(E65Q, K74Q, N95A,E118A,K130A,K135R,K136A,+137K) were selected for further characterization.

Fibrinolytic Properties of SakSTAR Variants in Human Plasma in Vitro

The fibrinolytic and fibrinogenolytic properties of the SakSTAR variants were determined as previously described. Dose- and time-dependent lysis of $^{125}$I -fibrin labeled human plasma clots submerged in human plasma was obtained with the selected variants (Table 9). Spontaneous clot lysis during the experimental period was ≦5% (not shown). Equi-effective concentrations of test compound (causing 50% clot lysis in 2 hrs; $C_{50}$), determined graphically from plots of clot lysis at 2 hrs versus the concentration of plasminogen activator (not shown), ranged from 0.11±0.01 to 0.24±0.04 μg/mL at which the residual fibrinogen levels ranges between 92±30 and 97±30 percent of baseline (Table 9). The concentrations of compound causing 50% fibrinogen degradation in 2 hrs in human plasma in the absence of fibrin were determined graphically from dose-response curves (not shown). These values (mean±SD of 3 independent experiments) ranged from 14±3.2 to 29±3.1 μg/mL (Table 9). Surprisingly the very high specific activity of SakSTAR (E65Q,K74Q,N95A,E118A, K130A,K135R,K136A,+137K) in the chromogenic assay was not associated with an increased thrombolytic potency in a plasma milieu.

Temperature Stability of Selected SakSTAR Variants

The temperature stability of preparations of SakSTAR (K74Q,E80A,D82A,K130T,K135R), SakSTAR(E65D, K74R,E80A,D82A,K130T,K135R) and SakSTAR(K35A, E65D,K74Q, E80A,D82A,K130T,K135R), dissolved to a concentration of 1.0 mg/mL in 0.15 mol/L NaCl, 0.01 mol/L phosphate buffer, pH 7.5 at various temperatures is illustrated in FIG. 4. At temperatures up to 37° C., all compounds remained fully active for up at least three days. At 56° C. and 70° C. the three variants were however less stable than wild-type SakSTAR.

Pharmacokinetic Properties of SakSTAR Variants Following Bolus Injection in Hamsters The pharmacokinetic parameters of the disposition of SakSTAR variants from blood were evaluated in groups of 4 hamsters following intravenous bolus injection of 100 μg/kg SakSTAR variant. SakSTAR-related antigen was assayed using the ELISA described elsewhere. The ELISA was calibrated against each of the SakSTAR variants to be quantitated. Pharmacokinetic parameters included: initial half-life (in min), $t½\alpha=\ln2/\alpha$; terminal half-life (in min), $t½\beta=\ln2/\beta$; volume of the central (plasma) compartment (in mL), $V_C$=dose/(A+B); area under the curve (in μg.min.m $L^{-1}$), AUC=A/α+B/β; and plasma clearance (in mL.min$^{-1}$), Clp=dose/AUC (33).

The disposition rate of staphylokinase-related antigen from blood following bolus injection of 100 μg/kg of the selected SakSTAR variants in groups of 4 hamsters could adequately be described by a sum of two exponential terms by graphical curve peeling (results not shown), from which the pharmacokinetic parameters summarized in Table 10 were derived. The pharmacokinetic parameters of the mutants were not markedly different from those of wild type SakSTAR. Initial plasma half-lives (t½(α)) ranged between 2.0 and 3.2 min and plasma clearances (Clp) between 1.6 and 4.1 mL/min.

EXAMPLE 9

Comparative Thrombolytic Efficacy and Immunogenicity of SakSTAR(K74Q, E80A,D82A,K130T,K135R) and SakSTAR(E65D,K74R, E80A,D82A,K130T,K135R) Versus SakSTAR in Patients with Peripheral Arterial Occlusion Purification for Use in Vivo Eighteen liter cultures (in 2 L batches) of the variants SakSTAR(K74Q,E80A,D82A,K130T, K135R) and SakSTAR(E65D,K74R,E80A,D82A, K130T,K135R) were grown for 20 hours in terrific broth medium (28), supplemented with 100 μg/mL ampicillin and induced with IPTG during the last 3 hours. The cells were pelleted, resuspended in 1/10 volume of 0.01 mol/L phosphate buffer, pH 6.0, disrupted by sonication and cleared by centrifugation. The compounds were purified by chromatography on a 10×7 cm column of SP-Sepharose, equilibrated with 0.01 mol/L phosphate buffer, pH 6.0 and eluted with a 1 mol/L NaCl gradient (3 column volumes). The fractions containing SakSTAR variant were pooled, solid NaCl was added to a concentration of 2.5 mol/L and the material was chromatographed on a 10×20 cm column of phenyl-Sepharose followed by stepwise elution with 0.01 mol/L phosphate buffer, pH 6.0. The materials were desalted on a 10×45 cm column of Sephadex G25, concentrated by application on a 5×10 cm column of SP-Sepharose with stepwise elution with 1.0 mol/L NaCl and finally gel filtered on a 6×60 cm column of Superdex 75 equilibrated with 0.15 m NaCl, 0.01 mol/L phosphate buffer, pH 7.5 to further reduce their endotoxin content. The SakSTAR variant containing fractions were pooled, the protein concentration was adjusted to 1 mg/mL and the material sterilized by filtration through a 0.22 μm Millipore filter. The methodology used to determine specific activity, endotoxin contamination, bacterial sterility and toxicity in mice is described above and elsewhere (22). The purity of the preparation was evaluated by SDS gel electrophoresis on 10% gels to which 40 μg of compound was applied.

Out of culture volumes of 18 liters of SakSTAR variant, 840 mg of SakSTAR(K74Q,E80A,D82A,K130T,K135R) with a specific activity of 140 kHU/mg and 800 mg SakSTAR(E65D,K74R,E80A,D82A,K130T,K135R) with a specific activity of 150 were purified. The endotoxin content was <0.1 and 0.26 IU/mg. Gel filtration on HPLC revealed a single main symmetrical peak in the chromatographic range of the column, representing >98% of the eluted material (total area under the curve) (not shown). SDS gel electrophoresis of 40 μg samples revealed single main components (not shown). Preparations sterilized by filtration proved to be sterile on 3 day testing as described elsewhere (22). Intravenous bolus injection of SakSTAR variants in groups of 5 mice (3 mg/kg body weight), did not provoke any acute reaction, nor reduced weight gain within 8 days, in comparison with mice given an equal amount of saline (not shown).

Thrombolvtic Efficacy

Wild-type SakSTAR or the variants SakSTAR(K74Q, E80A,D82A,K130T,K135R) or SakSTAR(E65D,K74R, E80A,D82A,K130T,K135R) were administered intra-arterially at or in the proximal end of the occlusive thrombus as a bolus of 2 mg followed by an infusion of 1 mg/hr (reduced overnight in some patients to 0.5 mg/hr) in groups of 15, 6 and 6 patients respectively with angiographically documented occlusion of a peripheral artery or bypass graft of less than 30 days duration. Patients were studied after giving informed consent, and the protocol was approved by the Human Studies Committee of the University of Leuven. Inclusion and exclusion criteria, conjunctive antithrombotic treatment (including continuous intravenous heparin) and the study protocol were essentially as previously described (22).

Relevant baseline characteristics of the individual patients and results of treatment and outcome are shown in Table 11. Intra-arterial infusion, at a dose of 3.5 to 27 mg and a duration of 2 to 44 hrs, induced complete recanalization in 22 patients and partial recanalization in 5. Complementary endovascular procedures (mainly PTA) were performed in 13 patients and complementary reconstructive vascular surgery following thrombolysis in 5. One patient underwent major amputation. Bleeding complications were usually absent or limited to mild to moderate hematoma formation at the angiographic puncture sites (data not shown). One patient, given wild-type SakSTAR suffered a non-fatal intracranial bleeding, one (BUE) a retroperitoneal hematoma and two (MAN and STRO) a gastro-intestinal bleeding.

Circulating fibrinogen, plasminogen and $\alpha_2$-antiplasmin levels remained unchanged during infusion of the SakSTAR moieties (data not shown), reflecting absolute fibrin specificity of these agents at the dosages used (data not shown). Significant in vivo fibrin digestion occurred as evidenced by elevation of fibrin fragment D-dimer levels. Intra-arterial heparin therapy prolonged aPTT levels to a variable extent (data not shown).

Antibody Induction

Staphylokinase-neutralizing activity in plasma and antigen-specific IgG antibodies were quantitated essentialy as described above and elsewhere (22).

Antibody-related SakSTAR-, SakSTAR(K74Q,E80A, D82A,K130T,K135R)- and SakSTAR(E65D,K74R,E80A, D82A,K130T,K135R)-neutralizing activity and anti-SakSTAR, anti-SakSTAR(K74Q,E80A,D82A,K130T, K135R) and anti-SakSTAR(E65D,K74R,E80A,D82A, K130T,K135R) IgG, were low at baseline and during the first week after the infusion (FIG. 5). From the second week on, neutralizing activity levels increased to reach median values at 3 to 4 weeks of 9 μg SakSTAR(K74Q, E80A, D82A,K130T,K135R) and 0.5 μg SakSTAR(E65D,K74R, E80AD82A,K130T,K135R) neutralized per mL plasma in the patients treated with the corresponding moieties, respectively, as compared to median value of 24 μg wild-type SakSTAR neutralized per mL in the 15 patients treated with SakSTAR. The levels of anti-SakSTAR(K74Q,E80A, D82A,K130T,K135R) and of anti-SakSTAR(E65D,K74R, E80A, D82A,K130T,K135R) IgG increased to median values at 3 to 4 weeks of 420 and 30 μg/mL plasma in patients treated with the corresponding moieties, respectively, as compared to a median value of 590 μg anti-SakSTAR per mL plasma in the patients treated with SakSTAR (FIG. 5). The prevalence of immunization, defied as neutralizing activities in plasma after 2 to 4 weeks exceeding 5 μg/ml was 3 of 6 patients (50 percent) with SakSTAR(K74Q80A, D82A,K130T,K135R), 1 of 6 patients (17 percent) with SakSTAR(E65D,K74R,E80A,D82A,K130T,K135R), as compared to 56 of 70 patients (80 percent) with SakSTAR. This difference is statistically highly significant (p=0.01 by 2×3 Chi square analysis).

The antibodies induced by treatment with SakSTAR were completely absorbed by SakSTAR but incompletely by SakSTAR(K74Q,E80A,D82A,K130T,K135R) and by SakSTAR(E65D,K74R,E80A,D82A,K130T,K135R) (Table 12). Antibodies induced by treatment with SakSTAR(K74Q, E80A,D82A,K130T,K135R), detectable in 4 of the 6 patients, were completely (≧90 percent) absorbed by SakSTAR, by SakSTAR(K74Q,E80A, D82A,K130T, K135R) and by SakSTAR(E65D,K74R,E80A,D82A, K130T,K135R), indicating that immunization was not due to neoepitopes generated by substitution of wild-type amino acids. Antibodies induced by treatment with SakSTAR (E65D,K74R,E80A,D82A,K130T,K135R) detectable in one patient (URB) were completely absorbed with SakSTAR (K74Q,E80A,D82A,K130T,K135R) and with SakSTAR (E65D,K74QE80A,D82A,K130T,K135R) but incompletely (85%) with wild-type SakSTAR, suggesting that a small fraction of the induced antibodies might be directed against a neoepitope in the variant used for infusion.

EXAMPLE 10

Construction, Purification and Characterization of Cysteine-Substitution Mutants of Staphylokinase Site-directed mutagenesis was applied to substitute exposed amino acids with single cysteine residues in order to construct i) homodimeric forms of staphylokinase, upon formation of an intermolecular disulfide bridge, and ii) polyethylene glycol-conjugated molecules (PEG-derivatives). The aim for this study is twofold: first, the clearance can be reduced by increasing the size of the injected molecule (via dimerization or conjugation with large molecule such as PEG) and second, PEG-derivatives have also been shown to induce a reduced immunoreactivity in animal models (for review, see ref. 34). In both cases, a prolonged half-life in vivo could help to reduce the pharmacological dosis of straphylokinase in patients. This reduction could be accompanied with a reduced immunogenic reaction against the thrombolytic agent.

In this example, the construction and characterization of two SakSTAR variants in which one single amino acid was substituted with cysteine is described. The mutants described under this example are listed in Table 13. These variants were expressed in *E. coli*, purified and characterized to some extent in terms of specific activity, fibrinolytic properties in human plasma in vitro and pharmacokinetic properties following bolus injection in hamsters.

Reagents and Methods

The source of all reagents used in the present study has previously been reported (22), or is specified below. The template vector for mutagenesis, pMEX602sakB (i.e. pMEX.SakSTAR), has been described elsewhere (23). Restriction and modification enzymes were purchased from New England Biolabs (Leusden, The Netherlands), Boehringer Mannheim (Mannheim, Germany) or Pharmacia (Uppsala, Sweden). The enzymatic reactions were performed according to the supplier recommendation. The mutagenic oligonucleotides and primers were obtained from Eurogentec (Seraing, Belgium). Plasmid DNA was isolated using a purification kit from Qiagen (Hilden, Germany), as recommended. Transformation-competent *E. coli* cells were prepared by the well-known calcium phosphate procedure. Nucleotide sequence determination was performed on double strand plasmid DNA with the dideoxy chain termination method, using the T7 sequencing kit (Pharmacia, Uppsala, Sweden). Polymerase chain reactions (PCR) were performed using Taq polymerase from Boehringer Mannheim (Mannheim, Germany). The recombinant DNA methods required to construct the variants described in this example are well established (22,27).

Construction of Expression Plasmids

The variants SakSTAR(K102C) and SakSTAR(K109C), were constructed by the spliced overlap extension polymerase chain reaction (SOE-PCR) (24) using pMEX.SakSTAR encoding SakSTAR as template. Two fragments were amplified by PCR (30 cycles: 1 sec at 94° C. 1 sec at 50° C., 10 sec at 72° C.), the first one starting from the 5' end (primer 818A) of the *staphylokinase* gene to the region to be mutagenized (forward primer), the second one from this same region (backward primer) to the 3' end of the gene with primer 818D (5' CAAACAGCCAAGCTTCATTCATTCAGC) (SEQ ID NO: 5). The forward and backward primers shared an overlap of around 24 bp (for the contruction of K102C: TAT GAT AAG AAT TGC AAA AAA GAA GAA (backward) (SEQ ID NO: 6) and TTC TTC TTT TTT GCA ATT CTT ATC ATA (forward) (SEQ ID NO: 7) for the construction of K109C: AAA AAG AAG AAA CGT GCT CTT TCC CTA (backward) (SEQ ID NO: 8) and TAG GGA fragments were amplified by PCR (30 cycles: 1 sec at 94° C., 1 sec at 50° C., 10 sec at 72° C.), the first one starting from the 5' end (primer 818A) of the *staphylokinase* gene to the region to be mutagenized (forward primer), the second one from this same region (backward primer) to the 3' end of the gene with primer 818D (5' CAAACAGCCAAGCTTCATTCATTCAGC) (SEQ ID NO: 5). The forward and backward primers shared an overlap of around 24 bp (primers not shown). The two purified fragments were then assembled together in a second PCR reaction with the external primers 818A and 818D (30 cycles: 1 sec at 94° C., 1 sec at 50° C., 10 sec at 72° C.). The amplified product from this final reaction was purified, digested with EcoRI and HindII and ligated into the corresponding site of pMEX.SakSTAR. For each construction, the sequence of the variant was confirmed by sequencing the entire SakSTAR coding region.

Expression and Purification of SakSTAR Variants

The SakSTAR variants were expressed and purified, as described below, from transformed *E. coli* grown in terrific broth (TB) medium (28). A 2 to 4 mL aliquot of an overnight saturated culture in LB medium was used to inoculate a 1 to 2 L culture in terrific broth supplemented with 100 μg/mL ampicillin. The culture was incubated with vigorous aeration and at 30° C. After about 16 hours incubation, IPTG (200 μmol/L) was added to the culture to induce expression from the tac promoter. After 3 hours induction, the cells were pelleted by centrifugation at 4,000 rpm for 20 min, resuspended in 1/10 volume of 0.01 mol/L phosphate buffer pH 6–6.5 and disrupted by sonication at 0° C. The suspension was centrifuged for 20 min at 20,000 rpm and the supernatant was stored at 4° C. or at −20° C. until purification. The material was purified essentially as described above (Example 2): cleared cell lysates containing the SakSTAR variants were subjected to chromatography on a 1.6×5 cm column of SP-Sephadex, followed by chromatography on a 1.6×8 cm column of phenyl-Sepharose. The SakSTAR containing fractions, localized by SDS-gel electrophoresis, were pooled for further analysis.

Biochemical Analysis

Protein concentrations were determined according to Bradford (29). SDS-PAGE was performed with the Phast System™ (Pharmacia, Uppsala, Sweden) using 10–15% gradient gels and Coomassie Brillant blue staining, and the specific activities of SakSTAR solutions were determined with a chromogenic substrate assay carried out in microtiter plates (as described in example 2). The specific activity of the different SakSTAR variants are summarized in Table 13.

Mutant SakSTAR(K102C) was essentially monomeric as visualized by SDS-PAGE and Coomassie Brillant blue staining. Its specific activity was comparable to that of wild-type staphylokinase. In contrast, SakSTAR(K109C) showed a propensity to form dimers (>60%). This resulted in a markedly increased specific activity in the plasminogen-coupled chromogenic substrate assay (see Table 13). Upon reduction with dithiothreitol (DTT) (20-fold molar excess during 1.5 hour at 37° C.) and alkylation with iodoacetamide (100-fold molar excess during 1 hour at 37° C.), the K109C dimer is converted into a stable monomer and its resulting specific activity is within the expected range towards wild-type staphylokinase (Table 13). This results confirms that formation of homodimers is the unique determinant for this large increase in specific activity. Dimeric SakSTAR(K109C) was separated from monomeric SakSTAR(K109C) by chromatography on Source S (Pharmacia) (5×50mm). Loading buffer was 10 mM phosphate, pH 6.0 and dimeric SakSTAR (K109C) was eluted by a salt gradient (up to 1 M) in the same buffer. The dimeric SakSTAR(K109C) (>95% pure) containing fractions, localized by SDS-gel electrophoresis, were pooled for further analysis.

Chemical Crosslinking of Cysteine Mutants of SakSTAR with Polyethylene Glycol

The thiol group of the cysteine mutant SakSTAR(K102C) was targeted for coupling with an activated polyethylene glycol, OPSS-PEG (Shearwater Polymers Europe, Enschede, The Netherlands). OPSS-PEG is a 5 kDa PEG molecule carrying a single activated thiol group at one end that react specifically at slightly alkaline pH with free thiols. Modification of SakSTAR(K102C) was achieved by incubating the molecule (100 $\mu$M) with a three-fold excess of SS-PEG in a 5 mM phosphate, pH 7.9 solution at room temperature. The extent of the reaction was monitored by following the release of 2-thiopyridone from OPSS-PEG at 412 nm. After reaction (about 15 min), the excess of OPSS-PEG was removed by purifying the derivatized SakSTAR(K102C-PEG) on a 1.6×5 cm column of SP-Sephadex as described above (see Example 2). The SakSTAR(K102C-PEG) containing fractions, localized by optical density at 280 nm, were pooled for further analysis. SDS-PAGE analysis and Coomassie blue staining confirmed that PEG crosslinking on SakSTAR(K102C) was quantitative. As shown in Table 13, the specific activity of the PEG-derivative was only marginally affected when compared to that of wild-type staphylokinase.

Fibrinolytic Properties of SakSTAR Variants in Human Plasma In Vitro

The fibrinolytic and fibrinogenolytic properties of SakSTAR variants were determined as previously described. Dose- and time-dependent lysis of $^{125}$I-fibrin labeled human plasma clots submerged in human plasma was obtained with four molecules: SakSTAR(K109C) as dimer and as monomer (after reduction and alkylation with iodoacetamide), the monomeric SakSTAR($K_{102}$C) and the PEG-derivatized SakSTAR($K_{102}$C). Spontaneous clot lysis during the experimental period was <5% (not shown). Equi-effective concentrations of test compound (causing 50% clot lysis in 2 hrs; C50), determined graphically from plots of clot lysis at 2 hrs versus the concentration of plasminogen activator (not shown), were comparable to that of SakSTAR, for monomeric SakSTAR(K109C) and SakSTAR(K102C) (Table 13). However, it was observed that the $C_{50}$ for clot lysis by dimeric SakSTAR(K109C) was only 0.12 $\mu$g/ml, which is approximately three-fold lower than for wild-type staphylokinase. In contrast, a $C_{50}$ of 0.60 $\mu$g/ml was measured for SakSTAR(K102C-PEG), which is only two-fold higher than for wild-type staphylokinase. Thus, dimerization of SakSTAR via disulfide bridges or increasing the size of the molecule via PEG-derivatization does not preclude the fibrinolytic activity of staphylokinase. While a PEG-molecule appears to reduce the diffusion and therefore fibrinolytic potency of the derivatized staphylokinase within a fibrin clot, dimerization of staphylokinase results in a synergistic fibrinolytic effect on human fibrin clots.

Pharmacokinetic Properties of Dimeric SakSTAR(K109C) and SakSTAR(K102C-PEG) Following Bolus Injection in Hamsters The pharmacokinetic parameters of the disposition of dimeric SakSTAR(K109C) and SakSTAR(K102C-PEG) from blood were evaluated in groups of 4 hamsters following intravenous bolus injection of 100 $\mu$g/kg SakSTAR variant. SakSTAR-related antigen was assayed using the ELISA described elsewhere. The ELISA was calibrated against each of the SakSTAR variants to be quantitated. Pharmacokinetic parameters included: initial half-life (in min), $t½\alpha=\ln2/\alpha$; terminal half-life (in min), $t½\beta=\ln2/\beta$; volume of the central (plasma) compartment (in mL), $V_C$=dose/(A+B); area under the curve (in $\mu$g.min.mL$^{-1}$), AUC=A/$\alpha$+B/$\beta$; and plasma clearance (in mL.min$^{-1}$), Clp=dose/AUC (32).

The disposition rate of staphylokinase-related antigen from blood following bolus injection of 100 $\mu$g/kg of the selected SakSTAR variants in groups of 4 hamsters could adequately be described by a sum of two exponential terms by graphical curve peeling (results not shown), from which the pharmacokinetic parameters t½$\alpha$ and Clp, summarized in Table 13 were derived. The pharmacokinetic parameters of dimeric SakSTAR(K109C) and SakSTAR(K102C-PEG) were markedly different from those of wild type SakSTAR. Initial plasma half-lives (t½($\alpha$)) were 3.6 and . . . min and plasma clearances (Clp) were 0.52 and . . . mL/min, for dimeric SakSTAR(K109C) and SakSTAR(K102C-PEG), respectively. These results may be due to the increase of the Stokes radius of SakSTAR as a result of the dimerization or crosslinking with PEG. According to size-eclusion chromatography on Superdex50 by HPLC, dimeric SakSTAR (K109C) and SakSTAR(K102C-PEG) have apparent molecular weights of 33 kDa and 40 kDa, respectively.

Conclusion

In summary, the present experience illustrates that staphylokinase variants with markedly reduced antibody induction but intact thrombolytic potency can be generated. To our knowledge, this observation constitutes the first case in which a heterologous protein, with the use of protein engineering techniques, is rendered significantly less immunogenic in man without reducing its biological activity.

The present invention was inititated by the observation that certain "clustered charge-to-alanine" substitution variants of recombinant staphylokinase (SakSTAR variant (9)) had a reduced reactivity with antibodies induced by treatment with wild type SakSTAR (3,4) and induced less antibodies than wild type SakSTAR in patients with peripheral arterial occlusion (22,32,35). In an effort to optimize the specific activity versus antigenicity ratio, a comprehensive mutagenesis study, comprising the construction and expression of over 250 plasmids encoding SakSTAR variants, and the purification of the translation products was undertaken. The SakSTAR variants were characterized in terms of specific activity, affinity towards a panel of murine monoclonal antibodies and absorption of SakSTAR specific antibodies from pooled plasma of 10 patients treated with wild type SakSTAR and of two subpools of 3 patients each which reacted strongly (subpool B) or poorly (subpool C) with the immunodominant epitope K74,E75,R77. In a later phase, an additional pool of 40 patients treated with wild-type SakSTAR was also used for absorption studies. The values obtained with both pools were in good agreement. Linear regression analysis yielded: (Pool 10)=(Pool 40)+ . . . , with r= . . . .

Residues for site-directed mutagenesis were selected in three ways: 1) a comprehensive analysis of variants with 1 or 2 adjacent amino acids substituted with Ala; 2) analysis of the differential reactivity of the two natural variants SakSTAR and Sak42D (which corresponds to SakSTAR (S34G,G36R,H43R) and 3) surface exposure of the residues as derived from the three dimensional structure. From these analyses, SakSTAR(K35A), SakSTAR(N95A) and SakSTAR(S103A) emerged with specific activities >200 kU/mg, SakSTAR(W66A), SakSTAR(Y73A) and SakSTAR (E75A) with reduced reactivity with ≧3 of the 5 antibodies of epitope cluster I, SakSTAR(H43A) and SakSTAR(V45A) with 3 antibodies of epitope cluster II, and SakSTAR (V32A), SakSTAR(K35A), SakSTAR(D82A) and SakSTAR (K130A) and ≧3 of the 5 antibodies of epitope cluster III. However, only SakSTAR(Y73A) and SakSTAR(K74A) reduced the antibody binding from pooled immunized patient plasma by ≧30 percent. Analysis of the differential reactivity of SakSTAR and Sak42D revealed that the reduced reactivity with antibodies of epitope cluster III and with immunized patient plasma could be ascribed to the G36R substitution. In addition E65 and K135 of SakSTAR were targeted because of their location, in the three-dimensional structure (36), in the close vicinity of the immunodominant K74,E75,R77 epitope.

Substitution of K35 with other amino acids than Ala did not improve the specific activity over that of SakSTAR (K35A), and substitution of Y73 with other residues did not rescue the impaired specific activity. SakSTAR(E80A, D82A) had an intact specific activity and a somewhat lower reactivity with immunized patient plasma, and the increased specific activity of SakSTAR(N95A) could not be conferred to variants containing K74A or K135R. SakSTAR(K130A) was outperformed in terms of specific activity by SakSTAR (K130T). K74 confirmed its key role in binding of antibodies from immunized patient plasma in the absence of a markedly reduced reactivity with the murine monoclonal antibodies (22), the best specific activity/antigenicity ratios being obtained with SakSTAR(K74Q) and SakSTAR (K74R).

The SakSTAR(K130T,K135R) variant was taken as a template for additive mutagenesis because of its high specific activity with a moderate reduction of binding to antibodies of epitope cluster III and of absorption of antibodies from immunized patient plasma (Table 6). Addition of G36R, K74R or both to the template did not affect the specific activity, but reduced the reactivity with monoclonal antibodies against epitope cluster III (G36R substitution) and decreased the absorption of antibodies from immunized patient plasma (K74R substitution). Addition of E80A and/or D82A to the SakSTAR(K130T,K135R) template did not affect the specific activity and was selected as a template for further mutagenesis because of its reduced reactivity with epitope cluster III antibodies (Table 7). Addition of K74R and even more of K74Q drastically reduced the reactivity with immunized patient plasma. Finally, addition of E65D or E65Q to the SakSTAR(K74R,E80A,D82A, K130T,K135R) template yielded variants with intact specific activity which only bound ⅓ of the antibodies of pooled immunized patient plasma, only about 10 to 30 percent of the antibodies from plasma of patients with a high concentration of antibodies directed towards the immunodominant K74,E75,R77 (Subpool B) and only about 60 percent of the antibodies from plasma of patients with a very low concentration of antibodies directed against this immunodominant epitope (Subpool C). Based on this analysis, SakSTAR(K74Q, E80A, D82A,K130T,K135R), and SakSTAR(E65D,K74R, E80A, D82A,K130T,K135R) were selected for further analysis.

The fibrinolytic potency and the fibrin-selectivity of these selected mutants in a plasma milieu was indistinguishable from that of wild type SakSTAR. The temperature stability of the mutants was still acceptable with no significant loss of activity upon incubation at 37° C. for 3 days, although at 56° and 70° C., they were more rapidly inactivated than wild-type SakSTAR. The pharmacokinetics of the SakSTAR variants following intravenous bolus injection in hamsters did not reveal major differences with wild type SakSTAR except for a possibly somewhat higher plasma clearance.

In conclusion, the two variants of SakSTAR which emerged from the present site directed mutagenesis program are characterized by an intact or slightly increased specific activity, maintained thrombolytic potency and fibrin-selectivity in a human plasma milieu, acceptable although slightly reduced temperature stability and a markedly reduced reactivity with anti-SakSTAR antibodies in pooled immunized patient plasma. In view of the previously found correlation between reduced antigenicity and reduced immunogenicity of certain "charged-cluster-to-alanine" variants investigation of immunogenicity associated with their use for thrombolytic therapy in man appeared warranted.

Highly purified, sterilized preparations of SakSTAR (K74Q,E80A,D82A,K130T,K135R) and SakSTAR(E65D, K74R,E80A,D82A,K130T,K135R) were produced and found to contain low endotoxin levels, and to be devoid of acute toxicity in mice following intravenous bolus injection at a dose of 3 mg/kg.

Intra-arterial administration of wild-type SakSTAR, SakSTAR(K74Q,E80A,D82A,K130T, K135R) or SakSTAR (E65D,K74R,E80A,D82A,K130T,K135R) as a bolus of 2 mg followed by an infusion of 1 mg/hr in 6 patients with angiographically documented occlusion of a peripheral artery or bypass graft each, resulted in complete recanalization in 10 patients and partial recanalization in 2, without measurable systemic plasminogen activation. Following administration of wild-type or variant SakSTAR, neutralizing antibody titers and specific IgG levels remained low for one week. From the second or third week onwards, an increase of SakSTAR-neutralizing activity to ≧5 μg/mL plasma was observed in the 3 of the 6 patients given SakSTAR(K74Q,E80A,D82A,K130T,K135R), and in only . . . of the . . . patients given SakSTAR(E65D,K74R, E80A,D82A,K130T,K135R). This immunization rate of . . . % with the variants is significantly lower than the immunization rate of 80% observed in 70 patients treated with SakSTAR (p= . . . by Fisher's exact text). The antibodies induced by treatment with the SakSTAR variants were completely absorbed by SakSTAR, and by the respective variants in all but one patient with measurable neutralizing antibody levels, indicating that immunization was not due to neoepitopes generated by substitution but to residual epitopes in the SakSTAR template.

References

1. Lack C H: Staphylokinase: an activator of plasma protease. Nature 161: 559, 1948.
2. Lewis J H, Ferguson J H: A proteolytic enzyme system of the blood. III. Activation of dog serum profibrinolysin by staphylokinase. Am J Physiol 166: 594, 1951.

3. U.S. Pat. No. 5,336,495 (issued Aug. 9, 1994).
4. Vanderschueren S, Barrios L, Kerdsinchai P, Van den Heuvel P, Hermans L, Vrolix M, De Man F, Benit E, Muyldermans L, Collen D, Van de Werf F: A randomized trial of recombinant staphylokinase versus alteplase for coronary artery patency in acute myocardial infarction. Circulation 92: 2044–2049, 1995.
5. Sako T, Sawaki S, Sakurai T, Ito S, Yoshizawa Y, Kondo I: Cloning and expression of the staphylokinase gene of *Staphylococcus aureus* in *Escherichia coli*. Molec Gen Genet 190: 271–277, 1983.
6. Behnke D, Gerlach D: Cloning and expression in *Escherichia coli, Bacillus subtilis*, and *Streptococcus sanguis* of a gene for staphylokinase—a bacterial plasminogen activator. Molec Gen Genet 210: 528–534, 1987.
7. Collen D, Silence K, Demarsin E, De Mol M, Lijnen HR: Isolation and characterization of natural and recombinant staphylokinase. Fibrinolysis 6: 203–213, 1992.
8. Sako T, Tsuchida N: Nucleotide sequence of the staphylokinase gene from *Staphylococcus aureus*. Nucleic Acids Res 11: 7679–7693, 1983.
9. Collen D, Zhao Z A, Holvoet P, Marynen P: Primary structure and gene structure of staphylokinase. Fibrinolysis 6: 226–231, 1992.
10. Sakai M, Watanuki M, Matsuo O: Mechanism of fibrin-specific fibrinolysis by staphylokinase: participation of $\alpha_2$-plasmin inhibitor. Biochem Biophys Res Comm 162: 830–837, 1989.
11. Matsuo O, Okada K, Fukao H, Tomioka Y, Ueshima S, Watanuki M, Sakai M: Thrombolytic properties of staphylokinase. Blood 76: 925–929, 1990.
12. Lijnen H R, Van Hoef B, De Cock F, Okada K, Ueshima S, Matsuo O, Collen D: On the mechanism of fibrin-specific plasminogen activation by staphylokinase. J Biol Chem 266: 11826–11832, 1991.
13. Lijnen H R, Van Hoef B, Matsuo O, Collen D: On the molecular interactions between plasminogen-staphylokinase, $\alpha_2$-antiplasmin and fibrin. Biochim Biophys Acta 1118: 144–148, 1992.
14. Silence K, Collen D, Lijnen HR: Interaction between staphylokinase, plasmin(ogen) and $\alpha_2$-antiplasmin. Recycling of staphylokinase after neutralization of the plasmin-staphylokinase complex by $\alpha_2$-antiplasmin. J Biol Chem 268: 9811–9816, 1993.
15. Silence K, Collen D, Lijnen H R: Regulation by $\alpha_2$-antiplasmin and fibrin of the activation of plasminogen with recombinant staphylokinase in plasma. Blood 82: 1175–1183, 1993.
16. Sakharov D V, Lijnen H R, Rijken D C. Interactions between staphylokinase, plasmin(ogen), and fibrin. J Biol Chem 271: 27912–27918, 1996.
17. Schlott B, Gührs K H, Hartmann M, Röcker A, Collen D. Staphylokinase requires $NH_2$-terminal proteolysis for plasminogen activation. J Biol Chem (in press).
18. Collen D, De Cock F, Vanlinthout I, Declerck P J, Lijnen H R, Stassen J M. Comparative thrombolytic and immunogenic properties of staphylokinase and streptokinase. Fibrinolysis 6: 232–242, 1992.
19. Collen D, De Cock F, Stassen J M. Comparative immunogenicity and thrombolytic properties toward arterial and venous thrombi of streptokinase and recombinant staphylokinase in baboons. Circulation 87: 996–1006, 1993.
20. White H: Thrombolytic treatment for recurrent myocardial infarction. Br Med J 302: 429–430, 1991.
21. Gase A, Hartmann M, Gührs K H, Röcker A, Collen D, Behnke D, Schlott B: Functional significance of $NH_2$- and COOH-terminal regions of staphylokinase in plasminogen activation. Thromb Haemost 76: 755–760, 1996.
22. EP 95200023.0 (Jan. 6, 1995) and U.S. Ser. No. 08/499,092 (Jul. 6, 1995).
23. Schlott B, Hartmann M, Gührs K H, Birch-Hirschfeid E, Pohl H D, Vanderschueren S, Van de Werf F, Michoel A, Collen D, Behnke D: High yield production and purification of recombinant staphyiokinase for thrombolytic therapy. Bio/technology 12: 185–189, 1994.
24. Horton R M, Hunt H D, Ho S N, Pullen J K, Pease L R. Engineering hybrid genes without the use of restriction enzymes: gene splicing by overlap extension. Gene 77: 61–68, 1989.
25. BLAcore system manual, 5-2, Pharmacia Biosensor AB, Uppsala, Sweden.
26. Karlsson R, Michaelsson A, Mattsson L: Kinetic analysis of monoclonal antibody-antigen interactions with a new biosensor based analytical system. J Immunol Methods 145: 229–240, 1991.
27. Sambrook J, Fritsch E F, Maniatis T: Molecular cloning: a laboratory mannual. 2nd Ed. Cold Spring Harbor, N.Y. Cold Spring Harbor Laboratory Press, 1989.
28. Tartof K D, Hobbs C A: Improved media for growing plasmid and cosmid clones. Bethesda Res Lab Focus 9: 12, 1987
29. Bradford M M: A rapid and sensitive method for the quantitation of microgram quantities of protein utilizing the principle of protein-dye binding. Anal Biochem 72: 248, 1976.
30. Deutsch D G, Mertz E T: Plasminogen: purification from human plasma by affinity chromatography. Science 170: 1095–1096, 1970.
31. Collen D, Moreau H, Stockx L, Vanderschueren S. Recombinant staphylokinase variant with altered immunoreactivity. II. Thrombolytic properties and antibody induction. Circulation 94: 207–216, 1996.
32. Vanderschueren S, Stockx L, Wilms G, Lacroix H, Verhaeghe R, Vermylen J, Collen D: Thrombolytic therapy of peripheral arterial occlusion with recombinant staphylokinase. Circulation 92: 2050–2057, 1995.
33. Gibaldi M, Perrier D. Pharmacokinetics, Marcel Dekker, New York, N.Y., 1983, 45–111.
34. Inada Y, Furukawa M, Sasaki H, Kodera Y, Hiroto M, Nishimura H, Matsushima A. Biomedical and biotechnological applications of PEG- and PM-modified proteins, TIBTECH 13: 86–91, 1995.
35. Collen D, Bernaerts R, Declerck P, De Cock F, Demarsin E, JennéS, Laroche Y, Lijnen H R, Silence K, Verstreken M. Recombinant staphylokinase variants with altered immunoreactivity. I. Construction and characterization. Circulation 94: 197–206, 1996.
36. Rabijns A, De Bondt H L, De Ranter C. Three-dimensional structure of staphylokinase, a plasminogen activator with therapeutic potential. Nature Struct Biol 4: 357–360, 1997.

TABLE 1

Alanine-to-wild-type" reversal variants of "charged-cluster-to-alanine" mutants of SakSTAR: Association constants ($K_A \times 10^7$ mol/$L^{-1}$) for the binding to insolubilized murine monoclonal antibodies (Mabs), and absorption (percent) of antibodies of immunized patient plasma

| | | | murine MAbs | | | | | | | | | |
|---|---|---|---|---|---|---|---|---|---|---|---|---|
| | Exp. | Spec. Act. | Epitope I | | | | | Epitope II | | | | |
| Variant | (mg/L) | (kU/mg) | 17G11 | 26A2 | 30A2 | 2B12 | 3G10 | 18F12 | 14H5 | 28H4 | 32B2 | 7F10 |
| SakSTAR | | 130 | 22 | 13 | 2.9 | 7.8 | 11 | 38 | 7.4 | 19 | 7.7 | 2.4 |
| SakSTAR(K35A, E38A) | | 97 | 15 | 22 | 4.2 | 11 | 7.9 | 110 | 10 | 15 | 12 | 2.2 |
| SakSTAR(K74A, E75A, R77A) | | 110 | 11 | <.01 | <0.1 | <0.1 | <0.1 | 150 | 17 | 28 | 14 | 3.3 |
| SakSTAR(K35A, E38A, K74A, E75A, R77A) | | 50 | 11 | <0.1 | <0.1 | <0.1 | <0.1 | 110 | 36 | 26 | 15 | 2.0 |
| SakSTAR(E38A, K74A, E75A, R77A) | | 43 | 11 | <0.1 | <0.2 | <0.1 | <0.1 | 140 | 39 | 26 | 15 | 2.1 |
| SakSTAR(K35A, K74A, E75A, R77A) | | 56 | 9.2 | <0.1 | 0.15 | <0.1 | <0.1 | 52 | 14 | 29 | 8.8 | 2.3 |
| SakSTAR(K35A, E38A, E75A, R77A) | | 44 | 11 | 0.3 | 0.1 | 0.2 | <0.1 | 75 | 9.8 | 12 | 7.3 | 1.6 |
| SakSTAR(K35A, E38A, K74A, R77A) | | 41 | 8.8 | 2.9 | <0.1 | 2.0 | 0.33 | 110 | 29 | 31 | 10 | 2.0 |
| SakSTAR(K35A, E38A, K74A, E75A) | | 19 | 13 | <0.1 | 0.1 | <0.1 | <0.1 | 180 | 41 | 37 | 15 | 1.6 |
| SakSTAR(E38A, E75A, R77A) | | 88 | 11 | 0.6 | 0.15 | 0.4 | 0.3 | 79 | 12 | 15 | 10 | 2.0 |
| SakSTAR(E38A, E75A) | | 66 | 16 | 0.3 | <0.1 | <0.1 | 0.9 | 56 | 11 | 13 | 8.9 | 2.0 |
| SakSTAR(K35A, E75A, R77A) | | 68 | 9.2 | <0.1 | <0.1 | <0.1 | <0.1 | 60 | 7.0 | 13 | 11 | 3.3 |
| SakSTAR(K35A, E75A) | | 150 | 17 | 0.12 | <0.1 | 0.16 | 0.14 | 40 | 7.2 | 13 | 9.2 | 4.2 |
| SakSTAR(K74A) | | 100 | 12 | 7.6 | 0.17 | 4.4 | 2.1 | 55 | 15 | 33 | 14 | 3.6 |
| SakSTAR(E75A) | | 140 | 13 | 1.2 | <0.1 | <0.1 | <0.1 | 46 | 8.5 | 14 | 12 | 3.4 |
| SakSTAR(K74A, E75A, R77A, E80A, D82A) | | 50 | 14 | <0.1 | <0.1 | <0.1 | <0.1 | 180 | 19 | 33 | 19 | 3.7 |
| SakSTAR(E80A, D82A) | | 130 | 7.3 | 12 | 2.1 | 6.5 | 5.9 | 79 | 6.1 | 8.4 | 7.8 | 1.9 |
| SakSTAR(E80A) | | 160 | 13 | 13 | 3.3 | 7.9 | 10 | 35 | 7.4 | 17 | 8.6 | 2.1 |
| SakSTAR(D82A) | | 160 | 17 | 12 | 4.8 | 7.3 | 11 | 31 | 7.8 | 17 | 12 | 2.7 |
| SakSTAR(E75A, D82A) | | 170 | 20 | 15 | 3.1 | 6.6 | 7.2 | 69 | 8.1 | 15 | 14 | 4.9 |

| | murine MAbs | | | | | | | |
|---|---|---|---|---|---|---|---|---|
| | Epitope III | | | | | SakSTAR patient plasma | | |
| Variant | 7H11 | 25E1 | 40C8 | 24C4 | 1A10 | Pool | Subpool B | Subpool C |
| SakSTAR | 4.0 | 14 | 5.4 | 2.9 | 0.6 | 95 | 95 | 95 |
| SakSTAR(K35A, E38A) | <0.1 | <0.1 | <0.1 | 1.0 | 1.0 | 93 | 91 | 94 |
| SakSTAR(K74A, E75A, R77A) | 2.4 | 11 | 4.0 | 2.1 | 0.9 | 55 | 43 | 95 |
| SakSTAR(K35A, E38A, K74A, E75A, R77A) | <0.1 | <0.1 | <0.1 | 1.5 | 1.2 | 52 | 41 | 92 |
| SakSTAR(E38A, K74A, E75A, R77A) | <0.1 | 3.2 | 3.7 | 1.6 | 1.1 | 50 | 44 | 95 |
| SakSTAR(K35A, K74A, E75A, R77A) | <0.1 | 1.8 | <0.1 | 1.8 | 0.8 | 46 | 43 | 95 |
| SakSTAR(K35A, E38A, E75A, R77A) | <0.1 | <0.1 | <0.1 | 0.53 | 0.64 | 92 | 87 | 94 |
| SakSTAR(K35A, E38A, K74A, R77A) | <0.1 | <0.1 | <0.1 | 0.63 | 0.74 | 56 | 50 | 93 |
| SakSTAR(K35A, E38A, K74A, E75A) | <0.1 | <0.1 | <0.1 | 1.2 | 0.45 | 48 | 41 | 92 |
| SakSTAR(E38A, E75A, R77A) | <0.1 | 2.6 | 4.7 | 1.1 | 0.81 | 95 | 88 | 95 |
| SakSTAR(E38A, E75A) | <0.1 | 20 | 4.8 | 1.3 | 1.6 | 91 | 90 | 95 |
| SakSTAR(K35A, E75A, R77A) | <0.1 | 1.5 | <0.1 | 0.8 | 1.1 | 88 | 89 | 95 |
| SakSTAR(K35A, E75A) | <0.1 | 1.8 | <0.1 | 1.4 | 1.5 | 94 | 93 | 95 |
| SakSTAR(K74A) | 2.9 | 14 | 4.9 | 3.4 | 1.2 | 59 | 45 | 95 |
| SakSTAR(E75A) | 4.5 | 18 | 5.0 | 1.2 | 2.1 | 95 | 93 | 95 |
| SakSTAR(K74A, E75A, R77A, E80A, D82A) | <0.1 | <0.1 | <0.1 | <0.1 | 1.2 | 49 | 29 | 89 |
| SakSTAR(E80A, D82A) | <0.1 | <0.1 | <0.1 | <0.1 | 0.44 | 89 | 83 | 92 |
| SakSTAR(E80A) | <0.1 | 16 | 3.6 | <0.1 | 1.7 | 94 | 93 | 95 |
| SakSTAR(D82A) | <0.1 | 0.18 | <0.1 | <0.1 | 2.3 | 95 | 93 | 95 |
| SakSTAR(E75A, D82A) | 0.17 | 0.7 | 0.5 | 0.1 | 1.4 | 95 | 95 | 95 |

Apparent association constants ≧10-fold lower than those of wild-type SakSTAR are represented in bold type; Spec. Act. ≧100.000 HU/mg represented in bold type; ≦60% absorption represented in bold type.

TABLE 2

Baseline characteristics and treatment outcome of the patients with peripheral arterial occlusion treated with SakSTAR, SakSTAR(K74A) or SakSTAR(K74A, E75A, R77A)

| Compound Patient Id. | Gender | Age (yrs) | Clinical ischemia | Locus of occlusion | Age of occlusion (days) | Length of occlusion (cm) | Recanalization by thrombolysis | Total dose of thrombolytic agent (mg) | Total duration of infusion (hrs) | Additional therapy |
|---|---|---|---|---|---|---|---|---|---|---|
| SakSTAR | | | | | | | | | | |
| MEE | F | 67 | Rest pain | Left SFA | 30 | 8 | complete | 7.0 | 5.0 | PTA |
| FOR | M | 68 | Claudication | Left IA (stent) | 14 | 18 | complete | 6.5 | 4.5 | PTA + stent |
| DAN | M | 73 | Claudication | Right SFA | 30 | 6 | complete | 7.5 | 5.5 | PTA |
| BER | F | 63 | Rest pain | Left FT graft | 18 | 55 | complete | 18 | 28 | PTA |
| DAM | F | 43 | Acute | Left brachial and radial artery | 2 | 7 | complete | 19 | 17 | PTA + stent |
| TOR | M | 68 | Claudication | Right SFA (popliteal aneurysm) | 50 | 12 | complete | 6.0 | 4.0 | PTA + femoropopliteal bypass graft |
| CLA | M | 74 | Acute | Left PA | 1.5 | 20 | complete | 9.0 | 7.0 | — |
| MAN | M | 65 | Acute | Left EIA (stent) | 4 | 20 | complete | 6.5 | 4.5 | (amputation left digit V) |
| MAT | M | 64 | Subacute | Right FP graft | 3 | 45 | complete | 8.0 | 6.0 | (−) |
| Mean ± SEM | | 65 ± 3.0 | | | 17 ± 5.6 | 21 ± 5.8 | | 9.7 ± 1.7 | 9.1 ± 2.7 | |
| SakSTAR(K74A) | | | | | | | | | | |
| LIE | M | 70 | Subacute | Right FF graft | 10 | 48 | complete | 11 | 9.0 | PTA |
| ENG | M | 50 | Claudication | Right SFA | 28 | 10 | complete | 12 | 10 | PTA |
| COX | F | 48 | Claudication | Right PA graft | 25 | 7 | partial | 15 | 15 | PTA |
| MAN | F | 68 | Claudication | Right SFA | ≧120 | 9 | complete | 9.0 | 7.0 | PTA |
| VHE | M | 47 | Acute | Right IF graft | 10 | 54 | complete | 18 | 16 | Surgical graft revision |
| MUL | F | 51 | Acute | Right IF and FP graft | 1 | 63 | complete | 16 | 20 | PTA |
| BUR | F | 67 | Rest pain | Right TF trunc | 9.0 | 38 | partial | 18 | 21 | — |
| NIJ | F | 60 | Rest pain | Left AF graft | 23 | 78 | complete | 15 | 21 | — |
| POE* | M | 49 | Subacute | Right TF trunc | 2 | 30 | partial | 6.0 | 4.0 | rt-PA, surgical graft lengthening |
| VBE | M | 39 | Subacute | Right BA (embolism) | 20 | 28 | complete | 18 | 23 | Stent right SC artery, first rib resection |
| SME | F | 50 | Subacute | TF trunc | 18 | 32 | complete | 21 | 19 | None |
| WOL | M | 67 | Subacute | Right PA | 4 | 25 | complete | 16 | 22 | — |
| Mean ± SEM | | 56 ± 3.0 | | | 23 ± 9.2 | 35 ± 6.4 | | 15 ± 1.2 | 16 ± 1.9 | |
| SakSTAR(K74A, E75A, R77A) | | | | | | | | | | |
| JAC | F | 65 | Acute | Right BA and UA | 0.3 | 5 | complete | 14 | 12 | — |
| MAE | M | 74 | Rest pain | Left SFA | 10 | 50 | complete | 9.0 | 7.0 | PTA |
| CRA | F | 52 | Claudication | Right IA and FA artery | 14 | 28 | complete | 25 | 23 | PTA + stent |
| VDB | M | 68 | Claudication | Left SFA | 90 | 12 | complete | 9.0 | 7.0 | PTA |
| DUN | M | 71 | Subacute | Left SFA | 14 | 6 | complete | 9.0 | 7.0 | PTA |
| DEL | M | 59 | Acute | Right FT graft | 3 | 42 | complete | 9.0 | 7.0 | PTA |
| Mean ± SEM | | 65 ± 3.3 | | | 22 ± 14 | 24 ± 7.8 | | 13 ± 2.6 | 11 ± 2.6 | |

AF: aortofemoral; BA: brachial artery; CIA: common iliac artery; FF: femorofibular; FP: femoropopliteal; FT: femorotibial; IA: iliac artery; IF: iliofemoral; PA: popliteal artery; PTA, percutaneous transluminal angioplasty; SFA: superficial femoral artery; TF: tibiofibular; UA: ulnar artery.
*Previous treatment with SakSTAR in 1994

TABLE 3

Alanine-substitution variants of SakSTAR: Association constants ($K_A \times 10^7$ mol/L$^{-1}$) for binding to insolubilized murine monoclonal antibodies (Mab) and absorption (percent) of antibodies of immunized patient plasma

| | | | murine MAbs | | | | | | | | | | | | | | | | | |
|---|---|---|---|---|---|---|---|---|---|---|---|---|---|---|---|---|---|---|---|---|
| | Exp. | Spec. Act. | Epitope cluster I | | | | | Epitope cluster II | | | | | Epitope cluster III | | | | | SakSTAR patient plasma | | |
| Variant | (mg/L) | (kU/mg) | 17G11 | 26A2 | 30A2 | 2B12 | 3G10 | 18F12 | 14H5 | 28H4 | 32B2 | 7F10 | 7H11 | 25E1 | 40C8 | 24C4 | 1A10 | Pool | Subpool B | Subpool C |
| SakSTAR | | 120 | 9.3 | 13 | 2.9 | 7.8 | 11 | 38 | 7.4 | 19 | 7.7 | 2.4 | 4.0 | 14 | 5.4 | 2.9 | 0.6 | 95 | 95 | 95 |
| | | | [6.4 | 17 | 7.4 | 19 | 35 | 18 | 25 | >18 | >14 | 1.1 | 0.6 | 11 | 16 | 6.3 | 2.0] | | | |
| SakSTAR(S34G, G36R, H43R) | | 120 | 10 | 14 | 3.3 | 7.5 | 11 | <0.1 | <0.1 | <0.1 | 20 | 2.7 | <0.1 | <0.1 | <0.1 | 0.15 | 1.7 | 87 | 76 | 75 |
| SakSTAR(F4A) | LE | | | | | | | | | | | | | | | | | | | |
| SakSTAR(D5A, K6A) | | 150 | [1.3 | 21 | 12 | 9.2 | 9.7 | 12 | 23 | 17 | 10 | 0.4 | 1.3 | 3.9 | 0.8 | 4.5 | 3.8] | 95 | 95 | 95 |
| SakSTAR(K8A, K10A) | | 24 | [1.8 | 16 | 5 1 | 29 | 15 | 22 | 16 | 26 | 18 | 1.0 | 0.93 | 11 | 1.1 | 18 | 0.75] | 95 | 95 | 95 |
| SakSTAR(Y9A) | 24 | 78 | 22 | 49 | 6.6 | 2.3 | 16 | 44 | 8.4 | 20 | 14 | 2.6 | 2.4 | 16 | 9.6 | 1.1 | 0.5 | 96 | 95 | 95 |
| SakSTAR(K11A, D13A, D14A) | LE | | | | | | | | | | | | | | | | | | | |
| SakSTAR(D13A) | 6 | 46 | 2.4 | 6.1 | 2.0 | 3.7 | 3.4 | 11 | 1.9 | 4.5 | 4.4 | 8.7 | 1.5 | 2.4 | 1.1 | 3 6 | <0.1 | 95 | 94 | 95 |
| SakSTAR(D14A) | 14 | 30 | 5.1 | 13 | 4.0 | 6.6 | 3.1 | 38 | 7.7 | 12 | 15 | 2.2 | 2.7 | 6.0 | 3.2 | 5.6 | <0.1 | 95 | 94 | 95 |
| SakSTAR(S16A) | 41 | 160 | 8.1 | 16 | 4.5 | 8.4 | 9.0 | 15 | 6.1 | 13 | 21 | 3.6 | 4.0 | 8.0 | 4.3 | 2.5 | 0.5 | 95 | 95 | 95 |
| SakSTAR(Y17A, F18A) | 27 | 30 | 13 | 22 | 3.3 | 10 | 9.5 | 21 | 4.6 | 6.7 | 12 | 2.5 | 1.2 | 18 | 6.5 | 3.4 | <0.1 | 95 | 95 | 95 |
| SakSTAR(E19A, P20A) | 36 | 9 | 11 | 19 | 3.3 | 9.2 | 12 | 15 | 6.1 | 11 | 16 | 1.0 | 1.1 | 15 | 5.1 | 3.3 | <0.1 | 93 | 93 | 95 |
| SakSTAR(T21A) | 54 | 170 | 4.8 | 15 | 2.4 | 8.7 | 9.6 | 32 | 11 | 24 | 18 | 1.3 | 1.8 | 9.6 | 2.9 | 5.6 | 0.6 | 95 | 95 | 95 |
| SakSTAR(P23A) | 41 | 67 | 14 | 31 | 4.4 | 14 | 22 | 41 | 5.3 | 37 | 13 | 10 | 4.0 | 11 | 7.6 | 3.1 | 1.9 | 91 | 95 | 95 |
| SakSTAR(Y24A) | 10 | 40 | 17 | 33 | 4.3 | 13 | 11 | 33 | 4.3 | 7.0 | 12 | 4.0 | 0.4 | 14 | 6.8 | 4.8 | <0.1 | 95 | 95 | 95 |
| SakSTAR(L25A) | LE | | | | | | | | | | | | | | | | | | | |
| SakSTAR(M26A) | LE | | | | | | | | | | | | | | | | | | | |
| SakSTAR(V27A) | 62 | 50 | 3.3 | 15 | 1.6 | 7.8 | 7.4 | 12 | 2.9 | 3.7 | 33 | 2.0 | 1.3 | 5.9 | 2.8 | 4.2 | 1.2 | 95 | 95 | 95 |
| SakSTAR(N28A) | 90 | <5 | 5.8 | 29 | 2.1 | 7.0 | 5.5 | 27 | 10 | 20 | 2.5 | 2.1 | 2.1 | 5.6 | 2.1 | 2.1 | 0.7 | 95 | 95 | 95 |
| SakSTAR(N28A, V29A) | 32 | 45 | 18 | 30 | 2.5 | 20 | 18 | 20 | 14 | 20 | 24 | 2.7 | 3.3 | 20 | 1.1 | 5.0 | 2.0 | 93 | 95 | 95 |
| SakSTAR(T30A) | 52 | 140 | 7.4 | 13 | 2.1 | 7.0 | 6.1 | 7.6 | 3.4 | 5.1 | 13 | 3.3 | 5.6 | 12 | 3.4 | 5.4 | 0.8 | 94 | 95 | 95 |
| SakSTAR(V32A) | 78 | 45 | 10 | 9.6 | 2 4 | 6.2 | 7.8 | 56 | 17 | 12 | 14 | 1.4 | <0.1 | <0.1 | <0.1 | <0.1 | 2.2 | 90 | 93 | 95 |
| SakSTAR(D33A, K35A) | | 130 | [2.1 | 19 | 14 | 14 | 19 | 15 | 24 | 32 | 10 | 5.3 | 1.4 | 5.1 | 3.8 | 5.1 | 3.0] | 95 | 95 | 95 |
| SakSTAR(S34A) | 29 | 110 | 17 | 24 | 4.6 | 9.5 | 11 | 28 | 11 | 22 | 15 | 2.9 | 3.1 | 8 8 | 3.8 | 2 0 | 0 2 | 95 | 95 | 93 |
| SakSTAR(K35A) | | 230 | 6.4 | 14 | 3.3 | 8.0 | 7.4 | 31 | 11 | 12 | 11 | 2.6 | <0.1 | 1.3 | 0.2 | 1.7 | 0.8 | 91 | 88 | 95 |
| SakSTAR(K35A, E38A) | | 97 | 15 | 22 | 4.2 | 11 | 7.9 | 110 | 10 | 15 | 12 | 2.2 | <0.1 | <0.1 | <0.1 | 1.0 | 1.0 | 93 | 91 | 94 |
| SakSTAR(G36A) | 14 | 72 | 3.5 | 9.8 | 1.5 | 5.7 | 6 5 | 52 | 4.2 | 17 | 9.2 | 1.4 | <0.1 | <0.1 | 0.9 | 5 0 | 1.0 | 86 | 83 | 78 |
| SakSTAR(N37A) | 40 | 110 | 5.6 | 31 | 3.0 | 10 | 11 | 20 | 4.1 | 14 | 10 | 2.9 | 1.4 | 5.3 | 3.5 | 3.6 | 0 8 | 95 | 95 | 95 |
| SakSTAR(L39A, L40A) | 8 | <5 | 14 | 15 | 3.1 | 5.1 | 8.0 | 27 | 16 | 6.3 | 12 | 2.7 | 1.2 | 5.4 | 3.2 | 2.1 | 0.9 | 93 | 93 | 95 |
| SakSTAR(S41A, P42A) | 24 | 48 | 10 | 25 | 4.1 | 13 | 12 | 11 | 3.0 | 1.9 | 27 | 2.7 | 3.2 | 15 | 4.8 | 3 6 | 1 1 | 95 | 95 | 95 |
| SakSTAR(H43A) | 37 | 69 | 15 | 28 | 9.7 | 18 | 7.6 | <0.1 | <0.1 | <0.1 | 9.1 | 1.5 | 2 0 | 23 | 7.8 | 7.2 | 1 6 | 95 | 95 | 95 |
| SakSTAR(H43A, Y44A) | 13 | <5 | 10 | 22 | 3.7 | 17 | 15 | <0.1 | <0.1 | <0.1 | 1.4 | 3.0 | 2.3 | 11 | 5.2 | 2.1 | 0.1 | 95 | 95 | 95 |
| SakSTAR(V45A) | 19 | <5 | 16 | 5.6 | 1.4 | 4.8 | 6.3 | 2.2 | 0.2 | 1.7 | 32 | 2.6 | 2.1 | 8.3 | 1.1 | 2.8 | 1.6 | 91 | 92 | 95 |
| SakSTAR(E46A, K50A) | LE | | | | | | | | | | | | | | | | | | | |
| SakSTAR(F47A) | 6 | <5 | <0.1 | 4.0 | 1.0 | 3.9 | 3.4 | 5.7 | 2.7 | 2.8 | 8.5 | 1.7 | 0.9 | 8.8 | 3.0 | 3.0 | 0.9 | 90 | 82 | 97 |
| SakSTAR(I49A) | 2 | 43 | 2.7 | 27 | 7.8 | 23 | 22 | 35 | 4.4 | 11 | 6.2 | 1.1 | 2.0 | 5.7 | 2.0 | 1.7 | 0.6 | 95 | 95 | 95 |
| SakSTAR(K50A) | 15 | 42 | <0.1 | 13 | 2.9 | 7.8 | 8.7 | 46 | 8.3 | 12 | 2.2 | 0.5 | 2.8 | 6.4 | 4.0 | 2.3 | 0.6 | 95 | 94 | 95 |
| SakSTAR(T53A, T54A) | 14 | 68 | 0.9 | 19 | 2.7 | 7.6 | 7.8 | 41 | 6.7 | 12 | 15 | 1.5 | 1.9 | 5.1 | 2.3 | 1.0 | 0.6 | 93 | 94 | 95 |
| SakSTAR(L55A) | LE | | | | | | | | | | | | | | | | | | | |
| SakSTAR(T56A) | 17 | 150 | 5.5 | 15 | 3.2 | 12 | 13 | 56 | 5.3 | 12 | 11 | 2.0 | 3.5 | 6.1 | 2.7 | 4.3 | 1.2 | 94 | 92 | 95 |
| SakSTAR(K57A, E58A, K59A) | | 94 | [4 | 8.7 | 6.0 | 7.3 | 27 | 16 | 14 | 6.7 | 5.6 | 0.52 | 0.36 | 1.7 | 0 42 | 1.0 | 1.1] | | | |

TABLE 3-continued

Alanine-substitution variants of SakSTAR: Association constants ($K_A \times 10^7$ mol/$L^{-1}$) for binding to insolubilized murine monoclonal antibodies (Mab) and absorption (percent) of antibodies of immunized patient plasma

| | | | murine MAbs | | | | | | | | | | | | | | | | |
|---|---|---|---|---|---|---|---|---|---|---|---|---|---|---|---|---|---|---|---|
| | Exp. | Spec. Act. | Epitope cluster I | | | | | Epitope cluster II | | | | | Epitope cluster III | | | | | SakSTAR patient plasma | | |
| Variant | (mg/L) | (kU/mg) | 17G11 | 26A2 | 30A2 | 2B12 | 3G10 | 18F12 | 14H5 | 28H4 | 32B2 | 7F10 | 7H11 | 25E1 | 40C8 | 24C4 | 1A10 | Pool | Subpool B | Subpool C |
| SakSTAR(I60A) | 11 | 96 | 12 | 20 | 2.9 | 11 | 13 | 27 | 6.4 | 25 | 2.7 | 1.5 | 0 7 | 5.8 | 2.9 | 1.7 | 1.0 | 95 | 95 | 95 |
| SakSTAR(E61A, E65A) | | 80 | [9.5 | >10 | 8.8 | 21 | 29 | >11 | >16 | 6.6 | >7.2 | 4 6 | 0.5 | 4 6 | 2.0 | 5.9 | 1.5] | | | |
| SakSTAR(Y62A, Y63A) | 24 | <5 | <0.1 | 4.3 | 0.3 | 2.1 | 1.9 | 11 | 2.2 | 3.1 | 8.4 | 1 7 | 0.6 | 9.2 | 3.6 | 3.8 | 0.7 | 89 | 83 | 95 |
| SakSTAR(Y63A) | 4 | <5 | <0.1 | 18 | 3.7 | 9.6 | 13 | 17 | 5.3 | 3.3 | 15 | 1.1 | 2.2 | 5.3 | 4.3 | 1.0 | 3.7 | 89 | 82 | 95 |
| SakSTAR(V64A) | 14 | 48 | 14 | 16 | 2.9 | 6.3 | 7.8 | 15 | 15 | 21 | 21 | 2.6 | 1.6 | 7 6 | 5.6 | 2.8 | 0.7 | 94 | 92 | 95 |
| SakSTAR(E65A) | 25 | 97 | 53 | 20 | 4.4 | 12 | 7.0 | 10 | 5.6 | 9.7 | 1.9 | 1.8 | 2.3 | 4.7 | 3.0 | 5.8 | 0.97 | 95 | 95 | 95 |
| SakSTAR(E65A, D69A) | | <5 | | | | | | | | | | | | | | | | | | |
| SakSTAR(W66A) | 26 | <5 | <0.1 | <0.1 | <0.1 | <0.1 | <0.1 | 15 | 4.4 | 5 7 | 23 | 3.3 | 2.0 | 10 | 1.4 | 1 8 | 0.8 | 85 | 78 | 92 |
| SakSTAR(L68A) | 16 | 93 | 14 | 22 | 3.5 | 8.5 | 9.3 | 29 | 8.7 | 16 | 15 | 4.0 | 2.1 | 5.3 | 3.6 | 4 1 | <0.1 | 92 | 92 | 95 |
| SakSTAR(T71A) | LE | | | | | | | | | | | | | | | | | | | |
| SakSTAR(Y73A) | 20 | <5 | 9.5 | <0.1 | <0.1 | <0.1 | 4.8 | 33 | 7 3 | 11 | 8 9 | 2.0 | 0.5 | 9.0 | 2.5 | 1 4 | 0.8 | 63 | 44 | 93 |
| SakSTAR(Y73A, K74A) | 24 | <5 | 18 | <0.1 | <0.1 | <0.1 | <0.1 | 19 | 6.7 | 23 | 9 9 | 3 2 | 2.7 | 13 | 4.0 | 1.6 | 1.1 | 47 | 28 | 87 |
| SakSTAR(K74A) | 80 | 69 | 4 4 | 2.7 | 0.2 | 2.2 | 1.1 | 17 | 5.2 | 14 | 7.6 | 2.2 | 2.0 | 6 8 | 3.3 | 1 8 | 0.9 | 64 | 58 | 95 |
| SakSTAR(K74A, E75A, R77A) | | 68 | 9.2 | <0.1 | <0.1 | <0.1 | <0.1 | 60 | 7.0 | 13 | 11 | 3.3 | <0.1 | 1.5 | <0.1 | 0 8 | 1.1 | 88 | 89 | 95 |
| SakSTAR(K74A, R77A) | 34 | 41 | 3.5 | 1.8 | 0.2 | 1.5 | 0.4 | 20 | 2 4 | 10 | 2.1 | 1.8 | 1.7 | 2.3 | 2.2 | 1.2 | 0.7 | 74 | 60 | 95 |
| SakSTAR(E75A) | | 140 | 13 | 1.2 | <0.1 | <0.1 | <0.1 | 46 | 8.5 | 14 | 12 | 3.4 | 4.5 | 18 | 5.0 | 1.2 | 2.1 | 95 | 93 | 95 |
| SakSTAR(F76A) | 9 | 90 | 20 | 9.6 | 1.0 | 2.7 | 3.9 | 13 | 6.2 | 20 | 15 | 1.7 | 0.3 | 5.9 | 2.1 | 1.2 | 1.0 | 94 | 92 | 95 |
| SakSTAR(V78A, V79A) | 23 | 68 | 12 | 23 | 4.0 | 10 | 17 | 21 | 18 | 34 | 28 | 2.3 | 1.6 | 4.7 | <0.1 | 0.5 | 1.7 | 93 | 93 | 95 |
| SakSTAR(E80A) | | 160 | 13 | 13 | 3.3 | 7.9 | 10 | 35 | 7.4 | 17 | 8.6 | 2.1 | <0.1 | 16 | 3.6 | <0.1 | 1.7 | 94 | 93 | 95 |
| SakSTAR(E80A, D82A) | | 130 | 7.3 | 12 | 2.1 | 6.5 | 5.9 | 79 | 6.1 | 8.4 | 7.8 | 1.9 | <0.1 | <0.1 | <0.1 | <0.1 | 0.4 | 89 | 83 | 92 |
| SakSTAR(L81A) | 23 | 28 | 12 | 33 | 1.6 | 40 | 11 | 52 | 11 | 17 | 17 | 3.9 | 1.4 | 5.2 | 7.1 | 4.6 | 1.5 | 88 | 95 | 95 |
| SakSTAR(D82A) | | 160 | 17 | 12 | 4.8 | 7.3 | 11 | 31 | 7.8 | 17 | 12 | 2.7 | <0.1 | 0.2 | <0.1 | <0.1 | 2.3 | 95 | 93 | 95 |
| SakSTAR(D82A, S84A) | 72 | 130 | 8.3 | 14 | 2.6 | 8.1 | 8.5 | 23 | 3.8 | 12 | 11 | 1.7 | <0.1 | <0.1 | 1 4 | <0.1 | 1.0 | 91 | 91 | 95 |
| SakSTAR(S84A) | 12/26 | 89 | 8 0 | 16 | 3.8 | 8.6 | 10 | 90 | 8.3 | 11 | 36 | 1.8 | 2.2 | 1.6 | 3.0 | 3.5 | 0.5 | 95 | 95 | 95 |
| SakSTAR(K86A, E88A) | | 73 | [7.2 | 1.4 | 3.7 | 6.0 | 4.6 | 5.7 | 4.9 | 7.7 | 15 | 4.4 | <0.1 | 5.4 | 0.80 | 1.9 | 0.13 | | | |
| SakSTAR(I87A) | 18 | 98 | 6.7 | 23 | 2.8 | 8.6 | 9.1 | 10 | 3.6 | 11 | 7.4 | 2.7 | 1.1 | 7.8 | 3.4 | 4.5 | 1.0 | 95 | 95 | 95 |
| SakSTAR(V89A) | 20 | 87 | 4.6 | 11 | 2.6 | 6.6 | 2.2 | 28 | 7.2 | 7.3 | 3 0 | 1.3 | 1.2 | 5 1 | 2.9 | 3.1 | 0.83 | 95 | 95 | 95 |
| SakSTAR(T90A) | 78 | 120 | 6.0 | 12 | 0.9 | 3.7 | 3.1 | 20 | 4 8 | 7.2 | <0.1 | <0.1 | 2.1 | 6.6 | 2.6 | 2.1 | 0.5 | 95 | 95 | 95 |
| SakSTAR(Y91A) | 5 | 53 | 6.0 | 16 | 3.0 | 7.0 | 13 | 28 | 8.2 | 16 | 0.6 | 2.1 | 1 4 | 3.7 | 1.6 | 1.6 | 0.2 | 95 | 95 | 95 |
| SakSTAR(Y92A) | 16 | 120 | 16 | 23 | 4.1 | 13 | 12 | 29 | 7.3 | 18 | <0.1 | 1.7 | 4.4 | 10 | 3 9 | 5 9 | 1.1 | 95 | 95 | 95 |
| SakSTAR(E93A, K94A) | | 97 | [8.2 | 19 | 13 | 30 | 24 | 18 | 11 | >10 | 9.0 | 0.88 | 1.4 | 11 | 2.4 | 7.0 | 2.1] | | | |
| SakSTAR(K94A, N95A, K97A) | 32 | 8 | NT | | | | | | | | | | | | | | | 95 | 94 | 95 |
| SakSTAR(N95A) | 25 | 260 | 10 | 18 | 4.0 | 10 | 11 | 50 | 13 | 14 | 4.9 | 2.3 | 3.7 | 7.3 | 4.7 | 2.9 | 0.8 | 95 | 94 | 95 |
| SakSTAR(K96A, K97A, K98A) | | 47 | [2.8 | 41 | 23 | 37 | 90 | >16 | 9.1 | 19 | 16 | 0.41 | 0.58 | 17 | 1.2 | 13 | 0.30] | | | |
| SakSTAR(E99A) | 24 | 42 | 7.4 | 15 | 4 0 | 8.4 | 8.9 | 22 | 2.7 | 4 7 | <0.1 | <0.1 | 2.1 | 6 2 | 7 3 | 14 | 0 8 | 92 | 91 | 92 |
| SakSTAR(E99A, E100A) | LE | | | | | | | | | | | | | | | | | | | |
| SakSTAR(T101A) | 23 | 85 | 4.6 | 11 | 2.1 | 6.6 | 7.3 | 30 | 2.8 | 16 | 0.7 | 1.0 | 1.3 | 5.4 | 2.4 | 2.9 | 0.8 | 95 | 95 | 95 |
| SakSTAR(K102A) | 12 | 89 | 4.9 | 12 | 3.7 | 6.5 | 6.3 | 30 | 3.1 | 15 | 8.2 | 6.1 | 0.8 | 4.2 | 1.9 | 10 | 0.6 | 95 | 93 | 95 |
| SakSTAR(S103A) | 67 | 210 | 9.0 | 16 | 5.0 | 9.4 | 9.1 | 19 | 5.9 | 13 | 13 | 3.6 | 3.9 | 8.3 | 4.7 | 2.8 | 0.9 | 94 | 95 | 95 |
| SakSTAR(F104A) | 14 | 55 | 5.8 | 19 | 4.8 | 14 | 27 | 7.3 | 5.0 | 14 | 4.8 | <0.1 | 0.4 | 7.6 | 3.4 | 1.1 | 1.3 | 95 | 93 | 95 |
| SakSTAR(I106A) | 2 | 93 | 2.3 | 13 | 3.0 | 7.4 | 6.7 | 5.5 | 5.2 | 17 | 11 | 1.4 | 1.8 | 3.1 | 1.8 | 1.2 | 0.5 | 95 | 95 | 95 |
| SakSTAR(T107A) | 32 | 130 | 5.2 | 15 | 3.4 | 9.8 | 10 | 32 | 8.7 | 4.7 | 14 | 1.9 | 3.1 | 6.3 | 3.2 | 5.0 | 0.8 | 94 | 94 | 95 |
| SakSTAR(E108A, K109A) | | 170 | [1.6 | 5.1 | 7.2 | 19 | 5.1 | 28 | 15 | 21 | 21 | 1.2 | 0.43 | 6.9 | 1.4 | 10 | 1.9 | | | |

TABLE 3-continued

Alanine-substitution variants of SakSTAR: Association constants ($K_A \times 10^7$ mol/$L^{-1}$) for binding to insolubilized murine monoclonal antibodies (Mab) and absorption (percent) of antibodies of immunized patient plasma

| | | | murine MAbs | | | | | | | | | | | | | | | | | |
|---|---|---|---|---|---|---|---|---|---|---|---|---|---|---|---|---|---|---|---|---|
| | Exp. | Spec. Act. | Epitope cluster I | | | | | Epitope cluster II | | | | | Epitope cluster III | | | | | SakSTAR patient plasma | | |
| Variant | (mg/L) | (kU/mg) | 17G11 | 26A2 | 30A2 | 2B12 | 3G10 | 18F12 | 14H5 | 28H4 | 32B2 | 7F10 | 7H11 | 25E1 | 40C8 | 24C4 | 1A10 | Pool | Subpool B | Subpool C |
| SakSTAR(F111A) | 5 | 49 | 3.7 | 16 | 3.8 | 13 | 22 | 21 | 8.4 | 12 | 3.1 | 0 8 | 2.8 | 2.9 | 1.5 | 1.5 | 0.9 | 95 | 95 | 95 |
| SakSTAR(V112A, V113A) | 64 | 130 | 4.2 | 16 | 3.9 | 10 | 12 | 34 | 5.8 | 13 | 8.0 | 0.3 | 1.5 | 4.3 | 2.3 | 3.0 | 0.8 | 95 | 95 | 95 |
| SakSTAR(D115A, S117A) | 80 | 54 | 3.3 | 14 | 4.1 | 15 | 15 | 17 | 3.4 | 19 | 0.7 | <0.1 | 1.5 | 4.8 | 2.6 | 1.3 | 0.9 | 95 | 95 | 95 |
| SakSTAR(D115A, E118A, H119A) | | 32 | [2.5 | 32 | 3.4 | 21 | 8.7 | 13 | 9.9 | 23 | 9.3 | 1.2 | 1.0 | 24 | 2.1 | 9.0 | 1.8 | | | |
| SakSTAR(L116A, S117A) | 25 | <5 | 4.4 | 35 | 3.6 | 33 | 42 | 160 | 29 | 220 | <0.1 | <0.1 | 0.5 | 4.1 | 4.9 | 3.5 | 1.6 | 94 | 95 | 95 |
| SakSTAR(H119A, K121A) | | 130 | [8.0 | 24 | 11 | 26 | 29 | 25 | 14 | 29 | 12 | 0.52 | 1.2 | 11 | 2.9 | 20 | 1.2 | | | |
| SakSTAR(I120A) | 26 | 75 | 23 | 26 | 5.1 | 17 | 16 | 30 | 9.8 | 25 | 9.0 | 6 9 | 3.0 | 15 | 5.1 | 5.2 | 1.0 | 93 | 95 | 95 |
| SakSTAR(N122A) | 5 | 19 | NT | | | | | | | | | | | | | | | 95 | 93 | 95 |
| SakSTAR(F125A) | 3 | <10 | 2 8 | 18 | 4.7 | 11 | 18 | 17 | 3 2 | 6.0 | 1.9 | <0.1 | 0.3 | 5.3 | 2.1 | 0.9 | 1.6 | 93 | 90 | 95 |
| SakSTAR(N126V) | 11 | 51 | 7.6 | 13 | 2.0 | 12 | 13 | 30 | 58 | 290 | 9.8 | 2.5 | 1 8 | 8 0 | 4.2 | 6.5 | 0.7 | 95 | 95 | 95 |
| SakSTAR(L127A) | 11 | 54 | 8.9 | 6.7 | 1.8 | 5.0 | 6.6 | 25 | 4 9 | 14 | 8.4 | 1.5 | 0.9 | 1.9 | 0.9 | 2.5 | 1.8 | 93 | 94 | 95 |
| SakSTAR(I128A) | 10 | 20 | 16 | 25 | 4.8 | 15 | 14 | 38 | 2.6 | 4.3 | 8.2 | 2.9 | 2 5 | 2.0 | 4 2 | 6.7 | 0.9 | 95 | 93 | 95 |
| SakSTAR(T129A) | 44 | 190 | 5.3 | 15 | 2.3 | 14 | 24 | 21 | 13 | 15 | 4.2 | 2.3 | 0.7 | 10 | 3.3 | 1.3 | 1.0 | 95 | 95 | 95 |
| SakSTAR(K130A) | 130 | 280 | 5.1 | 12 | 3.2 | 6.4 | 3.5 | 22 | 6.7 | 11 | 15 | 2.7 | <0.1 | <0.1 | 4.1 | 0.9 | 0.6 | 92 | 74 | 71 |
| SakSTAR(V131A) | 130 | 70 | 6.5 | 17 | 2.9 | 11 | 13 | 19 | 14 | 19 | 29 | 3.4 | 1.9 | 13 | 5.3 | 8 6 | 0.9 | 95 | 95 | 95 |
| SakSTAR(V132A) | 100 | 130 | 4.2 | 15 | 2.6 | 9.2 | 11 | 33 | 12 | 30 | 19 | 2.1 | 2.1 | 3.6 | <0.1 | 2.6 | 0.4 | 95 | 95 | 95 |
| SakSTAR(I133A) | 3 | 99 | 9.4 | 15 | 1.9 | 7.8 | 7.8 | 24 | 6.0 | 9.1 | 8.6 | 1.4 | 0.56 | 6.4 | 1.6 | 1.6 | 0.9 | 95 | 95 | 95 |
| SakSTAR(E134A, K135A, K136A) | | 74 | [22 | 21 | 6.7 | 25 | 25 | >18 | >25 | >15 | >12 | 1 7 | 0.2 | 11 | 0.94 | 6.0 | 2.6] | | | |
| SakSTAR(K135A) | 54 | 410 | 5.2 | 12 | 11 | 7.9 | 11 | 20 | 11 | 11 | 3.8 | 2.0 | 1.6 | 6.9 | 3.7 | 1.9 | 0.9 | 95 | 95 | 95 |
| SakSTAR(K136A) | | 180 | 7.6 | 18 | 5.6 | 12 | 13 | 54 | 5.3 | 12 | 16 | 3.2 | 3 5 | 8 6 | 3.9 | 1.8 | 0.5 | 91 | 83 | 95 |

LE: expression level below 3 mg/L

TABLE 4

Mutagenesis of S34, G36 and H43: Association constants ($K_A \times 10^7$ mol/$L^{-1}$) for binding to insolubilized murine monoclonal antibodies (Mab) and absorption (percent) of antibodies of immunized patient plasma

| | | | murine MAbs | | | | | | | | | |
|---|---|---|---|---|---|---|---|---|---|---|---|---|
| | Exp. | Spec. Act. | Epitope cluster I | | | | | Epitope cluster II | | | | |
| Variant | (mg/L) | (kU/mg) | 17G11 | 26A2 | 30A2 | 2B12 | 3G10 | 18F12 | 14H5 | 28H4 | 32B2 | 7F10 |
| SakSTAR | | 120 | 9.3 | 13 | 2.9 | 7.8 | 11 | 38 | 7.4 | 19 | 7.7 | 2.4 |
| SakSTAR(S34G, G36R, H43R) | | 120 | 10 | 14 | 3.3 | 7.5 | 11 | <0.1 | <0.1 | <0.1 | 20 | 2.7 |
| SakSTAR(S34A) | 29 | 110 | 17 | 24 | 4.6 | 9.5 | 11 | 28 | 11 | 22 | 15 | 2.9 |
| SakSTAR(G36A) | 14 | 72 | 3.5 | 9.8 | 1.5 | 5.7 | 6.5 | 52 | 4.2 | 17 | 9.2 | 1.4 |
| SakSTAR(G36E) | 12 | 66 | 3.1 | 8.7 | 1.4 | 4.8 | 4.7 | 12 | 2.8 | 6.1 | 7.6 | 1.0 |
| SakSTAR(G36K) | 34 | 88 | 9.9 | 2320 | 3.1 | 8.3 | 9.8 | 21 | 3.9 | 13 | 15 | 3.0 |
| SakSTAR(G36L) | 15 | 92 | 3.6 | 11 | 1.8 | 6.1 | 6.1 | 16 | 1.4 | 6.4 | 12 | 1.3 |
| SakSTAR(G36N) | 10 | 91 | 8.7 | 10 | 1.6 | 6.1 | 6.2 | 33 | 3.3 | 7.8 | 7.9 | 1.8 |
| SakSTAR(G36Q) | 21 | 92 | 10 | 12 | 1.8 | 6.7 | 6.5 | 23 | 3.8 | 7.5 | 7.3 | 1.5 |
| SakSTAR(G36R) | 45 | 100 | 11 | 2.4 | 3.3 | 10 | 10 | 27 | 4.6 | 14 | 20 | 3.4 |
| SakSTAR(H43A) | 37 | 69 | 15 | 2825 | 9.7 | 18 | 7.6 | <0.1 | <0.1 | <0.1 | 9.1 | 1.5 |
| SakSTAR(H43R) | 43 | 120 | 15 | 11 | 2.7 | 7.6 | 11 | <0.1 | <0.1 | <0.1 | 13 | 6.4 |
| SakSTAR(S34G, G36R) | 45 | 90 | 3.1 | 12 | 2.3 | 4.8 | 4.2 | 13 | 8.3 | 24 | 9.1 | 1.9 |
| SakSTAR(S34G, G36R, H43R, K74A) | 1 | 12 | 12 | 4.7 | 3.8 | 7.4 | 9.4 | <0.1 | 0.1 | 0.6 | 25 | 2.3 |
| SakSTAR(S34G, G36R, K74A) | 15 | 2640 | 2.1 | <0.1 | 1.8 | 0.6 | 10 | 2.2 | 15 | 13 | 1.8 | |
| SakSTAR(K35G, G36R, H43D) | 32 | 6 | 1.8 | 1.5 | 1.6 | 2.0 | 8.9 | <0.1 | <0.1 | <0.1 | 7.1 | 1.3 |
| SakSTAR(G36R, K74A) | 40 | 35 | 19 | 7.0 | 0.2 | 4.3 | 2.0 | 53 | 27 | 28 | 19 | 4.4 |
| SakSTAR(G36R, K74R) | 68 | 150 | 4.7 | 17 | 3.8 | 11 | 8.0 | 16 | 6.0 | 6.4 | 3.0 | 1.6 |
| SakSTAR(G36R, K74A, N95A) | 11 | 25 | 6.1 | 2.9 | 2.9 | 2.4 | <0.1 | 31 | 5.7 | 12 | 5.3 | 4.1 |
| SakSTAR(G36R, K74A, K135R) | 20 | 33 | 5.8 | 3.4 | <0.1 | 1.7 | 0.7 | 26 | 16 | 14 | 17 | 1.2 |
| SakSTAR(G36R, K74R, K135R) | 48 | 75 | 6.1 | 17 | 5.8 | 10 | 3.3 | 31 | 14 | 13 | 5.7 | 2.3 |

| | murine MAbs | | | | | | | |
|---|---|---|---|---|---|---|---|---|
| | Epitope cluster III | | | | | SakSTAR patient plasma | | |
| | 7H11 | 25E1 | 40C8 | 24C4 | 1A10 | Pool | Subpool B | Subpool C |
| SakSTAR | 4.0 | 14 | 5.4 | 2.9 | 0.6 | 95 | 95 | 95 |
| SakSTAR(S34G, G36R, H43R) | <0.1 | <0.1 | <0.1 | 0.15 | 1.7 | 87 | 76 | 75 |
| SakSTAR(S34A) | 3.1 | 8.8 | 3.8 | 2.0 | 0.2 | 95 | 95 | 93 |
| SakSTAR(G36A) | <0.1 | <0.1 | 0.9 | 5.0 | 1.0 | 86 | 83 | 78 |
| SakSTAR(G36E) | <0.1 | <0.1 | <0.1 | 3.4 | 1.1 | 89 | 83 | 72 |
| SakSTAR(G36K) | <0.1 | <0.1 | <0.1 | 2.6 | 1.2 | 88 | 80 | 69 |
| SakSTAR(G36L) | <0.1 | <0.1 | <0.1 | 0.6 | 1.1 | 93 | 85 | 72 |
| SakSTAR(G36N) | <0.1 | <0.1 | 1.0 | 0.3 | 0.5 | 86 | 80 | 75 |
| SakSTAR(G36Q) | <0.1 | <0.1 | <0.1 | 0.1 | 0.4 | 87 | 84 | 73 |
| SakSTAR(G36R) | <0.1 | <0.1 | <0.1 | 3.1 | 1.2 | 89 | 81 | 70 |
| SakSTAR(H43A) | 2.0 | 23 | 7.8 | 7.2 | 1.6 | 95 | 95 | 95 |
| SakSTAR(H43R) | 0.7 | 18 | 6.7 | 5.7 | 1.4 | 95 | 95 | 95 |
| SakSTAR(S34G, G36R) | <0.1 | <0.1 | <0.1 | <0.1 | 0.6 | 92 | 83 | 69 |
| SakSTAR(S34G, G36R, H43R, K74A) | <0.1 | <0.1 | 0.5 | 0.8 | 1.7 | 67 | 56 | 83 |
| SakSTAR(S34G, G36R, K74A) | <0.1 | <0.1 | <0.1 | 0.3 | 2.2 | 59 | 28 | 68 |
| SakSTAR(K35G, G36R, H43D) | <0.1 | <0.1 | <0.1 | <0.1 | 0.9 | 82 | 75 | 72 |
| SakSTAR(G36R, K74A) | <0.1 | <0.1 | <0.1 | 1.2 | 1.0 | 48 | 33 | 58 |
| SakSTAR(G36R, K74R) | <0.1 | <0.1 | <0.1 | 0.2 | 0.8 | 81 | 54 | 73 |
| SakSTAR(G36R, K74A, N95A) | <0.1 | <0.1 | <0.1 | <0.1 | 0.9 | 53 | 32 | 63 |
| SakSTAR(G36R, K74A, K135R) | <0.1 | <0.1 | <0.1 | 0.4 | 0.5 | 64 | 32 | 68 |
| SakSTAR(G36R, K74R, K135R) | <0.1 | <0.1 | <0.1 | 0.3 | 0.8 | 77 | 49 | 68 |

TABLE 5

Mutagenesis of K35, Y73, K74, E80/D82, N95, K130, V132 and K135: Association constants ($K_A \times 10^7$ mol/$L^{-1}$) for binding to insolubilized murine monoclonal antibodies (Mab) and absorption (percent) of antibodies of immunized patient plasma

| | | | murine MAbs | | | | | | | | | | | | | | | | |
|---|---|---|---|---|---|---|---|---|---|---|---|---|---|---|---|---|---|---|---|
| | | Spec. Act. | Epitope cluster I | | | | | Epitope cluster II | | | | | Epitope cluster III | | | | | SakSTAR patient plasma | | |
| Variant | Exp. (mg/L) | (kU/mg) | 17G11 | 26A2 | 30A2 | 2B12 | 3G10 | 18F12 | 14H5 | 28H4 | 32B2 | 7F10 | 7H11 | 25E1 | 40C8 | 24C4 | 1A10 | Pool | Subpool B | Subpool C |
| SakSTAR | | 120 | 9.3 | 13 | 2.9 | 7.8 | 11 | 38 | 7.4 | 19 | 7.7 | 2.4 | 4.0 | 14 | 5.4 | 2.9 | 0.6 | 95 | 95 | 95 |
| SakSTAR(S34G, G36R, H43R) | | 120 | 10 | 14 | 3.3 | 7.5 | 11 | <0.1 | <0.1 | <0.1 | 20 | 2.7 | <0.1 | <0.1 | <0.1 | 0.15 | 1.7 | 87 | 76 | 75 |
| SakSTAR(K35A) | | 230 | 6.4 | 14 | 3.3 | 8.0 | 7.4 | 31 | 11 | 12 | 11 | 2.6 | <0.1 | 1.3 | 0.2 | 1.7 | 0.8 | 91 | 88 | 95 |
| SakSTAR(K35E) | 75 | 160 | 4.8 | 10 | 0.6 | 2.7 | 2.7 | 21 | 5.7 | 9.1 | 4.8 | 1.0 | <0.1 | <0.1 | <0.1 | 1.5 | 0.4 | 95 | 95 | 92 |
| SakSTAR(K35Q) | 9 | 69 | 3.2 | 9.5 | 1.3 | 5.2 | 5.4 | 22 | 2.7 | 9.3 | 8.5 | 1.2 | 0.5 | 1.7 | <0.1 | 1.9 | 1.0 | 95 | 95 | 95 |
| SakSTAR(Y73A) | 20 | <5 | 9.5 | <0.1 | <0.1 | <0.1 | 4.8 | 33 | 7.3 | 11 | 8.9 | 2.0 | 0.5 | 9.0 | 2.5 | 1.4 | 0.8 | 63 | 44 | 93 |
| SakSTAR(Y73F) | 6 | 31 | 7.9 | 12 | 1.3 | 2.1 | 8.0 | 24 | 15 | 19 | 15 | 2.6 | 1.6 | 6.2 | 3.5 | 7.2 | 1.4 | 93 | 95 | 95 |
| SakSTAR(Y73H) | 30 | <5 | 7.3 | 1.5 | <0.1 | <0.1 | 1.4 | 20 | 7.5 | 17 | 42 | 4.3 | 3.5 | 6.8 | 5.9 | 9.7 | 1.3 | 76 | 65 | 95 |
| SakSTAR(Y73L) | 33 | <5 | 11 | <0.1 | <0.1 | <0.1 | <0.1 | 84 | 19 | 26 | 53 | 3.4 | 4.2 | 7.1 | 4.2 | 3.4 | 1.0 | 81 | 60 | 94 |
| SakSTAR(Y73S) | 31 | <5 | 7.0 | 3.6 | 0.59 | 0.6 | 3.0 | 21 | 8.3 | 14 | 21 | 3.2 | 2.2 | 6.7 | 1.3 | 1.3 | 0.7 | 86 | 69 | 95 |
| SakSTAR(Y73W) | 6 | 27 | 4.8 | 9.0 | 4.6 | 4.6 | 11 | 8.4 | 4.5 | 11 | 8.0 | 2.7 | 2.9 | 5.0 | 3.0 | 3.8 | 1.3 | 73 | 53 | 93 |
| SakSTAR(K74A) | 80 | 69 | 4.4 | 2.7 | 0.2 | 2.2 | 1.1 | 17 | 5.2 | 14 | 7.6 | 2.2 | 2.0 | 6.8 | 3.3 | 1.8 | 0.9 | 64 | 58 | 95 |
| SakSTAR(K74E) | 12 | <5 | 2.2 | 0.6 | <0.1 | 0.7 | 0.1 | 14 | 1.8 | 7.5 | 9.3 | 1.2 | 2.0 | 3.0 | 1.2 | 0.6 | 1.0 | 83 | 43 | 90 |
| SakSTAR(K74N) | 9 | 39 | 2.9 | 4.7 | 1.1 | 3.3 | 1.7 | 10 | 1.6 | 4.8 | 13 | 1.5 | 1.9 | 4.0 | 1.8 | 1.4 | 0.9 | 63 | 46 | 95 |
| SakSTAR(K74Q) | 64 | 110 | 5.3 | 5.8 | <0.1 | 2.5 | 1.1 | 24 | 5.9 | 12 | 5.4 | 1.1 | 2.0 | 6.2 | 2.3 | 2.0 | 0.4 | 70 | 62 | 94 |
| SakSTAR(K74R) | 44 | 150 | 2.1 | 7.5 | 2.0 | 4.1 | 4.2 | 24 | 6.9 | 8.0 | 8.3 | 1.3 | 2.2 | 7.8 | 3.2 | 2.1 | 0.5 | 75 | 70 | 95 |
| SakSTAR(E80A, D82A) | | 130 | 7.3 | 12 | 2.1 | 6.5 | 5.9 | 79 | 6.1 | 8.4 | 7.8 | 1.9 | <0.1 | <0.1 | <0.1 | <0.1 | 0.4 | 89 | 83 | 92 |
| SakSTAR(E80A) | | 160 | 13 | 13 | 3.3 | 7.9 | 10 | 35 | 7.4 | 17 | 8.6 | 2.1 | <0.1 | 16 | 3.6 | <0.1 | 1.7 | 94 | 93 | 95 |
| SakSTAR(D82A) | | 160 | 17 | 12 | 4.8 | 7.3 | 11 | 31 | 7.8 | 17 | 12 | 2.7 | <0.1 | 0.2 | <0.1 | <0.1 | 2.3 | 95 | 93 | 95 |
| SakSTAR(N95A) | 25 | 260 | 10 | 18 | 4.0 | 10 | 11 | 50 | 13 | 14 | 4.9 | 2.3 | 3.7 | 7.3 | 4.7 | 2.9 | 0.8 | 95 | 94 | 95 |
| SakSTAR(N95E) | 12 | 79 | 2.8 | 8.5 | 1.3 | 5.2 | 5.4 | 17 | 2.7 | 10 | 5.2 | 1.1 | 0.5 | 4.0 | 1.7 | 1.8 | 0.6 | 95 | 92 | 95 |
| SakSTAR(N95G) | 20 | 160 | 4.1 | 11 | 1.5 | 6.8 | 7.6 | 36 | 3.3 | 15 | 3.6 | 1.5 | 0.7 | 5.8 | 2.7 | 2.7 | 0.9 | 95 | 90 | 95 |
| SakSTAR(N95K) | 54 | 180 | 9.5 | 14 | 3.2 | 9.0 | 11 | 51 | 5.0 | 18 | 4.8 | 2.5 | 1.6 | 8.3 | 2.9 | 4.8 | 1.1 | 95 | 95 | 95 |
| SakSTAR(N95R) | LE | | | | | | | | | | | | | | | | | | | |
| SakSTAR(K130A) | | 280 | 5.1 | 12 | 3.2 | 6.4 | 3.5 | 22 | 6.7 | 11 | 15 | 2.7 | <0.1 | <0.1 | 4.1 | 0.9 | 0.6 | 92 | 74 | 71 |
| SakSTAR(K130T) | | 290 | 7.8 | 14 | 3.1 | 8.0 | 5.6 | 43 | 5.4 | 9.7 | 17 | 2.7 | <0.1 | <0.1 | 3.4 | 0.5 | 0.5 | 92 | 84 | 82 |
| SakSTAR(V132A) | 102 | 130 | 4.2 | 15 | 2.6 | 9.2 | 11 | 33 | 12 | 30 | 19 | 2.1 | 2.1 | 3.6 | <0.1 | 2.6 | 0.4 | 95 | 95 | 95 |
| SakSTAR(V132L) | 126 | 120 | 4.8 | 14 | 2.3 | 8.0 | 9.7 | 67 | 10 | 48 | 20 | 2.5 | 2.0 | 11 | <0.1 | 4.8 | 0.4 | 95 | 95 | 95 |
| SakSTAR(V132T) | 78 | 140 | 4.5 | 13 | 2.4 | 7.8 | 9.0 | 39 | 10 | 25 | 16 | 2.0 | 1.1 | 2.0 | <0.1 | <0.1 | 0.4 | 95 | 95 | 95 |
| SakSTAR(V132N) | 16 | 150 | 4.5 | 11 | 1.7 | 7.0 | 7.2 | 21 | 17 | 20 | 15 | 2.0 | 1.5 | 1.3 | <0.1 | 4.2 | 0.7 | 95 | 95 | 95 |
| SakSTAR(V132R) | 76 | 230 | 5.4 | 12 | 0.8 | 3.3 | 3.2 | 23 | 5.5 | 7.8 | 4.8 | 1.1 | 2.1 | 3.4 | <0.1 | 0.4 | 0.4 | 95 | 95 | 95 |
| SakSTAR(K135A) | 54 | 410 | 5.2 | 12 | 11 | 7.9 | 11 | 20 | 11 | 11 | 3 8 | 2.0 | 1.6 | 6.9 | 3.7 | 1.9 | 0.9 | 95 | 95 | 95 |
| SakSTAR(K135F) | 68 | 64 | 3.9 | 6.3 | 1.0 | 6.1 | 4.1 | 13 | 4.5 | 8.4 | 16 | 2.1 | 1.6 | 5.8 | 1.9 | 1.5 | 0.9 | 95 | 95 | 95 |
| SakSTAR(K135R) | 54 | 230 | 4.0 | 14 | 1.4 | 9.3 | 5.0 | 31 | 8.1 | 13 | 23 | 1.9 | 2.4 | 2.4 | 2.6 | 2.1 | 0.5 | 95 | 95 | 95 |
| SakSTAR(K35A, K74A) | 20 | 130 | NT | | | | | | | | | | | | | | | | | |
| SakSTAR(Y73A, K74A) | 24 | <5 | 18 | <0.1 | <0.1 | <0.1 | <0.1 | 19 | 6 7 | 23 | 9.9 | 3.2 | 2 7 | 13 | 4.0 | 1.6 | 1.1 | 47 | 28 | 87 |
| SakSTAR(Y73F, K74A) | 21 | 6 | 17 | 6.7 | <0.1 | 2.1 | <0.1 | 42 | 19 | 21 | 20 | 4.9 | 1.9 | 2.8 | 6.6 | 2 1 | 0 8 | 51 | 34 | 90 |
| SakSTAR(I60A, K74A, N95A) | | 84 | 5.3 | 2.7 | <0.1 | 2.5 | 5.3 | 17 | 7.2 | 9.6 | 3.4 | 2.3 | 2.1 | 6.2 | 2.7 | 2 9 | 0.8 | 60 | 47 | 95 |
| SakSTAR(N95A, K135R) | 120 | 240 | 4.9 | 13 | 1.9 | 9.0 | 9.9 | 18 | 12 | 15 | 2.5 | 1.5 | 1.8 | 5.9 | 3.6 | 3 7 | 0.8 | 95 | 95 | 95 |
| SakSTAR(K130T, K135R) | 15 | 280 | 3.7 | 10 | 1.6 | 7.2 | 8 0 | 13 | 7.7 | 4.5 | 3 7 | 1.6 | <0.1 | <0.1 | 2.4 | 0.4 | 0 6 | 89 | 60 | 73 |

TABLE 6

Combination mutants of SakSTAR(K130T, K135R) with K35A, G36R, E65X, K74X and selected other amino acids

| | | | murine MAbs | | | | | | | | | | | | | | | SakSTAR patient plasma | | | | |
|---|---|---|---|---|---|---|---|---|---|---|---|---|---|---|---|---|---|---|---|---|---|---|
| | Exp. | Spec. Act. | Epitope cluster I | | | | | Epitope cluster II | | | | | Epitope cluster III | | | | | Pool | Subpool | Subpool | Pool | |
| Variant | (mg/mL) | (kU/mg) | 17G11 | 26A2 | 30A2 | 2B12 | 3G10 | 18F12 | 14H5 | 28H4 | 32B2 | 7F10 | 7H11 | 25E1 | 40C8 | 24C4 | 1A10 | 10 | B | C | 40 | Code |
| SakSTAR(K130T, K135R) | 15 | 280 | 3.7 | 10 | 1.6 | 7.2 | 8.0 | 13 | 7.7 | 4.5 | 3.7 | 1.6 | <0.1 | <0.1 | 2.4 | 0.4 | 0.6 | 89 | 60 | 73 | 90 | SY2 |
| SakSTAR(G36R, K130T, K135R) | 26 | 220 | 7.2 | 18 | 2.8 | 11 | 14 | 17 | 3.9 | 8.9 | 5.1 | 1.6 | <0.1 | <0.1 | <0.1 | <0.1 | 1.1 | 79 | 65 | 69 | — | SY3 |
| SakSTAR(K74R, K130T, K135R) | 18 | 310 | 7.3 | 27 | 5.9 | 16 | 18 | 17 | 3.7 | 11 | 5.1 | 1.5 | <0.1 | <0.1 | 3.2 | 0.7 | 0.9 | 76 | 49 | 69 | 78 | SY4 |
| SakSTAR(K74Q, K130T, K135R) | 64 | 190 | 4.0 | 7.2 | 3.0 | 7.7 | 0.9 | 20 | 5.7 | 7.2 | 8.4 | 1.8 | <0.1 | <0.1 | 2.7 | 0.7 | 1.0 | 50 | 25 | 67 | 62 | SY41 |
| SakSTAR(G36R, K74R, K130T, K135R) | 5 | 210 | 7.6 | 26 | 5.7 | 17 | 19 | 17 | 4.7 | 10 | 5.0 | 1.4 | <0.1 | <0.1 | <0.1 | <0.1 | 0.8 | 73 | 44 | 69 | 75 | SY5 |
| SakSTAR(G36R, K74Q, K130T, K135R) | 88 | 120 | 5.5 | 7.3 | 0.8 | 11 | 6.4 | 35 | 11 | 7.1 | 6.1 | 2.6 | <0.1 | <0.1 | <0.1 | <0.1 | 0.8 | 51 | 25 | 63 | 54 | SY42 |
| SakSTAR(G36R, H43R, K74R, K130T, K135R) | 29 | 160 | 5.6 | 8.8 | 2.2 | 10 | 10 | <0.1 | <0.1 | <0.1 | 6.3 | 2.0 | <0.1 | <0.1 | <0.1 | <0.1 | 0.9 | 72 | 39 | 69 | — | SY9 |
| SakSTAR(S34G, G36R, K74Q, K130T, K135R) | 40 | 76 | 4.8 | 5.9 | 0.5 | 13 | 1.5 | 18 | 8.7 | 7.5 | 5.1 | 2.1 | <0.1 | <0.1 | <0.1 | <0.1 | 1.1 | 52 | 25 | 65 | 61 | SY43 |
| SakSTAR(E65A, K74Q, K130T, K135R) | 46 | 170 | 11 | 9.0 | 2.3 | 11 | 13 | 19 | 66 | 12 | 5.7 | 2.3 | <0.1 | <0.1 | 3.5 | 1.2 | 0.6 | 45 | 16 | 77 | 55 | SY48 |
| SakSTAR(G36R, E65A, K74Q, K130T, K135R) | 80 | 83 | 4.7 | 12 | 1.2 | 16 | 21 | 27 | 12 | 10 | 6.9 | 2.6 | <0.1 | <0.1 | <0.1 | <0.1 | 0.7 | 44 | 18 | 65 | 46 | SY44 |
| SakSTAR(G36R, E65A, K74A, K130A, K135R) | 17 | 71 | 5.7 | 10 | 1.8 | 13 | 12 | 21 | 8.4 | 6.9 | 4.6 | 1.8 | <0.1 | <0.1 | <0.1 | <0.1 | 1.0 | 41 | 14 | 64 | 50 | SY59 |
| SakSTAR(E65A, A72S, K74Q, K130T, K135R) | 60 | 96 | 5.6 | 6.0 | 2.0 | 3.6 | 4.9 | 21 | 8.6 | 8.8 | 2.8 | 2.5 | <0.1 | <0.1 | 3.5 | 1.7 | 1.1 | 51 | 13 | 66 | 56 | SY51 |
| SakSTAR(E65Q, K74Q, K130T, K135R) | 40 | 150 | 6.7 | 18 | 2.1 | 15 | 16 | 9.0 | 3.1 | 4.1 | 6.3 | 2.3 | <0.1 | <0.1 | 3.8 | 0.9 | 0.6 | 53 | 29 | 67 | 65 | SY49 |
| SakSTAR(K74Q, K86A, K130T, K135R) | 54 | 130 | 2.4 | 4.9 | <0.1 | 7.4 | 3.8 | 19 | 8.7 | 7.6 | 4.7 | 1.9 | <0.1 | <0.1 | 3.5 | 1.3 | 1.5 | 56 | 32 | 69 | 61 | SY55 |
| SakSTAR(E65Q, T71S, K74Q, K130T, K135R) | 32 | 210 | 6.2 | 13 | 1.8 | 10 | 13 | 11 | 3.9 | 5.0 | 68 | 23 | <0.1 | <0.1 | 3.1 | 1.1 | 0.8 | 49 | 21 | 64 | 59 | SY65 |
| SakSTAR(E65Q, K74Q, E75A, K130T, K135R) | 36 | 46 | 7.7 | <0.1 | <0.1 | <0.1 | <0.1 | 10 | 3.9 | 3.2 | 7.4 | 2.6 | <0.1 | <0.1 | 4.6 | 1.3 | 0.6 | 43 | 15 | 62 | 55 | SY66 |
| SakSTAR(E65Q, K74Q, E75D, K130T, K135R) | 35 | 67 | 7.0 | <0.1 | <0.1 | <0.1 | <0.1 | 13 | 5.4 | 4.9 | 6.6 | 2.5 | <0.1 | <0.1 | 3.2 | 1.3 | 1.0 | 49 | 29 | 63 | 57 | SY67 |
| SakSTAR(K74Q, K130T, K135R, K136A, +137A) | 19 | 78 | 4.3 | 24 | <0.1 | 2.7 | 5.6 | 20 | 9.6 | 7.5 | 5.6 | 2.2 | <0.1 | <0.1 | 1.7 | 1.1 | 1.2 | 37 | 12 | 57 | 50 | SY68 |
| SakSTAR(K74Q, K130A, K135R) | 28 | 240 | 5.6 | 5.4 | 0.5 | 7.5 | 5.3 | 21 | 8.4 | 14 | 6.1 | 2.4 | <0.1 | <0.1 | 4.1 | 2.6 | 0.7 | 57 | 27 | 78 | 65 | SY56 |
| SakSTAR(E65Q, K74Q, K130A, K135R) | 60 | 230 | 6.0 | 14 | 2.4 | 15 | 17 | 9.0 | 3.3 | 5.8 | 6.3 | 2.3 | <0.1 | <0.1 | 4.3 | 2.0 | 0.6 | 51 | 32 | 73 | 58 | SY69 |
| SakSTAR(K74Q, K130E, K135R) | 46 | 300 | 4.1 | 4.4 | 0.8 | 6.6 | 3.8 | 18 | 8.5 | 7.8 | 5.2 | 2.1 | <0.1 | <0.1 | 2.4 | 0.7 | 0.9 | 55 | 29 | 64 | 59 | SY57 |
| SakSTAR(E65Q, K74Q, K130A, K135A) | 88 | 170 | 5.3 | 8.9 | 1.7 | 7.7 | 11 | 16 | 3.4 | 5.8 | 6.2 | 2.4 | <0.1 | <0.1 | 3.5 | 2.4 | 0.7 | 55 | 27 | 79 | 55 | SY70 |
| SakSTAR(K74Q, K130E, V132R, K135R) | 68 | 170 | 4.5 | 4.9 | 0.4 | 6.0 | 5.2 | 9.0 | 4.9 | 4.3 | 5.6 | 2.4 | <0.1 | <0.1 | <0.1 | <0.1 | 0.6 | 51 | 20 | 63 | 56 | SY58 |
| SakSTAR(E65Q, K74Q, T90A, K130A, K135R) | 36 | 170 | 6.2 | 13 | 1.8 | 12 | 14 | 7.3 | 2.5 | 3.8 | <0.1 | <0.1 | <0.1 | <0.1 | 4.1 | 1.9 | 0.5 | 51 | 27 | 69 | 57 | SY71 |
| SakSTAR(E65Q, K74Q, N95A, K130A, K135R) | 40 | 220 | 6.1 | 14 | 1.9 | 17 | 15 | 9.0 | 3.3 | 5.8 | 6.3 | 2.3 | <0.1 | <0.1 | 4.1 | 2.2 | 0.5 | 52 | 29 | 74 | 58 | SY72 |
| SakSTAR(E65Q, K74Q, E118A, K130A, K135R) | 86 | 180 | 8.5 | 18 | 2.8 | 15 | 27 | 11 | 4.1 | 5.7 | 7.3 | 2.6 | <0.1 | <0.1 | 6.1 | 2.8 | 0.5 | 50 | 28 | 72 | 58 | SY73 |
| SakSTAR(E65Q, K74Q, N95A, E118A, K130A, K135R) | 33 | 190 | 7.8 | 18 | 2.4 | 7.7 | 21 | 20 | 3.9 | 6.1 | 6.6 | 2.3 | <0.1 | <0.1 | 5.8 | 2.5 | 0.5 | 48 | 27 | 74 | 58 | SY74 |
| SakSTAR(N95A, K130A, K135R) | 85 | 410 | 6.1 | 11 | 3.3 | 18 | 15 | 37 | 5.9 | 9.6 | 6.8 | 2.5 | <0.1 | <0.1 | 4.5 | 3.0 | 0.6 | 93 | 81 | 82 | 94 | INT1 |
| SakSTAR(K35A, E65Q, K74Q, K130A, K135R) | 29 | 110 | NT | | | | | | | | | | | | | | | 49 | 26 | 63 | 45 | SY75 |
| SakSTAR(K35A, H43R, E65Q, K74Q, K130A, K135R) | | 14 | NT | | | | | | | | | | | | | | | 49 | 23 | 73 | 55 | SY76 |
| SakSTAR(E65Q, K74Q, S103A, K130A, K135R) | 32 | 60 | 6.7 | 15 | 2.6 | 14 | 16 | 8.0 | 2.7 | 3.9 | 6.3 | 2.3 | <0.1 | <0.1 | 4.6 | 1.6 | 0.6 | 55 | 27 | 75 | 61 | SY77 |
| SakSTAR(T21A, K35A, E65Q, K74Q, K130A, K135R) | | 110 | NT | | | | | | | | | | | | | | | 50 | 26 | 72 | 50 | SY78 |
| SakSTAR(T56A, E65Q, K74Q, K130T, K135R) | | 180 | NT | | | | | | | | | | | | | | | 52 | 31 | 61 | 55 | SY79 |
| SakSTAR(K57A, E58A, E61A, K74Q, K130T, K135R) | | 120 | NT | | | | | | | | | | | | | | | 57 | 24 | 61 | 54 | SY80 |
| SakSTAR(E65Q, K74Q, K109A, K130T, K135R) | 40 | 210 | 7.3 | 15 | 2.1 | 12 | 12 | 14 | 2.5 | 4.0 | 5.8 | 2.3 | <0.1 | <0.1 | 3.4 | 1.8 | 0.7 | 50 | 22 | 68 | 51 | SY81 |
| SakSTAR(E65Q, K74Q, E108A, K130T, K135R) | | 120 | | | | | | | | | | | | | | | | 51 | 24 | 61 | 54 | SY82 |
| SakSTAR(E65Q, K74Q, E108A, K109A, K130T, K135R) | 62 | 180 | 9.3 | 13 | 1.4 | 13 | 17 | 17 | 3.0 | 4.1 | 6.8 | 2.5 | <0.1 | <0.1 | 3.7 | 2.6 | 0.5 | 55 | 21 | 67 | 50 | SY83 |

TABLE 6-continued

Combination mutants of SakSTAR(K130T, K135R) with K35A, G36R, E65X, K74X and selected other amino acids

| | | | murine MAbs | | | | | | | | | | | | | | | SakSTAR patient plasma | | | | |
|---|---|---|---|---|---|---|---|---|---|---|---|---|---|---|---|---|---|---|---|---|---|---|
| | Exp. | Spec. Act. | Epitope cluster I | | | | | Epitope cluster II | | | | | Epitope cluster III | | | | | Pool | Subpool | Subpool | Pool | |
| Variant | (mg/mL) | (kU/mg) | 17G11 | 26A2 | 30A2 | 2B12 | 3G10 | 18F12 | 14H5 | 28H4 | 32B2 | 7F10 | 7H11 | 25E1 | 40C8 | 24C4 | 1A10 | 10 | B | C | 40 | Code |
| SakSTAR(E65Q, K74Q, K121A, K130T, K135R) | 73 | 150 | 5.7 | 13 | 1.5 | 11 | 14 | 22 | 3.1 | 4.6 | 1.2 | <0.1 | <0.1 | <0.1 | 3.5 | 1.8 | 0.9 | 61 | 25 | 69 | 57 | SY85 |
| SakSTAR(E19A, E65Q, K74Q, K130T, K135R) | | 3 | NT | | | | | | | | | | | | | | | 51 | 27 | 62 | 56 | SY86 |
| SakSTAR(E65Q, K74Q, D115A, K130T, K135R) | | 57 | NT | | | | | | | | | | | | | | | 52 | 25 | 62 | | SY87 |
| SakSTAR(G36R, E65A, K74Q, K130E, V132R, K135R) | 48 | 60 | 7.6 | 9.9 | 1.4 | 11 | 14 | 42 | 19 | 17 | 4.3 | 1.0 | <0.1 | <0.1 | <0.1 | <0.1 | 0.9 | 44 | 17 | 70 | 44 | SY60 |
| SakSTAR(E65Q, K74Q, N95A, E118A, K130A, K135R, +137A) | | 120 | | | | | | | | | | | | | | | | 45 | 30 | 74 | 60 | SY93 |
| SakSTAR(E65Q, K74Q, N95A, E118A, K130A, K135R, K136A, +137K) | | 1,400 | | | | | | | | | | | | | | | | 37 | 16 | 70 | 54 | SY94 |

Association constants ≧ 10-fold lower and antibody absorption ≦60 percent of wild-type SakSTAR are represented in bold type; ≧100,000 HU/mg represented in bold type. NT: not tested.

TABLE 7

Combination mutants of SakSTAR(E80A, D82A, K130T, K135R) with K35A, G36R, E65X, K74X, and selected other amino acids

| | Exp. | | murine MAbs | | | | | | | | | | | | | | | SakSTAR patient plasma | | | | |
|---|---|---|---|---|---|---|---|---|---|---|---|---|---|---|---|---|---|---|---|---|---|---|
| | (mg/ | Spec. Act. | Epitope cluster I | | | | | Epitope cluster II | | | | | Epitope cluster III | | | | | Pool | Subpool | Subpool | Pool | |
| Variant | mL) | (kU/mg) | 17G11 | 26A2 | 30A2 | 2B12 | 3G10 | 18F12 | 14H5 | 28H4 | 32B2 | 7F10 | 7H11 | 25E1 | 40C8 | 24C4 | 1A10 | 10 | B | C | 40 | Code |
| SakSTAR(E80A, D82A, K130T, K135R) | 20 | 250 | 8.4 | 17 | 3.1 | 11 | 13 | 18 | 4.3 | 11 | 5.5 | 1.5 | <0.1 | <0.1 | <0.1 | <0.1 | 1.0 | 80 | 64 | 68 | | SY6 |
| SakSTAR(K74R, E80A, D82A, K130T, K135R) | 4 | 220 | 5.3 | 31 | 2.8 | 18 | 11 | 89 | 8.4 | 21 | 5.9 | 1.8 | <0.1 | <0.1 | <0.1 | <0.1 | 0.6 | 74 | 34 | 69 | 72 | SY7 |
| SakSTAR(K74Q, E80A, D82A, K130T, K135R) | 27 | 110 | 5.1 | 6.5 | 1.2 | 7.9 | 7.3 | 28 | 6.4 | 19 | 4.6 | 1.7 | <0.1 | <0.1 | <0.1 | <0.1 | 0.8 | 46 | 17 | 60 | 48 | SY15 |
| SakSTAR(K35A, K74R, E80A, D82A, K130T, K135R) | 70 | 160 | 5.9 | 5.7 | 6.4 | 2.7 | 18 | 19 | 16 | 8.2 | 9.0 | 1.8 | <0.1 | <0.1 | <0.1 | <0.1 | 0.8 | 66 | 34 | 66 | 68 | SY17 |
| SakSTAR(E65D, K74R, E80A, D82A, K130T, K135R) | 22 | 140 | 5.4 | 50 | 2.9 | 49 | 21 | 31 | 11 | 37 | 3.4 | 1.8 | <0.1 | <0.1 | <0.1 | <0.1 | 0.6 | 43 | 11 | 68 | 57 | SY19 |
| SakSTAR(E65S, K74R, E80A, D82A, K130T, K135R) | 3 | 110 | 3.2 | 12 | 4.6 | 44 | 15 | 19 | 5 0 | 15 | 6.6 | 1.4 | <0.1 | <0.1 | <0.1 | <0.1 | 0.4 | 35 | 12 | 60 | — | SY20 |
| SakSTAR(E65T, K74R, E80A, D82A, K130T, K135R) | 30 | 94 | 7.2 | 9.3 | 9.9 | 5.6 | 32 | 22 | 15 | 8.2 | 11 | 2.0 | <0.1 | <0.1 | <0.1 | <0.1 | 1.0 | 58 | 24 | 69 | — | SY21 |
| SakSTAR(S34G, G36R, K74R, K130T, K135R) | | 250 | 5.6 | 54 | 2.9 | 38 | 25 | 36 | 6.5 | 18 | 5.5 | 1.9 | <0.1 | <0.1 | <0.1 | <0.1 | 0.9 | 75 | 33 | 68 | — | SY10 |
| SakSTAR(E65A, K74R, E80A, D82A, K130T, K135R) | 40 | 140 | 8.2 | 10 | 13 | 5.7 | 55 | 24 | 22 | 11 | 15 | 2.2 | <0.1 | <0.1 | <0.1 | <0.1 | 1.0 | 51 | 17 | 66 | — | SY18 |
| SakSTAR(E65N, K74R, E80A, D82A, K130T, K135R) | 88 | 120 | 8.5 | 12 | 11 | 7.0 | 36 | 43 | 13 | 12 | 7.9 | 2.4 | <0.1 | <0.1 | <0.1 | <0.1 | 0.9 | 60 | 29 | 67 | — | SY23 |
| SakSTAR(E65Q, K74R, E80A, D82A, K130T, K135R) | 55 | 140 | 9.0 | 16 | 16 | 9.9 | 59 | 18 | 4.5 | 4.3 | 10 | 2.5 | <0.1 | <0.1 | <0.1 | <0.1 | 0.8 | 54 | 22 | 63 | 60 | SY22 |
| SakSTAR(K57A, E58A, E61A, E80A, D82A, K130T, K135R) | 24 | 110 | 2.4 | 17 | 2.9 | 13 | 12 | 16 | 7.8 | 16 | 4.5 | 1.6 | <0.1 | <0.1 | <0.1 | <0.1 | 0.7 | 75 | 64 | 62 | 74 | SY13 |
| SakSTAR(E65A, A72S, K74R, E80A, D82A, K130T, K135R) | 92 | 62 | 8.2 | 23 | 3.8 | 8.4 | 19 | 30 | 11 | 13 | 3.6 | 3.1 | <0.1 | <0.1 | <0.1 | <0.1 | 1.2 | 51 | 13 | 66 | 52 | SY53 |
| SakSTAR(E65D, K74Q, E80A, D82A, K130T, K135R) | 84 | 110 | 7.0 | 3.9 | 2.6 | 4.1 | 7.2 | 29 | 28 | 14 | 6.8 | 2.2 | <0.1 | <0.1 | <0.1 | <0.1 | 0.9 | 43 | 13 | 64 | 42 | SY30 |
| SakSTAR(E65Q, K74Q, E80A, D82A, K130T, K135R) | 54 | 120 | 5.1 | 16 | 3.2 | 14 | 3.7 | 16 | 20 | 2.4 | 5.7 | 1.7 | <0.1 | <0.1 | <0.1 | <0.1 | 1.0 | 43 | 21 | 64 | 42 | SY47 |
| SakSTAR(K35A, E65D, K74Q, E80A, D82A, K130T, K135R) | 56 | 140 | 5.1 | 6.8 | 2.6 | 9.5 | 1.7 | 28 | 17 | 14 | 8.4 | 21 | <0.1 | <0.1 | <0.1 | <0.1 | 1.0 | 35 | 8 | 58 | 40 | SY46 |
| SakSTAR(K74R, E80A, D82A, S103A, K130T, K135R) | 32 | 160 | 4.9 | 22 | 5.8 | 14 | 4.3 | 26 | 6.9 | 7.4 | 5.0 | 1.7 | <0.1 | <0.1 | <0.1 | <0.1 | 0.9 | 67 | 32 | 69 | 70 | SY24 |
| SakSTAR(K35A, E65D, K74R, E80A, D82A, E108A, K109A, K130T, K135R) | 9.0 | 89 | 5.8 | 30 | 2.6 | 26 | 10 | 13 | 16 | 13 | 3.2 | 1.8 | <0.1 | <0.1 | <0.1 | <0.1 | 0.5 | 55 | 10 | 63 | 47 | SY12 |
| SakSTAR(K35A, E65D, K74R, E80A, D82A, E108A, K130T, K135R) | 20 | 91 | 6.4 | 20 | 5.0 | 15 | 3.9 | 22 | 17 | 7.4 | 2.4 | 1.9 | <0.1 | <0.1 | <0.1 | <0.1 | 0.9 | 44 | 8 | 70 | 53 | SY32 |
| SakSTAR(E65D, K74R, E80A, D82A, E108A, K130T, K135R) | 4 | 90 | 8.1 | 6.7 | 6.9 | 4.3 | 29 | 19 | 31 | 11 | 14 | 2.1 | <0.1 | <0.1 | <0.1 | <0.1 | 1.0 | 52 | 11 | 69 | — | SY33 |
| SakSTAR(K35A, E65D, K74R, E80A, D82A, K109A, K130T, K135R) | 42 | 84 | 5.5 | 18 | 5.3 | 14 | 1.6 | 18 | 12 | 7.7 | 10 | 1.7 | <0.1 | <0.1 | <0.1 | <0.1 | 1.0 | 43 | 6 | 61 | 50 | SY36 |
| SakSTAR(E65D, K74R, E80A, D82A, K109A, K130T, K135R) | 60 | 130 | 9.7 | 6.6 | 6.8 | 4.2 | 28 | 11 | 32 | 12 | 17 | 2.3 | <0.1 | <0.1 | <0.1 | <0.1 | 0.9 | 56 | 10 | 64 | 53 | SY37 |
| SakSTAR(K35A, E65D, K74R, E80A, D82A, K130T, K135R, K136A) | 28 | 81 | 4.5 | 12 | 3.3 | 11 | 1.7 | 22 | 13 | 7.6 | 4.9 | 1.6 | <0.1 | <0.1 | <0.1 | <0.1 | 0.8 | 40 | 14 | 52 | 40 | SY34 |
| SakSTAR(E65D, K74R, E80A, D82A, K130T, | 60 | 100 | 6.8 | 5.8 | 4.4 | 4.5 | 15 | 33 | 32 | 14 | 7.9 | 2.0 | <0.1 | <0.1 | <0.1 | <0.1 | 0.8 | 46 | 28 | 67 | 45 | SY35 |

TABLE 7-continued

Combination mutants of SakSTAR(E80A, D82A, K130T, K135R) with K35A, G36R, E65X, K74X, and selected other amino acids

| Variant | Exp. (mg/mL) | Spec. Act. (kU/mg) | murine MAbs: Epitope cluster I 17G11 | 26A2 | 30A2 | 2B12 | 3G10 | Epitope cluster II 18F12 | 14H5 | 28H4 | 32B2 | 7F10 | Epitope cluster III 7H11 | 25E1 | 40C8 | 24C4 | 1A10 | SakSTAR patient plasma: Pool 10 | Subpool B | Subpool C | Pool 40 | Code |
|---|---|---|---|---|---|---|---|---|---|---|---|---|---|---|---|---|---|---|---|---|---|---|
| K135R, K136A) | | | | | | | | | | | | | | | | | | | | | | |
| SakSTAR(E65Q, K74Q, D82A, S84A, K130T, K135R) | | 170 | NT | | | | | | | | | | | | | | | 45 | 21 | 60 | 45 | SY50N |
| SakSTAR(K35A, E65D, K74R, E80A, D82A, K86A, K130T, K135T) | 68 | 86 | 4.4 | 20 | 5.5 | 15 | 1.5 | 15 | 12 | 6.4 | 6.7 | 1.9 | <0.1 | <0.1 | <0.1 | <0.1 | 1.0 | 36 | 7 | 60 | 55 | SY40 |
| SakSTAR(K35A, K74Q, E80A, D82A, K130T, K135R) | 72 | 120 | 6.1 | 3.4 | 2.5 | 3.0 | 5.9 | 38 | 14 | 9.8 | 6.8 | 1.9 | <0.1 | <0.1 | <0.1 | <0.1 | 0.8 | 49 | 16 | 64 | 48 | SY28 |
| SakSTAR(K35A, E65D, K74R, E80A, D82A, K130T, K135R) | 54 | 190 | 8.1 | 7.5 | 6.9 | 5.5 | 25 | 37 | 34 | 14 | 7.7 | 2.3 | <0.1 | <0.1 | <0.1 | <0.1 | 1.0 | 56 | 28 | 68 | 55 | SY29 |
| SakSTAR(K35A, E65D, K74R, E80A, D82A, V132R, K135R) | 13 | 55 | 6.7 | 23 | 5.3 | 17 | 2.3 | 47 | 19 | 19 | 5.1 | 2.0 | <0.1 | <0.1 | <0.1 | <0.1 | 1.1 | 53 | 20 | 88 | 62 | SY61 |
| SakSTAR(K35A, E65D, K74R, E80A, D82A, T129A, K135R) | 13 | 61 | 7.0 | 13 | 5.1 | 31 | 12 | 27 | 12 | 11 | 6.7 | 2.5 | <0.1 | <0.1 | <0.1 | <0.1 | 1.9 | 56 | 18 | 79 | 60 | SY62 |
| SakSTAR(K35A, E65D, K74R, E80A, D82A, T129A, K135A) | 23 | 21 | 6.9 | 27 | 5.8 | 32 | 20 | 29 | 6.6 | 9.7 | 5.4 | 2.1 | <0.1 | <0.1 | <0.1 | <0.1 | 0 9 | 56 | 17 | 91 | 60 | SY64 |

Association constants ≧ 10-fold lower and antibody absorption ≦60 percent of wild-type SakSTAR are represented in bold type; ≧100,000 HU/mg represented in bold type. NT: not tested.

TABLE 8

SakSTAR variants with intact specific activity (≧100 kHU/mg) and ≦50 percent absorption of human antibodies elicited by treatment with wild-type SakSTAR

| Variant | Spec. Act. (kU/mg) | SakSTAR patient plasma Pool 10 | Subpool B | Subpool C | Pool 40 | Code |
|---|---|---|---|---|---|---|
| SakSTAR(K74Q, K130T, K135R) | 190 | 50 | 25 | 67 | 62 | SY41 |
| SakSTAR(E65A, K74Q, K130T, K135R) | 170 | 45 | 16 | 77 | 55 | SY48 |
| SakSTAR(E65Q, T71S, K74Q, K130T, K135R) | 210 | 49 | 21 | 64 | 59 | SY65 |
| SakSTAR(E65Q, K74Q, E118A, K130A, K135R) | 180 | 50 | 28 | 72 | 58 | SY73 |
| SakSTAR(E65Q, K74Q, N95A, E118A, K130A, K135R) | 190 | 48 | 27 | 74 | 58 | SY74 |
| SakSTAR(K35A, E65Q, K74Q, K130A, K135R) | 110 | 49 | 26 | 63 | 45 | SY75 |
| SakSTAR(E65Q, K74Q, K109A, K130T, K135R) | 210 | 50 | 22 | 68 | 51 | SY81 |
| SakSTAR(K74Q, E80A, D82A, K130T, K135R) | 110 | 46 | 17 | 60 | 48 | SY15 |
| SakSTAR(E65D, K74R, E80A, D82A, K130T, K135R) | 140 | 43 | 11 | 68 | 57 | SY19 |
| SakSTAR(E65S, K74R, E80A, D82A, K130T, K135R) | 110 | 35 | 12 | 60 | — | SY20 |
| SakSTAR(E65D, K74R, E80A, D82A, K130T, K135R, K136A) | 100 | 46 | 28 | 67 | 45 | SY35 |
| SakSTAR(K35A, K74Q, E80A, D82A, K130T, K135R) | 120 | 49 | 16 | 64 | 48 | SY28 |
| SakSTAR(E65D, K74Q, E80A, D82A, K130T, K135R) | 110 | 43 | 13 | 64 | 42 | SY30 |
| SakSTAR(E65Q, K74Q, E80A, D82A, K130T, K135R) | 120 | 43 | 21 | 64 | 42 | SY47 |
| SakSTAR(E65Q, K74Q, D82A, S84A, K130T, K135R) | 170 | 45 | 21 | 60 | 45 | SY50N |
| SakSTAR(K35A, E65D, K74Q, E80A, D82A, K130T, K135R) | 140 | 35 | 8 | 58 | 40 | SY46 |
| SakSTAR(K74Q, K130T, K135R) | 190 | 50 | 25 | 67 | 62 | SY41 |
| SakSTAR(T21A, K35A, E65Q, K74Q, K130A, K135R) | 110 | 50 | 26 | 72 | 50 | SY78 |
| SakSTAR(E65Q, K74Q, K109A, K121A, K130A, K135R) | 140 | 50 | 31 | 73 | 52 | SY88 |
| SakSTAR(E65Q, K74Q, D82A, S84A, K109A, K130A, K135R) | 180 | 43 | 20 | 62 | 44 | SY89 |
| SakSTAR(E65Q, K74Q, N95A, E118A, K130A, K135R, +137A) | 120 | 45 | 30 | 74 | 60 | SY93 |
| SakSTAR(E65Q, K74Q, N95A, E118A, K130A, K135R, K136A, +137K) | 1,400 | 37 | 16 | 70 | 54 | SY94 |
| SakSTAR(E65Q, K74Q, D82A, S84A, E108A, K109A, K130A, K135R) | 110 | 46 | 26 | 63 | 41 | SY95 |

Antibody absorption ≦60 percent of wild-type SakSTAR are represented in bold type; ≧100,000 HU/mg represented in bold type.

TABLE 9

Fibrinolytic properties of selected SakSTAR variants in human plasma in vitro

| Compound | Fibrinolytic potency (C50 in μg/mL) | Residual fibrinogen at C50 (% of baseline) | Fibrinogenolytic potency (C50 in μg/mL) |
|---|---|---|---|
| SakSTAR | 0.18 ± 0.01 | 93 ± 3.5 | 24 ± 3.6 |
| SakSTAR(K74Q, E80A, D82A, K130T, K135R) | 0.15 ± 0.01 | 97 ± 3.0 | 14 ± 3.2 |
| SakSTAR(E65D, K74R, E80A, D82A, K130T, K135R) | 0.24 ± 0.04 | 94 ± 10 | 29 ± 3.1 |
| SakSTAR(K35A, E65D, K74Q, E80A, D82A, K130T, K135R) | 0.11 ± 0.01 | 92 ± 3.0 | 20 ± 2.0 |
| SakSTAR(E65Q, K74Q, N95A, E118A, K130A, K135R, K136A, +137K) | 0.13 | 91 | |

The data represent mean ± SD of 3 experiments.
$C_{50}$: amount of wild type or variant SakSTAR required for 50% clot lysis or 50% fibrinogen breakdown in 2 hrs.

TABLE 10

Pharmacokinetic parameters of the disposition of staphylokinase-related antigen from plasma following bolus injection of SakSTAR variants (100 μg/kg) in hamsters.

| Variant | $C_0$ (μg/mL) | A (μg/mL) | B (μg/mL) | t1/2 (α) (min) | t1/2 (β) (min) | $V_C$ (mL) | AUC (μg.min.mL$^{-1}$) | $Cl_p$ (mL.min$^{-1}$) |
|---|---|---|---|---|---|---|---|---|
| SakSTAR | 0.8 ± 0.1 | 0.6 ± 0.1 | 0.2 ± 0.0 | 2.8 | 7.0 | 13 ± 1.0 | 4.6 ± 0.4 | 2.2 ± 0.2 |
| SakSTAR(K74Q, E80A, D82A, K130T, K135R) | 0.5 ± 0.1 | 0.4 ± 0.1 | 0.1 ± 0.0 | 2.0 | 10 | 20 ± 2.2 | 2.5 ± 0.3 | 4.1 ± 0.5 |
| SakSTAR(E65D, K74R, E80A, D82A, K130T, K135R) | 0.6 ± 0.0 | 0.5 ± 0.0 | 0.1 ± 0.0 | 2.0 | 10 | 16 ± 1.1 | 2.8 ± 0.2 | 3.7 ± 0.3 |
| SakSTAR(K35A, E65DK74Q, E80A, D82A, K130T, K135R) | 1.1 ± 0.1 | 1.0 ± 0.1 | 0.1 ± 0.0 | 2.0 | 24 | 9.6 ± 0.7 | 6.4 ± 0.5 | 1.6 ± 0.1 |

Data are mean ± SEM of 4 experiments.

TABLE 11

Baseline characteristics and treatment outcome of the patients with peripheral arterial occlusion treated with SakSTAR, SakSTAR(K74Q, E80A, D82A, K130T, K135R) or SakSTAR(E65D, K74R, E80A, D82A, K130T, K135R)

| Compound Patient Id. | Gender | Age (yrs) | Clinical ischemia | Locus of occlusion | Age of occlusion (days) | Length of occlusion (cm) | Recanalization by thrombolysis | Total dose of thrombolytic agent (mg) | Total duration of infusion (hrs) | Additional therapy |
|---|---|---|---|---|---|---|---|---|---|---|
| SakSTAR | | | | | | | | | | |
| PUT | M | 66 | Subacute | Femoro-femoral graft | 6 | 5 | Complete | 2 | 23 | Stenting left IF artery |
| VERM | M | 73 | Acute | Right PA | 2 | 6 | Partial | 13 | 23 | Right upper leg amputation |
| GEIV | V | 63 | Restpain | Left SFA | 10 | 5 | Complete | 8 | 7 | PTA |
| POL | M | 46 | Subacute | Right SFA | 30 | 50 | Partial | 22 | 29 | Lumbal sympathectomie |
| BUE | F | 53 | Claudication | Right AF graft | 1 | 15 | Complete | 10 | 13 | Desobstruction |
| VIJ | F | 75 | Subacute | Left FT graft | 2 | 34 | Complete | 7 | 10 | PTA |
| REN | M | 48 | Restpain | Right IF graft | 4 | 20 | Complete | 6.5 | 5 | Left AF graft |
| COR | V | 78 | Acute | Left AFS | 14 | 9 | Complete | 4 | 3 | PTA |
| MAN | M | 67 | Restpain | Left tibial artery | 1 | 6 | Partial | 6 | 5 | — |
| STRA | M | 66 | Claudication | Right FP graft | 14 | 16 | Complete | 19 | 26 | — |
| VANH | M | 38 | Acute | Left radial artery | 4 | 1 | Complete | 6 | 5 | — |
| VANW | F | 57 | Acute | Right FP graft | 1 | 25 | Complete | 20 | 24 | New right FP graft |
| BRA | M | 57 | Acute | Left FT graft | 1 | 30 | Complete | 25 | 43 | — |
| DON | M | 60 | Claudication | Left FT graft | 1 | 20 | Complete | 13 | 19 | PTA + stenting |
| CAM | M | 77 | Restpain | Right SFA graft | 8 | 30 | Complete | 27 | 44 | FF graft |
| Mean ± SEM | | 62 ± 3.1 | | | 6.6 ± 2.1 | 18 ± 3.5 | | 13 ± 2.1 | 19 ± 3.5 | |
| SakSTAR(K74Q, E80A, D82A, K130T, K135R) | | | | | | | | | | |
| IMB | M | 66 | Claudication | Left SFA | 30 | 5 | Complete | 24 | 24 | PTA |
| AZY | M | 44 | Subacute | Right C.I.A. | 7 | 8 | Complete | 18 | 23 | Stenting |
| VIN | M | 51 | Acute | Right E.I.A. | 5 | 70 | Complete | 24 | 30 | — |
| STRO | M | 53 | Claudication | Left FP junction | 14 | 5 | Partial | 3.5 | 2 | Aspiration thrombectomy, PTA |
| VERG | M | 62 | Restpain | Left SFA | 20 | 6 | Complete | 19 | 25 | FP bypass |
| GIE | M | 76 | Acute | Right FP bypass | 2 | 15 | Complete | 8.5 | 17 | — |
| Mean ± SEM | | 59 ± 4.7 | | | 13 ± 4.3 | 18 ± 10 | | 16 ± 3.4 | 20 ± 4.0 | |
| SakSTAR(E65D, K74R, E80A, D82A, K130T, K135R) | | | | | | | | | | |
| URB | M | 57 | Subacute | Right E.I.A. | 4 | 8 | Complete | 8 | 6 | Pseudo aneurysm, right AF graft revision |
| COM | M | 59 | Restpain | Right AF graft | 7 | 65 | Complete | 16 | 22 | — |
| HAC | M | 70 | Restpain | Left anterior tibial artery | 7 | 15 | Complete | 12 | 14 | |
| DEW | F | 76 | Restpain | SFA | 21 | 6 | Complete | 6 | 4 | — |
| VAI | F | 65 | Subacute | Left PA | 25 | 10 | Partial | 8 | 6 | Aspiration thrombectomy |
| FIL | M | 76 | Claudication | Right SFA | 28 | 8 | Complete | 24 | 31 | PTA |
| Mean ± SEM | | 67 ± 3.4 | | | 15 ± 4.3 | 19 ± 9.4 | | 12 ± 2.8 | 14 ± 4.4 | |

AF: aortofemoral; CABG: coronary artery bypass graft; CAD, coronary artery disease; CIA: common iliac artery; COPD: chronic obstructive pulmonary disease; DM: diabetes mellitus; EIA: external iliac artery; FF: femorofibular; FP: femoropopliteal; FT: femorotibial; IA: iliac artery; IF: iliofemoral; occl: occlusion; PA: popliteal artery; PTA: percutaneous transluminal angioplasty; SFA: superficial femoral artery; TA: tibial artery; TF: tibiofibular; SC: subclavian.

TABLE 12

Absorption with SakSTAR variants of antibodies elicited with SakSTAR variants in patients with peripheral arterial occlusion

| | | Insolubilized compound | | |
|---|---|---|---|---|
| Treatment | Absorbant | SakSTAR | SakSTAR (K74Q, E80A, D82A, K130T, K135R) | SakSTAR (E65D, K74R, E80A, D82A, K130T, K135R) |
| SakSTAR (Pool 40) | SakSTAR | 95 | | |
| | SakSTAR (K74Q, E80A, D82A, K130T, K135R) | 48 | | |
| | SalSTAR (E65D, K74R, E80A, D82A, K130T, K135R) | 57 | | |
| SakSTAR (K74Q, E80A, D82A, K130T, K135R) (Imb., Vin., Ver., Gie.) | SakSTAR | 94 | 95 | 95 |
| | SakSTAR (K74Q, E80A, D82A, K130T, K135R) | 91 | 93 | 89 |
| | SalSTAR (E65D, K74R, E80A, D82A, K130T, K135R) | 92 | 94 | 94 |
| SakSTAR (E65D, K74R, E80A, D82A, K130T, K135R) (Urb.) | SakSTAR | 90 | 88 | 85 |
| | SakSTAR (K74Q, E80A, D82A, K130T, K135R) | 94 | 95 | 94 |
| | SalSTAR (E65D, K74R, E80A, D82A, K130T, K135R) | 94 | 95 | 94 |

Data represent median values of the percent absorption with 250 nM absorbant, measured by residual binding to insolubilized compound.
* p = . . . versus SakSTAR; ** p = . . . versus SakSTAR(K74Q, E80A, D82A, K130T, K135R)); and p = . . . versus SakSTAR(E65D, K74R, E80A, D82A, K130T, K135R) by paired non-parametric test.

TABLE 13

Cysteine substitution variants of SakSTAR

| Variant | Spec. Act. (kU/mg) | Dimerization level (%) | PEG derivatization | Clot lysis in vitro ($C_{50}$ in μg/ml) | t1/2(α) (min) | Clp (ml/min) |
|---|---|---|---|---|---|---|
| SakSTAR | 130 | 0 | none | 0.33 | 2.0 | 2.2 |
| SakSTAR (K102C) | 143 | 0 | none | 0.29 | nd | nd |
| SakSTAR (K102C-PEG) | 108 | 0 | 1 | 0.60 | — | — |
| SakSTAR (K109C) monomeric | 100 | 0 | none | 0.52 | nd | nd |
| SakSTAR (K109C) dimeric | 1,650 | >60 | none | 0.17 | 3.6 | 0.52 |
| | 2,235 | >95 | none | 0.12 | nd | nd |

TABLE 14

Cysteine substitution variants of SakSTAR

| Variant | Spec. Act. (kU/mg) | SakSTAR patient plasma Pool 10 | Subpool B | Subpool C | Pool 40 | Code |
|---|---|---|---|---|---|---|
| SakSTAR(K96C) | **790** | 95 | 95 | 95 | | |
| SakSTAR(K102C) | **280** | 95 | 95 | 95 | | |
| SakSTAR(K109C) | **1,900** | 95 | 95 | 94 | 90 | |
| SakSTAR(K35C) | | | | | | |
| SakSTAR(K74C) | | | | | | |
| SakSTAR( . . . ) | | | | | | |
| SakSTAR(K35A, E65D, K74Q, E80A, D82A, K109C, K130T, K135R) | **600** | **46** | **32** | **56** | **36** | SY100 |
| SakSTAR(E65Q, K74Q, D82A, S84A, K109C, K130T, K135R) | **1,100** | **54** | **53** | 77 | **41** | SY102 |

Antibody absorption ≦60 percent of wild-type SakSTAR are represented in bold type; ≧100,000 HU/mg represented in bold type.

What is claimed is:

1. A staphylokinase derivative comprising an amino acid sequence which differs from SEQ ID NO: 10 due to the modification of the sequence within up to four amino acid substitutions consonant with the coding regions of sakØC or sak42D, further due to substitution of one or more amino acids therein with cysteine and further incorporating at least one polyethylene glycol group, thus reducing the clearance from plasma in patients and imparting a fibrinolytic or fibrinogenolytic property to the staphylokinase derivative.

2. The staphylokinase derivative of claim 1 in which one cysteine is substituted at K102 and has a polyethylene glycol group coupled thereto.

3. The staphylokinase derivative of claim 1 in which the staphylokinase specific activity of the staphylokinase derivative is at least 50 percent that of wild type staphylokinase.

4. Staphylokinase derivatives SakSTAR(K35X, G36X, E65X, K74X, E80X, D82X, K102X, E108X, K109X, K121X, K130X, K135X, K136X,+137X) having essentially the amino acid sequence as depicted in FIG. 1 (SEQ ID NO: 10) in which the amino acids Lys in position 35, Gly in position 36, Glu in position 65, Lys in position 74, Glu in position 80, Asp in position 82, Lys in position 102, Glu in position 108, Lys in position 109, Lys in position 121, Lys in position 130, Lys in position 135 and/or Lys in position 136 have been replaced with other amino acids and/or in which one amino acid has been added at the COOH-terminus, thus altering the immunogenicity after administration in patients, and further incorporating at least one polyethylene glycol group.

5. Staphylokinase derivatives having essentially the amino acid sequence depicted in FIG. 3 (SEQ ID NO: 10) in which the boxed or encircled amino acids have been replaced by other amino acids thus reducing the absorption of SakSTAR-specific antibodies from plasma of patients treated with staphylokinase, without reducing the specific activity, the derivative further incorporating at least one polyethylene glycol group.

6. Pharmaceutical composition comprising at least one of the staphylokinase derivatives as claimed in claim 1 together with a suitable excipient.

7. Pharmaceutical composition as claimed in claim 6 for treating arterial thrombosis.

* * * * *

UNITED STATES PATENT AND TRADEMARK OFFICE

CERTIFICATE OF CORRECTION

PATENT NO. : 6,902,733 B2 
DATED : June 7, 2005
INVENTOR(S) : Désire José Collen It is certified that error appears in the above-identified patent and that said Letters Patent is hereby corrected as shown below:

Title page, Item [54] and Column 1, lines 1-2,
Title, "STAPHYLOKINASE DERIVATIVES WITH POLYETHYLENEGLYCOL" should read -- STAPHYLOKINASE DERIVATIVES --.

Column 2,
Line 24, "SUMMARY OF TEE INVENTION" should read -- SUMMARY OF THE INVENTION --.

Column 3,
Line 17, "(open squares, n-6)" should read -- (open squares, n=6) --.
Line 23, "Squares: single amine acid" should read -- Squares: single amino acid --.
Line 30, "(•): 40°C" should read -- (•): 4°C --.
Line 30, "(V): 37" should read -- (∇): 37 --.
Line 34, "following nitra-arterial" should read -- following intra-arterial --.

Column 6,
Line 7, after "ID NO: 2).", insert the following:

-- **The forward and backward primers shared an overlap of around 24 bp (primers not shown). The two purified fragments were then assembled together in a new primerless PCR using Taq polymerase (Boehringer Mannheim). After 7 cycles (1 min at 94°C, 1 min 55°C, 1 min at 72°C). The final product was purified, digested with EcoRI and HindIII and cloned into the corresponding sites of *pMEX602sakB*.** --.

Column 10,
Line 5, "R46177A" should read -- R77A --.

Column 11,
Line 52, "Qiager" should read -- Qiagen --.

Column 12,
Line 1, "SakSTAR(187A) should read -- SakSTAR(I87A) --.
Line 5, "tmplate" should read -- template --.
Line 54, "(5' CAAACAGCCAAGCTTCATTCATTCAC)" should read -- (5' CAAACAGCCAAGCTTCATTCATTCAGC) --.
Line 61, "HindII" should read -- HindIII --.

Column 13,
Line 10, "at 0C" should read -- at 0°C --.
Lines 60 and 62, "with >3" should read -- with ≥3 --.

UNITED STATES PATENT AND TRADEMARK OFFICE
CERTIFICATE OF CORRECTION

PATENT NO. : 6,902,733 B2
DATED : June 7, 2005
INVENTOR(S) : Désire José Collen

It is certified that error appears in the above-identified patent and that said Letters Patent is hereby corrected as shown below:

Column 17,
Line 60, "Thrombolvtic Efficacy" should read -- Thrombolytic Efficacy --.

Column 18,
Line 57, "defied as neutralizing" should read -- defined as neutralizing --.
Line 59, "SakSTAR (K74Q80A)" should read -- SakSTAR (K74QE80A) --.

Column 20,
Beginning at line 2 and ending at line 36, delete the paragraph and insert the following:

**The variants SakSTAR(K102C) and SakSTAR(K109C), were constructed by the spliced overlap extension polymerase chain reaction (SOE-PCR) (24) using *pMEX.SakSTAR* encoding SakSTAR as template. Two fragments were amplified by PCR (30 cycles: 1 sec at 94°C, 1 sec at 50°C, 10 sec at 72°C), the first one starting from the 5' end (primer 818A) of the *staphylokinase* gene to the region to be mutagenized (forward primer), the second one from this same region (backward primer) to the 3' end of the gene with primer 818D (5' CAAACAGCCAAGCTTCATTCATTCAGC) (SEQ ID NO: 5). The forward and backward primers shared an overlap of around 24 bp (for the construction of K102C: TAT GAT AAG AAT TGC AAA AAA GAA GAA (backward) (SEQ ID NO: 6) and TTC TTC TTT TTT GCA ATT CTT ATC ATA (forward) (SEQ ID NO: 7) for the construction of K109C: AAA AAG AAG AAA CGT GCT CTT TCC CTA (backward) (SEQ ID NO: 8) and TAG GGA AAG AGC ACG TTT CTT CTT TTT (forward) (SEQ ID NO: 9). The two purified fragments were then assembled together in a second PCR reaction with the external primers 818A and 818D (30 cycles: 1 sec at 94°C, 1 sec at 50°C, 10 sec at 72°C). The amplified product from this final reaction was purified, digested with EcoRI and HindIII and ligated into the corresponding site of *pMEX.SakSTAR*. For each construction, the sequence of the variant was confirmed by sequencing the entire *Sak*STAR coding region.**

Column 21,
Line 57, "period was < 5%" should read -- period was $\leq$5% --.
Line 59, "C50)" should read -- $C_{50}$) --.

Column 22,
Line 34, "3.6 and ... min" should read -- 3.6 and 3.0 min --.
Line 35, "0.52 and ... mL/min" should read -- 0.52 and 0.32 mL/min --.
Line 39, "to size-eclusion" should read -- to size-exclusion --.

Column 23,
Lines 5-6, delete "(Pool 10)=(Pool 40)+..., with r= ...." and insert in its place -- (Pool 40) = 0..84 x (Pool 10), with r=0.94 and n=61. --.
Line 15, "specific activities > 200" should read -- specific activities $\geq$200 --.

UNITED STATES PATENT AND TRADEMARK OFFICE

CERTIFICATE OF CORRECTION

PATENT NO. : 6,902,733 B2
DATED : June 7, 2005
INVENTOR(S) : Désire José Collen

It is certified that error appears in the above-identified patent and that said Letters Patent is hereby corrected as shown below:

<u>Column 24,</u>
Line 50, “only ... of the ... patients” should read -- only 1 of the 6 patients --.
Lines 51-52, “of ... %” should read -- rate with the variants --.
Line 54, delete “(p=... by Fisher’s exact text)” and insert in its place -- (p = 0.01 by 2 x 3 $CHI^2$ analysis --.

<u>Column 59,</u>
Line 4, “within up to” should read -- with up to --.

Signed and Sealed this

Seventh Day of February, 2006

JON W. DUDAS
*Director of the United States Patent and Trademark Office*

SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: Description of artificial sequence:
Staphylococcus aureus variant expressed by escherichia coli

<400> SEQUENCE: 1
caggaaacag aattcaggag 20

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence:
Staphylococcus aureus variant expressed by escherichia coli

<400> SEQUENCE: 2
caaaacagcc aagcttcatt cattcagc 28

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence:
Staphylococcus aureus variant expressed by escherichia coli

<400> SEQUENCE: 3
caaaacagcc gagcttcatt cattcagc 28

<210> SEQ ID NO 4
<211> LENGTH: 41
<212> TYPE: DNA
<213> ORGANISM: Artificial Sequence
<220> FEATURE:
<223> OTHER INFORMATION: Description of Artificial Sequence:
Staphylococcus aureus variant expressed by escherichia coli

<400> SEQUENCE: 4
ttcagcatgc tgcagttatt tcttttctgc aacaaccttg g 41

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence:
Staphylococcus aureus variant expressed by escherichia coli

<400> SEQUENCE: 5
caaacagcca agcttcattc attcagc 27

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence:
Staphylococcus aureus variant expressed by escherichia coli

<400> SEQUENCE: 6

-continued tatgataaga attgcaaaaa agaagaa 27

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence:
Staphylococcus aureus variant expressed by escherichia coli

<400> SEQUENCE: 7
ttcttctttt ttgcaattct tatcata 27

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence:
Staphylococcus aureus variant expressed by escherichia coli

<400> SEQUENCE: 8
aaaaagaaga aacgtgctct ttcccta 27

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence:
Staphylococcus aureus variant expressed by escherichia coli

<400> SEQUENCE: 9
tagggaaaga gcacgtttct tcttttt 27

<210> SEQ ID NO 10
<211> LENGTH: 136
<212> TYPE: PRT
<213> ORGANISM: Staphylococcus Aureus

<400> SEQUENCE: 10

```
Ser Ser Ser Phe Asp Lys Gly Lys Tyr Lys Lys Gly Asp Asp Ala Ser
  1               5                  10                  15

Tyr Phe Glu Pro Thr Gly Pro Tyr Leu Met Val Asn Val Thr Gly Val
            20                  25                  30

Asp Ser Lys Gly Asn Glu Leu Leu Ser Pro His Tyr Val Glu Phe Pro
        35                  40                  45

Ile Lys Pro Gly Thr Thr Leu Thr Lys Glu Lys Ile Glu Tyr Tyr Val
     50                  55                  60

Glu Trp Ala Leu Asp Ala Thr Ala Tyr Lys Glu Phe Arg Val Val Glu
 65                  70                  75                  80

Leu Asp Pro Ser Ala Lys Ile Glu Val Thr Tyr Tyr Asp Lys Asn Lys
                 85                  90                  95

Lys Lys Glu Glu Thr Lys Ser Phe Pro Ile Thr Glu Lys Gly Phe Val
            100                 105                 110

Val Pro Asp Leu Ser Glu His Ile Lys Asn Pro Gly Phe Asn Leu Ile
        115                 120                 125

Thr Lys Val Val Ile Glu Lys Lys
    130                 135
```